(12) United States Patent
Leyrer et al.

(10) Patent No.: US 8,741,653 B2
(45) Date of Patent: Jun. 3, 2014

(54) SINGLE RECOMBINATION SYSTEM AND METHODS OF USE

(75) Inventors: Sonja Leyrer, Munich (DE); Katja Fischer, München (DE)

(73) Assignee: Emergent Product Development GmbH, Munich (DE)

( * ) Notice: Subject to any disclaimer, the term of this patent is extended or adjusted under 35 U.S.C. 154(b) by 177 days.

(21) Appl. No.: 13/141,595

(22) PCT Filed: Dec. 16, 2009

(86) PCT No.: PCT/EP2009/009028
§ 371 (c)(1),
(2), (4) Date: Oct. 11, 2011

(87) PCT Pub. No.: WO2010/072365
PCT Pub. Date: Jul. 1, 2010

(65) Prior Publication Data
US 2012/0028336 A1    Feb. 2, 2012

Related U.S. Application Data

(60) Provisional application No. 61/139,991, filed on Dec. 22, 2008.

(30) Foreign Application Priority Data

Dec. 22, 2008 (EP) .................................. 08022296

(51) Int. Cl.
*C12N 15/863* (2006.01)
*C12N 15/64* (2006.01)
*C12N 7/02* (2006.01)
*C12N 5/10* (2006.01)

(52) U.S. Cl.
USPC ............... 435/477; 435/235.1; 435/320.1; 435/366; 435/349; 435/239

(58) Field of Classification Search
None
See application file for complete search history.

(56) References Cited

U.S. PATENT DOCUMENTS 7,025,970 B2 * 4/2006 Falkner et al. ............. 424/232.1
2006/0002896 A1   1/2006 Staib et al.

FOREIGN PATENT DOCUMENTS

WO    WO 89/12103  A1     12/1989
WO    WO 2004/087047   *  10/2004
WO    WO 2004/087047 A2    10/2004

OTHER PUBLICATIONS

Genbank AB372858, Dec. 26, 2007.*
Panicali et al (Gene 47:193-199, 1986).*
Alexander et al (Journal of Virology 66:2934, 1992).*
del Mar Lorenzo et al. Biotechniques 24:308-313, 1998.*
Blouch et al. Virology Journal, 2:91, 2005 p. 1-5.*
Examination report EP 08 022 296.1 dated Jun. 22, 2011.*
Blasco, R. and Moss, B., "Selection of recominant vaccinia viruses on the basis of plaque formation," *Gene* 158(2):157-162, Elsevier Science B.V., Netherlands (1995).
Drexler, I., et al., "Modified vaccinia virus Ankara as antigen delivery system: how can we best use its potential?," *Current Opinion in Biotechnology* 15:506-512, Elsevier Ltd., England (2004).
Falkner, F.G., and Moss, B., "Transient Dominant Selection of Recombinant Vaccinia Viruses," *Journal of Virology* 64(6):3108-3111, American Society for Microbiology, United States (1990).
Kurilla, M.G., "Transient Selection During Vaccinia Virus Recombination with Insertion Vectors Without Selectable Markers," *BioTechniques* 22(5):906-910, BioTechniques, United States (1997).
Moss, B., "Poxvirus Expression Vectors," *Current Topics in Microbiology and Immunology* 158:25-38, Springer-Verlag, Germany (1992).
Staib, C., et al., "Transient Host Range Selection for Genetic Engineering of Modified Vaccinia Virus Ankara," *BioTechniques* 28:1137-1148, Informa Life Sciences Publishing, United States (Jun. 2000).
International Search Report for International Application No. PCT/EP2009/009028, European Patent Office, Rijswijk, Netherlands, mailed Apr. 1, 2010.
International Preliminary Report on Patentability with the Written Opinion of the International Searching Authority for International Application No. PCT/EP2009/009028, European Patent Office, Munich, Germany, issued Jun. 29, 2011.
Watt V. M., et al., "Homology Requirements for Recombination in *Escherichia coli,*" *Proc. Natl. Acad. Sci. USA*, 82(14): 4768-4772, National Academy of Sciences, United States (Jul. 1985).

* cited by examiner

Primary Examiner — Mary E Mosher
(74) Attorney, Agent, or Firm — Thompson Coburn LLP

(57) ABSTRACT

The present invention is directed to a modified poxvirus vector that allows for the generation of recombinant poxviruses by a single recombination event. A modified poxvirus vector comprising at least one reporter gene located between two flanking sequences for homologous recombination is disclosed. Furthermore, a host cell comprising said vector and a method for the generation of recombinant poxviruses using said vector are provided.

21 Claims, 6 Drawing Sheets

(896 bps)

(711 bps)

FIG. 11

SEQUENCE LISTING

```
<160> NUMBER OF SEQ ID NOS: 23

<210> SEQ ID NO 1
<211> LENGTH: 4335
<212> TYPE: DNA
<213> ORGANISM: Artificial
<220> FEATURE:
<223> OTHER INFORMATION: Recombination vector vEM07

<400> SEQUENCE: 1
ctaaattgta agcgttaata ttttgttaaa attcgcgtta aattttttgtt aaatcagctc      60 atttttttaac caataggccg aaatcggcaa aatcccttat aaatcaaaag aatagaccga    120 gataggggttg agtgttgttc cagtttggaa caagagtcca ctattaaaga acgtggactc    180
caacgtcaaa gggcgaaaaa ccgtctatca gggcgatggc ccactacgtg aaccatcacc    240
ctaatcaagt tttttggggt cgaggtgccg taaagcacta aatcggaacc ctaaagggag    300
cccccgattt agagcttgac ggggaaccac tatttagttg gtggtcgcca tggatggtgt    360
tattgtatac tgtctaaacg cgttagtaaa acatggcgag gaaataaatc atataaaaaa    420
tgatttcatg attaaaccat gttgtgaaaa agtcaagaac gttcacattg gcggacaatc    480
taaaaacaat acagtgattg cagatttgcc atatatggat aatgcggtat ccgatgtatg    540
caattcactg tataaaaaga atgtatcaag aatatccaga tttgctaatt tgataaagat    600
agatgacgat gacaagactc ctactggtgt atataattat tttaaaccta aagatgccat    660
tcctgttatt atatccatag gaaaggatag agatgtttgt gaactattaa tctcatctga    720
taaagcgtgt gcgtgtatag agttaaattc atataaagta gccattcttc ccatggatgt    780
ttcctttttt accaaaggaa atgcatcatt gattattctc ctgtttgatt tctctatcga    840
tgcggcacct ctcttaagaa gtgtaaccga taataatgtt attatatcta gacaccagcg    900
tctacatgac gagcttccga gttccaattg gttcaagttt tacataagta taaagtccga    960
ctattgttct atattatata tggttgttga tggatctgtg atgcatgcaa tagctgataa  1020
tagaacttac gcaaatatta gcaaaaatat attagacaat actacaatta acgatgagtg  1080
tagatgctgt tattttgaac cacagattag gattcttgat agagatgaga tgctcaatgg  1140
atcatcgtgt gatatgaaca gacattgtat tatgatgaat ttacctgatg taggcgaatt  1200
tggatctagt atgttgggga aatatgaacc tgacatgatt aagattgctc tttcggtggc  1260
tggcacatcg gtggcggccg ctctagaact agtggatccc ccgggctgca ggaagacatg  1320
catcgagatc tggcgccgtt tattcgccat tcaggctgcg caactgttgg gaagggcgat  1380
cggtgcgggc ctcttcgcta ttacgccagc tggcgaaagg gggatgtgct gcaaggcgat  1440
taagttgggt aacgccaggg ttttcccagt cacgacgttg taaaacgacg ccagtgaat   1500 tgtaatacga ctcactatag ggcgaattgg agctccatcg cggcggcggt cgttcgagaa  1560
cgagtgggtc cctgggcta caggagttcg agatcaaact tattgatacc gttgatcttg  1620
aggggggtcc cggtaccagc ttttgttccc tttagtgagg gttaatttcg agcttggcgt  1680
```

```
aatcatggtc atagctgttt cctgtgtgaa attgttatcc gctcacaatt ccacacaaca    1740
tacgagccgg aagcataaag tgtaaagcct ggggtgccta atgagtgagc taactcacat    1800
taattgcgtt gcgcaaactt aattaacact tccgtggcta gcgaattcga tatcaagctt    1860
atcgataccg tcgacctcga gggggggccc ggaaagtttt ataggtagtt gatagaacaa    1920
aatacataat tttgtaaaaa taaatcactt tttatactaa tatgacacga ttaccaatac    1980
ttttgttact aatatcatta gtatacgcta caccttttcc tcagacatct aaaaaaatag    2040
gtgatgatgc aactttatca tgtaatcgaa ataatacaaa tgactacgtt gttatgagtg    2100
cttggtataa ggagcccaat tccattattc ttttagctgc taaaagcgac gtcttgtatt    2160
ttgataatta taccaaggat aaaatatctt acgactctcc atacgatgat ctagttacaa    2220
ctatcacaat taaatcattg actgctagag atgccggtac ttatgtatgt gcattcttta    2280
tgacatcgcc tacaaatgac actgataaag tagattatga agaatactcc acagagttga    2340
ttgtaaatac agatagtgaa tcgactatag acataatact atctggatct acacattcac    2400
cggaaactag ggcttcctcg ctcactgact cgctgcgctc ggtcgttcgg ctgcggcgag    2460
cggtatcagc tcactcaaag gcggtaatac ggttatccac agaatcaggg gataacgcag    2520
gaaagaacat gtgagcaaaa ggccagcaaa aggccaggaa ccgtaaaaag gccgcgttgc    2580
tggcgttttt ccataggctc cgcccccctg acgagcatca caaaaatcga cgctcaagtc    2640
agaggtggcg aaacccgaca ggactataaa gataccaggc gtttccccct ggaagctccc    2700
tcgtgcgctc tcctgttccg accctgccgc ttaccggata cctgtccgcc tttctccctt    2760
cgggaagcgt ggcgctttct catagctcac gctgtaggta tctcagttcg gtgtaggtcg    2820
ttcgctccaa gctgggctgt gtgcacgaac cccccgttca gcccgaccgc tgcgccttat    2880
ccggtaacta tcgtcttgag tccaacccgg taagacacga cttatcgcca ctggcagcag    2940
ccactggtaa caggattagc agagcgaggt atgtaggcgg tgctacagag ttcttgaagt    3000
ggtggcctaa ctacggctac actagaagga cagtatttgg tatctgcgct ctgctgaagc    3060
cagttacctt cggaaaaaga gttggtagct cttgatccgg caaacaaacc accgctggta    3120
gcggtggttt ttttgtttgc aagcagcaga ttacgcgcag aaaaaaagga tctcaagaag    3180
atcctttgat cttttctacg ggtctgacg ctcagtggaa cgaaaactca cgttaaggga    3240
ttttggtcat gagattatca aaaaggatct tcacctagat ccttttaaat taaaaatgaa    3300
gttttaaatc aatctaaagt atatatgagt aaacttggtc tgacagttac caatgcttaa    3360
tcagtgaggc acctatctca gcgatctgtc tatttcgttc atccatagtt gcctgactcc    3420
ccgtcgtgta gataactacg atacgggagg gcttaccatc tggccccagt gctgcaatga    3480
taccgcgaga cccacgctca ccggctccag atttatcagc aataaaccag ccagccggaa    3540
gggccgagcg cagaagtggt cctgcaactt tatccgcctc catccagtct attaattgtt    3600
gccgggaagc tagagtaagt agttcgccag ttaatagttt gcgcaacgtt gttgccattg    3660
ctacaggcat cgtggtgtca cgctcgtcgt ttggtatggc ttcattcagc tccggttccc    3720
aacgatcaag gcgagttaca tgatccccca tgttgtgcaa aaaagcggtt agctccttcg    3780
gtcctccgat cgttgtcaga agtaagttgg ccgcagtgtt atcactcatg gttatggcag    3840
cactgcataa ttctcttact gtcatgccat ccgtaagatg cttttctgtg actggtgagt    3900
actcaaccaa gtcattctga gaatagtgta tgcggcgacc gagttgctct tgcccggcgt    3960
caatacggga taataccgcg ccacatagca gaactttaaa agtgctcatc attggaaaac    4020
gttcttcggg gcgaaaactc tcaaggatct taccgctgtt gagatccagt tcgatgtaac    4080
```

| | | | |
|---|---|---|---|
| ccactcgtgc | acccaactga | tcttcagcat | cttttacttt caccagcgtt tctgggtgag | 4140 |
| caaaaacagg | aaggcaaaat | gccgcaaaaa | agggaataag ggcgacacgg aaatgttgaa | 4200 |
| tactcatact | cttccttttt | caatattatt | gaagcattta tcagggttat tgtctcatga | 4260 |
| gcggatacat | atttgaatgt | atttagaaaa | ataaacaaat aggggttccg cgcacatttc | 4320 |
| cccgaaaagt | gccac | | | 4335 |

<210> SEQ ID NO 2
<211> LENGTH: 2002
<212> TYPE: DNA
<213> ORGANISM: Vaccinia virus strain Ankara

<400> SEQUENCE: 2

| | | | |
|---|---|---|---|
| gtggtaggag | gatctacatc | ctcgactgat | tccacctcgg gatctggatc tgactcggac | 60 |
| tctgtaattt | ccgttacgga | ttggcaaatc | ttatcatcgg tcggtgtttg gtcttgcttt | 120 |
| gtgactttga | taataacatc | gattcccata | tgatgtttgt tttcttcttc cgtacacgat | 180 |
| gaggatgatt | gctgaagact | ggcaggcaca | tgcatgccag tacgatatat tgtttcatga | 240 |
| ttgctattga | ttgagtactg | ttctttatga | ttctacttcc ttaccgtgca ataaattaga | 300 |
| atatatttc | tactttacg | agaaattaat | tattgtattt atgggtgaaa aacttactat | 360 |
| aaaaagcggg | tgggtttgga | attagtgatc | agtttatgta tatcgcaact accgggcata | 420 |
| tggctacatt | acccacatga | taagagattg | tatcagtttc gtagtcttga gtattggtat | 480 |
| tactatatag | tatatagatg | tcgacgctag | agttactgtc tccgaatgcg gcatgatagt | 540 |
| atcattcttt | gctttcgtta | actgtttgga | ggaagaatct ttgttattgc atttaatctc | 600 |
| gaaattcaga | gtgcacacct | ttctcctgta | aagaaacctg aagtcgctac cttattaaga | 660 |
| agacgggatc | gcagtcttta | tgattcatag | taatagttag ttccgacgtt gagatggatt | 720 |
| cgctgagacc | ggtagtggtc | gtccgagtac | acgatgtgtc gttaactgga tacaggttaa | 780 |
| tttccacatc | gatatagtta | aaggtatttc | tgggtacggg ttcgcattta tctgcggaag | 840 |
| agacggtgtg | agaatatgtt | ccgagaccac | acggagaaca gatgacgtct ccggatactc | 900 |
| cgtatcctat | tccacatttt | gtttgggaaa | acatgccttt gcatccatga tcgggagagc | 960 |
| attcacagat | tctattgtga | gtcgtgttac | acgatcgcgt cgacattgtt gacagaaacg | 1020 |
| tgaccttcat | tcttaccgtc | gtccataaat | acgttaggta tgtaccacat actgtcgcga | 1080 |
| acgatgcgtc | catctcataa | tgatttactt | tttcataatt aaagatgtga agaaaaccg | 1140 |
| aacaatatat | ttttttagta | atgtttatgc | gagacatata aaataaactc cgtgtttatg | 1200 |
| atgccggtaa | atgttttat | catcttggac | ggaatcgatt ttgtaatatg ccatggaaac | 1260 |
| aggacattat | cactccatga | taaattattt | aatggagtcg atcctctcat tgttctttgc | 1320 |
| gtatctcaat | ctgtggcgtt | tgcttcgttt | aaataatata tcaaacatgg agacgcctga | 1380 |
| tatgtaggca | ttcttcattc | tattaatgtc | tgctctatag cgctttagtt ccttatgacg | 1440 |
| accggcgata | tcatacttac | tttagaagga | aaatcatcat ctaggattaa ggcgtatctg | 1500 |
| atacaggcga | ataatggttc | aggatataga | tagcgtatat ctctattaaa tgcgtcaatc | 1560 |
| atagtctcta | gagtgggatg | gtaactcagt | aataaatcaa ctagcttctc tttggtaact | 1620 |
| gcttttctgg | atggccgtat | tgattatcga | gcgtgacact cgctccatat tccaataacc | 1680 |
| gctttgcaaa | ttgtatatta | ttgacatcga | ccgcgtaata tagtagagtt atcgatcata | 1740 |
| tctatatcat | ccatgtactt | gcttagtata | tcaaatacat cttcataaca gtgatacccg | 1800 |
| caattattaa | atctcgataa | tatcagaccg | tacatacata gacggccatt gttagatatg | 1860 |

```
tgatttacag ccgcgtgtcc atatttccca cgataaacct tacgacgttt acatcgacga    1920
gattattatt aacaaagttg ttgtccgtcg tcttatccaa catgcattga atgataggta    1980
tacttaccat atcgccgtaa tg                                             2002
```

<210> SEQ ID NO 3
<211> LENGTH: 2002
<212> TYPE: DNA
<213> ORGANISM: Vaccinia virus strain Ankara

<400> SEQUENCE: 3

```
gtaagcattg tctgtattct ggagctattt tctctatatc taatttctga acgttcacca      60
atgtctctag ccactttggc actaatagcg atcattcgct tagcgtcttc tatattatta     120
actggttgat tcaatctatc tagcaatgga ccgtcggaca cgtcattct catgttctta      180 atcaatgtac atacatcgcc gtcatctacc aattcatcca acaacataag cttttttaaaa    240 tcatcattat aataggtttg atcgttgtca tttctccaaa gaatatatct aataagtaga     300
gtcctcatga ttagttaaca actattttt atgttaaatc aattagtaca ccgctatgtt      360
taatacttat tcatatttta gtttttagga ttgagaatca atacaaaaat taatgcatca     420 ttaatttag aaatacttag tttccacgta gtcaatgaaa catttgaact catcgtacag      480
gacgttctcg tacaggacgt aactataaac cggtttatat ttgttcaaga tagatacaaa    540
tccgataact ttttttacga attctacggg atccacttta aaagtgtcat accgggttct    600
tttatttttt ttaaacagat taatggtgtg atgttgatta ggtcttttac gaatttgata    660
tagaatagcg tttacatatt ctccataatg gtcaatcgcc atttgttcgt atgtcataaa    720
ttctttaatt atatgacact gtgtattatt tagttcatcc ttgttcatca ttaggaatct    780
atccaatatg gcaattatac tagaactata ggtgcgttgt atacacatat tgatgtgtct    840
gtttatacaa tccatgctac taccttcggg taaaattgta gcatcatata ccatttctag    900
tactttaggt tcattgttat ccattgcaga ggacgtcatg atcgcatcct aaaaaaatat    960 attatttta tgttattttg ttaaaaataa tcatcgaata cgaatcatcc agtccactga    1020
atagcaaaat ctttactatt ttggtatctt ccaatgtggc tgcctgatgt aatggaaatt    1080
cattctctag aagattttc aatgctccag cgttcaacaa cgtacatact agacgcacgt    1140
tattatcagc tattgcataa acaaggcac tatgtccatg gacatccgcc ttaaatgcat    1200
ctttgctaga gagaaagctt ttcagctgct tagacttcca agtattaatt cgtgacagat    1260
ccatgtctga aacgagacgc taattagtgt ataattttg tcatattgca ccagaattaa    1320
taatatctct aatagatctg attagtagat acatggctat cgcaaaacaa catatacaca    1380
tttaataaaa ataatattta ttaagaaaat tcagattca cgtacccatc aatataaata    1440
aaataatgat tccttacacc gtacccatat taaggagatt ctaccttacc cataaacaat    1500
ataaatccag taatatcatg tctgatgatg aacacaaatg gtgtattaaa ttccagtttt    1560
tcaggagatg atctcgccgt agctaccata atagtagatg cctctgctac agttccttgt    1620
tcgtcgacat ctatctttgc attctgaaac atttttataaa tatataatgg gtccctagtc    1680
atatgtttaa acgacgcatt atctggatta aacatactag gagccatcat ttcggctatc    1740
gacttaatat ccctcttatt ttcgatagaa aatttaggga gtttaagatt gtacacttta    1800
ttccctaatt gaaacgacca atagtctaat tttgcagccg taatagaatc tgtgaaatgg    1860
gtcatattat cacctattgc caggtacata ctaaattag catccttata cggaaggcgt    1920
accatgtcat attctttgtc atcgattgtg attgtatttc cttgcaattt agtaactacg    1980
```
ttcatcatgg gaaccgtttt cg                                              2002

<210> SEQ ID NO 4
<211> LENGTH: 2001
<212> TYPE: DNA
<213> ORGANISM: Vaccinia virus strain Ankara

<400> SEQUENCE: 4

| | | | | | |
|---|---|---|---|---|---|
| tactcatcta | aacgatttag | taaacttgac | taaatcttaa | tagttacata | caaattaaaa    60 |
| taacactatt | tagttggtgg | tcgccatgga | tggtgttatt | gtatactgtc | taaacgcgtt   120 |
| agtaaaacat | ggcgaggaaa | taaatcatat | aaaaaatgat | ttcatgatta | aaccatgttg   180 |
| tgaaaaagtc | aagaacgttc | acattggcgg | acaatctaaa | aacaatacag | tgattgcaga   240 |
| tttgccatat | atggataatg | cggtatccga | tgtatgcaat | tcactgtata | aaagaatgt    300 |
| atcaagaata | tccagatttg | ctaatttgat | aaagatagat | gacgatgaca | agactcctac   360 |
| tggtgtatat | aattatttta | aacctaaaga | tgccattcct | gttattatat | ccataggaaa   420 |
| ggatagagat | gtttgtgaac | tattaatctc | atctgataaa | gcgtgtgcgt | gtatagagtt   480 |
| aaattcatat | aaagtagcca | ttcttcccat | ggatgtttcc | tttttacca | aaggaaatgc   540 |
| atcattgatt | attctcctgt | tgatttctc | tatcgatgcg | gcacctctct | taagaagtgt   600 |
| aaccgataat | aatgttatta | tatctagaca | ccagcgtcta | catgacgagc | ttccgagttc   660 |
| caattggttc | aagttttaca | taagtataaa | gtccgactat | tgttctatat | tatatatggt   720 |
| tgttgatgga | tctgtgatgc | atgcaatagc | tgataataga | acttacgcaa | atattagcaa   780 |
| aaatatatta | gacaatacta | caattaacga | tgagtgtaga | tgctgttatt | ttgaaccaca   840 |
| gattaggatt | cttgatagag | atgagatgct | caatggatca | tcgtgtgata | tgaacagaca   900 |
| ttgtattatg | atgaatttac | ctgatgtagg | cgaatttgga | tctagtatgt | tggggaaata   960 |
| tgaacctgac | atgattaaga | ttgctctttc | ggtggctggt | atttggaaag | ttttataggt  1020 |
| agttgataga | acaaaataca | taattttgta | aaaataaatc | actttttata | ctaatatgac  1080 |
| acgattacca | atacttttgt | tactaatatc | attagtatac | gctacaccttt | tcctcagac  1140 |
| atctaaaaaa | ataggtgatg | atgcaacttt | atcatgtaat | cgaaataata | caaatgacta  1200 |
| cgttgttatg | agtgcttggt | ataaggagcc | caattccatt | attcttttag | ctgctaaaag  1260 |
| cgacgtcttg | tattttgata | attataccaa | ggataaaata | tcttacgact | ctccatacga  1320 |
| tgatctagtt | acaactatca | caattaaatc | attgactgct | agagatgccg | gtacttatgt  1380 |
| atgtgcattc | tttatgacat | cgcctacaaa | tgacactgat | aaagtagatt | atgaagaata  1440 |
| ctccacagag | ttgattgtaa | atacagatag | tgaatcgact | atagacataa | tactatctgg  1500 |
| atctacacat | tcaccggaaa | ctagttctga | gaaacctgat | tatatagata | attctaattg  1560 |
| ctcgtcggta | ttcgaaatcg | cgactccgga | accaattact | gataatgtag | aagatcatac  1620 |
| agacaccgtc | acatacacta | gtgatagcat | taatacagta | agtgcatcat | ctggagaatc  1680 |
| cacaacagac | gagactccgg | aaccaattac | tgataaagaa | gaagatcata | cagttacaga  1740 |
| cactgtctca | tacactacag | taagtacatc | atctggaatt | gtcactacta | aatcaaccac  1800 |
| cgatgatgcg | gatctttatg | atacgtacaa | tgataatgat | acagtaccat | caactactgt  1860 |
| aggcggtagt | acaacctcta | ttagcaatta | taaaaccaag | gactttgtag | aaatatttgg  1920 |
| tattaccgca | ttaattatat | tgtcggccgt | ggcaatattc | tgtattacat | attatatata  1980 |
| taataaacgt | tcacgtaaat | a         |            |            |              2001 |

<210> SEQ ID NO 5

<211> LENGTH: 1996
<212> TYPE: DNA
<213> ORGANISM: Vaccinia virus strain Ankara

<400> SEQUENCE: 5

```
ggcgatatgg taagtatacc tatcattcaa tgcatgttgg ataagacgac ggacaacaac      60
tttgttaata ataatctcgt cgatgtaaac gtcgtaaggt ttatcgtgga aaatatggac     120
acgcggctgt aaatcacata tctaacaatg gccgtctatg tatgtacggt ctgatattat     180
cgagatttaa taattgcggg tatcactgtt atgaagatgt atttgatata ctaagcaagt     240
acatggatga tatagatatg atcgataact ctactatatt acgcggtcga tgtcaataat     300
atacaatttg caaagcggtt attggaatat ggagcgagtg tcacgctcga taatcaatac     360
ggccatccag aaaagcagtt accaaagaga agctagttga tttattactg agttaccatc     420
ccactctaga gactatgatt gacgcattta atagagatat acgctatcta tatcctgaac     480
cattattcgc ctgtatcaga tacgccttaa tcctagatga tgattttcct tctaaagtaa     540
gtatgatatc gccggtcgtc ataaggaact aaagcgctat agagcagaca ttaatagaat     600
gaagaatgcc tacatatcag gcgtctccat gtttgatata ttatttaaac gaagcaaacg     660
ccacagattg agatacgcaa agaacaatga gaggatcgac tccattaaat aatttatcat     720
ggagtgataa tgtcctgttt ccatggcata ttacaaaatc gattccgtcc aagatgataa     780
aaacatttac cggcatcata aacacggagt ttatttata tgtctcgcat aaacattact     840
aaaaaaatat attgttcggt tttctttcac atctttaatt atgaaaaagt aaatcattat     900
gagatggacg catcgttcgc gacagtatgt ggtacatacc taacgtattt atggacgacg     960
gtaagaatga aggtcacgtt tctgtcaaca atgtcgacgc gatcgtgtaa cacgactcac    1020
aatagaatct gtgaatgctc tcccgatcat ggatgcaagg catgtgtttc ccaaacaaaa    1080
tgtggaatag gatacggagt atccggagac gtcatctgtt ctccgtgtgg tctcggaaca    1140
tattctcaca ccgtctcttc cgcagataaa tgcgaacccg tacccagaaa tacctttaac    1200
tatatcgatg tggaaattaa cctgtatcca gttaacgaca catcgtgtac tcggacgacc    1260
actaccggtc tcagcgaatc catctcaacg tcggaactaa ctattactat gaatcataaa    1320
gactgcgatc ccgtcttctt aataaggtag cgacttcagg tttctttaca ggagaaaggt    1380
gtgcactctg aatttcgaga ttaaatgcaa taacaaagat tcttcctcca aacagttaac    1440
gaaagcaaag aatgatacta tcatgccgca ttcggagaca gtaactctag cgtcgacatc    1500
tatatactat atagtaatac caatactcaa gactacgaaa ctgatacaat ctcttatcat    1560
gtgggtaatg tagccatatg cccggtagtt gcgatataca taaactgatc actaattcca    1620
aacccacccg cttttatag taagtttttc acccataaat acaataatta atttctcgta    1680
aaagtagaaa atatattcta atttattgca cggtaaggaa gtagaatcat aaagaacagt    1740
actcaatcaa tagcaatcat gaaacaatat atcgtactgg catgcatgtg cctgccagtc    1800
ttcagcaatc atcctcatcg tgtacggaag aagaaaacaa acatcatatg ggaatcgatg    1860
ttattatcaa agtcacaaag caagaccaaa caccgaccga tgataagatt tgccaatccg    1920
taacggaaat tacagagtcc gagtcagatc cagatcccga ggtggaatca gtcgaggatg    1980
tagatcctcc taccac                                                     1996
```

<210> SEQ ID NO 6
<211> LENGTH: 2002
<212> TYPE: DNA
<213> ORGANISM: Vaccinia virus strain Ankara

<400> SEQUENCE: 6

```
aaataatttt tagtttgcat ccgtagttat cccctttatg taactgtaaa tttctcaacg      60
cgatatctcc attaataatg atgtcgaatt cgtgctgtat acccatactg aatggatgaa     120
cgaataccga cggcgttaat agtaatttac ttttcatct ttacatattg ggtactagtt      180
ttactatcat aagtttataa attccacaag ctactatgga ataagccaac catcttagta     240
taacacacat gtcttaaagt ttattaatta attacatgtt gttttatata tcgctacgaa     300
tttaaacaga gaaatcagtt taggaaaaaa aaatatctat ctacatcatc acgtctctgt     360
attctacgat agagtgctac tttaagatga gacatatccg tgtcatcaaa aatatactcc     420
attaaaatga ttattccggc agcgaacttg atattggata tatcacaacc tttgttaata     480
tctacgacaa tagacagcag tcccatggtt ccataaacag tgagtttatc tttctttgaa     540
gagatatttt gtagagatct tataaaactg tcgaatgaca tcgcatttat atctttagct     600
aaatcgtata tgttaccatc gtaatatcta accgcgtcta tcttaaacgt ttccatcgct     660
ttaaagacgt ttccgataga tggtctcatt tcatcagtca tactgagcca acaaatataa     720
tcgtgtataa catctttgat agaatcgagc tctaaagaaa acgaatcggc tttattatac     780
gcattcatga taaacttaat gaaaaatgtt tttcgttgtt taagttggat gaatagtatg     840
tcttaataat tgttattatt tcattaatta atatttagta acgagtacac tctataaaaa     900
cgagaatgac ataactagtt atcaaagtgt ctaggacgcg taattttcat atggtataga     960
tcctgtaagc attgtctgta ttctggagct attttctcta tatctaattt ctgaacgttc    1020
accaatgtct ctagccactt tggcactaat agcgatcatt cgcttagcgt cttctatatt    1080
attaactggt tgattcaatc tatctagcaa tggaccgtcg gacagcgtca ttctcatgtt    1140
cttaatcaat gtacatacat cgccgtcatc taccaattca tccaacaaca taagcttttt    1200
aaaatcatca ttataatagg tttgatcgtt gtcatttctc caagaatat atctaataag    1260
tagagtcctc atgattagtt aacaactatt ttttatgtta aatcaattag tacaccgcta    1320
tgtttaatac ttattcatat tttagttttt aggattgaga atcaatacaa aaattaatgc    1380
atcattaatt ttagaaatac ttagtttcca cgtagtcaat gaaacatttg aactcatcgt    1440
acaggacgtt ctcgtacagg acgtaactat aaaccggttt atatttgttc aagatagata    1500
caaatccgat aactttttt acgaattcta cgggatccac tttaaagtg tcataccggg      1560
ttcttttat tttttaaac agattaatgg tgtgatgttg attaggtctt ttacgaattt      1620
gatatagaat agcgtttaca tattctccat aatggtcaat cgccatttgt tcgtatgtca    1680
taaattcttt aattatatga cactgtgtat tatttagttc atccttgttc atcattagga    1740
atctatccaa tatggcaatt atactagaac tataggtgcg ttgtatacac atattgatgt    1800
gtctgtttat acaatccatg ctactacctt cgggtaaaat tgtagcatca tataccattt    1860
ctagtacttt aggttcattg ttatccattg cagaggacgt catgatcgca tcctaaaaaa    1920
atatattatt tttatgttat tttgttaaaa ataatcatcg aatacgaatc atccagtcca    1980
ctgaatagca aaatctttac ta                                            2002
```

<210> SEQ ID NO 7
<211> LENGTH: 2002
<212> TYPE: DNA
<213> ORGANISM: Vaccinia virus strain Ankara

<400> SEQUENCE: 7

```
ctaatatagg gctgacgtcg tatactctac acgtgtccac atcctttatt aataatctct      60
```

| | |
|---|---|
| atatctatgg ttgagcaaga ccagtagtat tggatggaaa cattgttatc gatcaaacat | 120 |
| ttaattacat ccttggatag agattctcta tgagacgata tatagtaatg aagagagttc | 180 |
| ttacacatat cactgttgta catacaggta cgaaatacgt aaccggtgct gtaacattct | 240 |
| gatttaagaa gccatagcaa tacttctggt ctcggattag gcgtcgttac gtatatatcc | 300 |
| accaatccga gaccattgat tgcataattc gtattcttgg acggacgtat ccgtttatcc | 360 |
| acaattaggt attttagcag acgtaagtcg aaatcattta tattcgactt gagttcgtta | 420 |
| gaggaattcg aatagctgga tatcagtaga tgcacaatct gagattttac gtatctatgc | 480 |
| ttactgtatg ctcctagcgg agttaatcct tcgttgtttc tacaaagtct ctcgactccg | 540 |
| cgagagagta acagtcgaac aatcttaatg tctgtatcgc atttattgga gacgtaacaa | 600 |
| tgtagcgcat tgtttcctcg tctatctata tgttttgata agttgtgaca cgtttcaatt | 660 |
| tctagtttta ttttttttgta cgtcacatct tcatccagta gacgacatag aatacatgtg | 720 |
| caatccatag ctattctggt gctaattatt cctcataaga tgataaaaag tgtagtgaga | 780 |
| gagcatgaag gagatttagt atttagcagt gcggatatga tccaagaggg tgagatagtc | 840 |
| gttctcgttc agaatctttc gcagcataag tagtatgtcg atatacttat cgttgaagac | 900 |
| tcttccagag acgatagctg attgagtaca aagtccaatg attgcacgaa gttcttcggc | 960 |
| ggttttcatg gagtcatttc tgatgaaaca tttaatgatc taaatttcag tttatgtttg | 1020 |
| taccccgtat tcatacttaa caaattggta ttacatacca ttaataatgc aagcataaaa | 1080 |
| aatcgttagt agatgtttct aaatataggt tccgtaagca agaatataaa gaatgaagcg | 1140 |
| gtaatgataa aatcaatcgt tatctaaaat gatcatactc atttattta ttctattata | 1200 |
| ttaacacata cattttaac agcaacacat tcaatattgt attgttattt ttatattatt | 1260 |
| tacacaatta acaatatatt attagtttat attactgaat taataatata aaattcccaa | 1320 |
| tcttgtcata aacacacact gagaaacagc ataaacacaa aatccatcaa aaatgttgat | 1380 |
| aaattatctg atgttgttgt tcgctgctat gataatcaga tcattcgccg atagtggtaa | 1440 |
| cgctatcgaa acgacatcgc cagaaattac aaacgctaca acagatattc cagctatcag | 1500 |
| attatgcggt ccagagggag atggatattg tttacacggt gactgtatcc acgctagaga | 1560 |
| tatcgacggt atgtattgta gatgctctca tggttataca ggcattagat gtcagcatgt | 1620 |
| agtattagta gactatcaac gttcagaaaa accaaacact acaacgtcat atatcccatc | 1680 |
| tcccggtatt atgcttgtat tagtaggcat tattattatt acgtgttgtc tattatctgt | 1740 |
| ttataggttc actcgacgaa ctaaactacc tatacaagat atggttgtgc cataattttt | 1800 |
| ataaattttt tttatgagta tttttacaaa aatgtataaa gtgtatgtct tatgtatatt | 1860 |
| tataaaaatg ctaaatatgc gatgtatcta tgttatttgt atttatctaa acaataccctc | 1920 |
| tacctctaga tattatacaa aaatttttta tttcggcata ttaaagtaaa atctagttac | 1980 |
| cttgaaaatg aatacagtgg gt | 2002 |

<210> SEQ ID NO 8
<211> LENGTH: 62
<212> TYPE: DNA
<213> ORGANISM: artificial
<220> FEATURE:
<223> OTHER INFORMATION: Primer oEM167

<400> SEQUENCE: 8

| | |
|---|---|
| tccctatcag tgatagagat ctccctatca gtgatagaga tatgaggggc atgaagctgc | 60 |
| tg | 62 |

<210> SEQ ID NO 9
<211> LENGTH: 22
<212> TYPE: DNA
<213> ORGANISM: artificial
<220> FEATURE:
<223> OTHER INFORMATION: Primer oEM168

<400> SEQUENCE: 9
gagctcctac ttcagcatca cc                                              22

<210> SEQ ID NO 10
<211> LENGTH: 65
<212> TYPE: DNA
<213> ORGANISM: artificial
<220> FEATURE:
<223> OTHER INFORMATION: Primer oEM169

<400> SEQUENCE: 10
gactagtaaa aattgaaatt ttattttttt tttttggaat ataaatatcc ctatcagtga    60
tagag                                                                 65

<210> SEQ ID NO 11
<211> LENGTH: 68
<212> TYPE: DNA
<213> ORGANISM: artificial
<220> FEATURE:
<223> OTHER INFORMATION: Primer oEM163

<400> SEQUENCE: 11
gggagctcaa aaattgaaat tttattttttt tttttggaa tataaataat gtctagatta    60
gataaaag                                                              68

<210> SEQ ID NO 12
<211> LENGTH: 25
<212> TYPE: DNA
<213> ORGANISM: artificial
<220> FEATURE:
<223> OTHER INFORMATION: Primer oEM164

<400> SEQUENCE: 12
gctagcttaa taagatctga attcc                                           25

<210> SEQ ID NO 13
<211> LENGTH: 26
<212> TYPE: DNA
<213> ORGANISM: artificial
<220> FEATURE:
<223> OTHER INFORMATION: Primer oEM165

<400> SEQUENCE: 13
ctcgagatgt ctagattaga taaaag                                          26

<210> SEQ ID NO 14
<211> LENGTH: 27
<212> TYPE: DNA
<213> ORGANISM: artificial
<220> FEATURE:
<223> OTHER INFORMATION: Primer oEM166

<400> SEQUENCE: 14
ccgggccctt aataagatct gaattcc                                         27

<210> SEQ ID NO 15
<211> LENGTH: 5687
<212> TYPE: DNA

```
<213> ORGANISM: artificial
<220> FEATURE:
<223> OTHER INFORMATION: vector vEM11
<220> FEATURE:
<221> NAME/KEY: misc_feature
<222> LOCATION: (338)..(1263)
<223> OTHER INFORMATION: Flank1 Del3
<220> FEATURE:
<221> NAME/KEY: gene
<222> LOCATION: (1283)..(1962)
<223> OTHER INFORMATION: Amazi green (C)
<220> FEATURE:
<221> NAME/KEY: misc_feature
<222> LOCATION: (2002)..(1963)
<223> OTHER INFORMATION: Ps
<220> FEATURE:
<221> NAME/KEY: misc_feature
<222> LOCATION: (2009)..(2048)
<223> OTHER INFORMATION: Ps
<220> FEATURE:
<221> NAME/KEY: gene
<222> LOCATION: (2049)..(2447)
<223> OTHER INFORMATION: BsdR
<220> FEATURE:
<221> NAME/KEY: gene
<222> LOCATION: (2463)..(2653)
<223> OTHER INFORMATION: MAV164R (putative 34.9k protein)
<220> FEATURE:
<221> NAME/KEY: misc_feature
<222> LOCATION: (2463)..(2653)
<223> OTHER INFORMATION: Flank1 Del3
<220> FEATURE:
<221> NAME/KEY: promoter
<222> LOCATION: (2817)..(2969)
<223> OTHER INFORMATION: lac promoter
<220> FEATURE:
<221> NAME/KEY: gene
<222> LOCATION: (2818)..(3170)
<223> OTHER INFORMATION: LacZ
<220> FEATURE:
<221> NAME/KEY: promoter
<222> LOCATION: (2843)..(2863)
<223> OTHER INFORMATION: T3
<220> FEATURE:
<221> NAME/KEY: promoter
<222> LOCATION: (2988)..(3008)
<223> OTHER INFORMATION: T7
<220> FEATURE:
<221> NAME/KEY: misc_feature
<222> LOCATION: (3243)..(3753)
<223> OTHER INFORMATION: Flank2 Del3
<220> FEATURE:
<221> NAME/KEY: gene
<222> LOCATION: (4702)..(5559)
<223> OTHER INFORMATION: AmpR

<400> SEQUENCE: 15
ctaaattgta agcgttaata ttttgttaaa attcgcgtta aatttttgtt aaatcagctc      60
attttttaac cataggccg aaatcggcaa atcccttat aaatcaaaag aatagaccga      120
gatagggttg agtgttgttc cagtttggaa caagagtcca ctattaaaga acgtggactc     180
caacgtcaaa gggcgaaaaa ccgtctatca gggcgatggc ccactacgtg aaccatcacc     240
ctaatcaagt ttttgggt cgaggtgccg taaagcacta atcggaacc ctaaagggag        300 ccccgattt agagcttgac ggggaaccac tatttagttg gtggtcgcca tgatggtgt      360 tattgtatac tgtctaaacg cgttagtaaa acatggcgag gaaataaatc atataaaaaa     420
tgatttcatg attaaaccat gttgtgaaaa agtcaagaac gttcacattg gcggacaatc     480
taaaaacaat acagtgattg cagatttgcc atatatggat aatgcggtat ccgatgtatg     540
caattcactg tataaaaaga atgtatcaag aaatccaga tttgctaatt tgataaagat       600
agatgacgat gacaagactc ctactggtgt atataattat tttaaaccta agatgccat      660
```

```
tcctgttatt atatccatag gaaaggatag agatgtttgt gaactattaa tctcatctga    720
taaagcgtgt gcgtgtatag agttaaattc atataaagta gccattcttc ccatggatgt    780 ttccttttt accaaaggaa atgcatcatt gattattctc ctgtttgatt tctctatcga     840
tgcggcacct ctcttaagaa gtgtaaccga taataatgtt attatatcta gacaccagcg    900
tctacatgac gagcttccga gttccaattg gttcaagttt tacataagta taaagtccga    960
ctattgttct atattatata tggttgttga tggatctgtg atgcatgcaa tagctgataa   1020
tagaacttac gcaaatatta gcaaaaatat attagacaat actacaatta acgatgagtg   1080
tagatgctgt tattttgaac cacagattag gattcttgat agagatgaga tgctcaatgg   1140
atcatcgtgt gatatgaaca gacattgtat tatgatgaat ttacctgatg taggcgaatt   1200
tggatctagt atgttgggga aatatgaacc tgacatgatt aagattgctc tttcggtggc   1260
tggcacatcg gtggcggccg cttacttggc ctgactcggc agcatagaat agcgagcaac   1320
ggcattctca tagagcttga ccttgttgta atctttgtca tgcttcaaaa tctcaatgcg   1380
gtggtccaca aagtgatagt ctggcaaacg gacatccttc tttgctttgt aagtagtttt   1440
gaaatcacat cgataatggc cacctccttc aagcaacaga gccatgttaa catcacccttt  1500 cagcactcca tcacgtacgt acattttctc agtggatggc tcccatttaa gagtcttctt   1560
ctgcataacc ggaccattgg gaggaaagtt cacaccatca aaacgaatgt catagaaaaa   1620
acagtcgccc ctcatgctta tgttgcttgt ggcggtgcaa atgccctggt cttcataagt   1680
catgcttctt tcccagtgat acccctcagg aaaagtctgc ttgaaatagt cctgaatatc   1740
tgctgggtac ttggtgaatg ccctgttgcc gtactggaac actgttgtca agatatcgta   1800
agcgaaaggc agaggtgcgc cttcagtgac gttcaggtct aaaatctgcg ttccctcgta   1860
aggatttcct tttccttctc cttcaatcac gaaattatgc ccgtttacag tgcctctcat   1920
acacagcttg atcttcatct ctggtttaat cacactcacc attatttata ttccaaaaaa   1980
aaaaaataaa atttcaattt tgccggcaa aaattgaaat tttatttttt tttttggaa     2040 tataaataat ggccaagcct ttgtctcaag aagaatccac cctcattgaa agagcaacgg   2100
ctacaatcaa cagcatcccc atctctgaag actacagcgt cgccagcgca gctctctcta   2160
gcgacggccg catcttcact ggtgtcaatg tatatcattt tactggggga ccttgtgcag   2220
aactcgtggt gctgggcact gctgctgctg cggcagctgg caacctgact tgtatcgtcg   2280
cgatcggaaa tgagaacagg ggcatcttga gccctgcgg acggtgccga caggtgcttc    2340
tcgatctgca tcctgggatc aaagccatag tgaaggacag tgatggacag ccgacggcag   2400
ttgggattcg tgaattgctg ccctctggtt atgtgtggga gggctaaact agttcaatta   2460
acgatgagtg tagatgctgt tattttgaac cacagattag gattcttgat agagatgaga   2520
tgctcaatgg atcatcgtgt gatatgaaca gacattgtat tatgatgaat ttacctgatg   2580
taggcgaatt tggatctagt atgttgggga aatatgaacc tgacatgatt aagattgctc   2640
tttcggtggc tggcccgggc tgcaggaaga catgcatcga gatctggcgc gtttgcgca    2700 acgcaattaa tgtgagttag ctcactcatt aggcaccca ggctttacac tttatgcttc    2760
cggctcgtat gttgtgtgga attgtgagcg ataacaatt tcacacagga aacagctatg    2820
accatgatta cgccaagctc gaaattaacc ctcactaaag ggaacaaaag ctggtaccgg   2880 gaccccctc aagatcaacg gtatcaataa gtttgatctc gaactcctgt agcccagggg    2940
acccactcgt tctcgaacga ccgccgccgc gatggagctc caattcgccc tatagtgagt   3000
cgtattacaa ttcactggcc gtcgttttac aacgtcgtga ctgggaaaac cctggcgtta   3060
```

```
cccaacttaa tcgccttgca gcacatcccc ctttcgccag ctggcgtaat agcgaagagg   3120
cccgcaccga tcgcccttcc caacagttgc gcagcctgaa tggcgaatgg aaacttaatt   3180
aacacgtggc tagcgaattc gatatcaagc ttatcgatac cgtcgacctc gagggggggc   3240
ccggaaagtt ttataggtag ttgatagaac aaaatacata attttgtaaa aataaatcac   3300
tttttatact aatatgacac gattaccaat acttttgtta ctaatatcat tagtatacgc   3360 tacaccttt cctcagacat ctaaaaaaat aggtgatgat gcaactttat catgtaatcg   3420
aaataataca aatgactacg ttgttatgag tgcttggtat aaggagccca attccattat   3480
tcttttagct gctaaaagcg acgtcttgta ttttgataat tataccaagg ataaaatatc   3540
ttacgactct ccatacgatg atctagttac aactatcaca attaaatcat tgactgctag   3600
agatgccggt acttatgtat gtgcattctt tatgacatcg cctacaaatg acactgataa   3660
agtagattat gaagaatact ccacagagtt gattgtaaat acagatagtg aatcgactat   3720
agacataata ctatctggat ctacacattc accggaaact agggcttcct cgctcactga   3780
ctcgctgcgc tcggtcgttc ggctgcggcg agcggtatca gctcactcaa aggcggtaat   3840
acggttatcc acagaatcag gggataacgc aggaaagaac atgtgagcaa aaggccagca   3900
aaaggccagg aaccgtaaaa aggccgcgtt gctggcgttt ttccataggc tccgcccccc   3960
tgacgagcat cacaaaaatc gacgctcaag tcagaggtgg cgaaacccga caggactata   4020
aagataccag gcgtttcccc ctggaagctc cctcgtgcgc tctcctgttc cgaccctgcc   4080
gcttaccgga tacctgtccg cctttctccc ttcgggaagc gtggcgcttt ctcatagctc   4140
acgctgtagg tatctcagtt cggtgtaggt cgttcgctcc aagctgggct gtgtgcacga   4200
accccccgtt cagcccgacc gctgcgcctt atccggtaac tatcgtcttg agtccaaccc   4260
ggtaagacac gacttatcgc cactggcagc agccactggt aacaggatta gcagagcgag   4320
gtatgtaggc ggtgctacag agttcttgaa gtggtggcct aactacggct acactagaag   4380
gacagtattt ggtatctgcg ctctgctgaa gccagttacc ttcggaaaaa gagttggtag   4440
ctcttgatcc ggcaaacaaa ccaccgctgg tagcggtggt ttttttgttt gcaagcagca   4500
gattacgcgc agaaaaaaag gatctcaaga agatcctttg atcttttcta cggggtctga   4560
cgctcagtgg aacgaaaact cacgttaagg gattttggtc atgagattat caaaaaggat   4620
cttcacctag atccttttaa attaaaaatg aagttttaaa tcaatctaaa gtatatatga   4680
gtaaacttgg tctgacagtt accaatgctt aatcagtgag gcacctatct cagcgatctg   4740
tctatttcgt tcatccatag ttgcctgact ccccgtcgtg tagataacta cgatacggga   4800
gggcttacca tctggcccca gtgctgcaat gataccgcga cccacgctca ccggctcca   4860 agatttatca gcaataaacc agccagccgg aagggccgag cgcagaagtg gtcctgcaac   4920
tttatccgcc tccatccagt ctattaattg ttgccgggaa gctagagtaa gtagttcgcc   4980
agttaatagt ttgcgcaacg ttgttgccat tgctacaggc atcgtggtgt cacgctcgtc   5040
gtttggtatg gcttcattca gctccggttc ccaacgatca aggcgagtta catgatcccc   5100
catgttgtgc aaaaaagcgg ttagctcctt cggtcctccg atcgttgtca gaagtaagtt   5160
ggccgcagtg ttatcactca tggttatggc agcactgcat aattctctta ctgtcatgcc   5220
atccgtaaga tgcttttctg tgactggtga gtactcaacc aagtcattct gagaatagtg   5280
tatgcggcga ccgagttgct cttgcccggc gtcaatacgg gataataccg cgccacatag   5340
cagaacttta aaagtgctca tcattggaaa acgttcttcg gggcgaaaac tctcaaggat   5400
cttaccgctg ttgagatcca gttcgatgta acccactcgt gcacccaact gatcttcagc   5460
```

```
atcttttact tcaccagcg tttctgggtg agcaaaaaca ggaaggcaaa atgccgcaaa      5520
aaagggaata agggcgacac ggaaatgttg aatactcata ctcttccttt ttcaatatta      5580
ttgaagcatt tatcagggtt attgtctcat gagcggatac atatttgaat gtatttagaa      5640
aaataaacaa ataggggttc cgcgcacatt tccccgaaaa gtgccac                    5687
```

```
<210> SEQ ID NO 16
<211> LENGTH: 6096
<212> TYPE: DNA
<213> ORGANISM: Artificial
<220> FEATURE:
<223> OTHER INFORMATION: vector vEM12
<220> FEATURE:
<221> NAME/KEY: misc_feature
<222> LOCATION: (338)..(1263)
<223> OTHER INFORMATION: Flank1 Del3
<220> FEATURE:
<221> NAME/KEY: gene
<222> LOCATION: (1283)..(1962)
<223> OTHER INFORMATION: Azami green
<220> FEATURE:
<221> NAME/KEY: misc_feature
<222> LOCATION: (2002)..(1963)
<223> OTHER INFORMATION: Ps
<220> FEATURE:
<221> NAME/KEY: misc_feature
<222> LOCATION: (2009)..(2048)
<223> OTHER INFORMATION: Ps
<220> FEATURE:
<221> NAME/KEY: gene
<222> LOCATION: (2049)..(2447)
<223> OTHER INFORMATION: BsdR
<220> FEATURE:
<221> NAME/KEY: promoter
<222> LOCATION: (2454)..(2493)
<223> OTHER INFORMATION: Ps promoter
<220> FEATURE:
<221> NAME/KEY: misc_feature
<222> LOCATION: (2494)..(2534)
<223> OTHER INFORMATION: TetO2
<220> FEATURE:
<221> NAME/KEY: gene
<222> LOCATION: (2535)..(3383)
<223> OTHER INFORMATION: DNAse
<220> FEATURE:
<221> NAME/KEY: gene
<222> LOCATION: (3389)..(3579)
<223> OTHER INFORMATION: LacZ
<220> FEATURE:
<221> NAME/KEY: promoter
<222> LOCATION: (3397)..(3417)
<223> OTHER INFORMATION: T7 promoter
<220> FEATURE:
<221> NAME/KEY: misc_feature
<222> LOCATION: (3652)..(4162)
<223> OTHER INFORMATION: Flank2 Del3
<220> FEATURE:
<221> NAME/KEY: gene
<222> LOCATION: (5111)..(5968)
<223> OTHER INFORMATION: AmpR

<400> SEQUENCE: 16
ctaaattgta agcgttaata ttttgttaaa attcgcgtta aattttgtt aaatcagctc       60 attttttaac caataggccg aaatcggcaa atcccttat aaatcaaaag aatagaccga      120
gatagggttg agtgttgttc cagtttggaa caagagtcca ctattaaaga acgtggactc     180
caacgtcaaa gggcgaaaaa ccgtctatca gggcgatggc ccactacgtg aaccatcacc     240
ctaatcaagt ttttttgggt cgaggtgccg taaagcacta atcggaacc ctaaagggag      300 ccccccgattt agagcttgac ggggaaccac tatttagttg gtggtcgcca tggatggtgt    360
tattgtatac tgtctaaacg cgttagtaaa acatggcgag gaaataaatc atataaaaaaa    420
```

```
tgatttcatg attaaaccat gttgtgaaaa agtcaagaac gttcacattg gcggacaatc     480
taaaaacaat acagtgattg cagatttgcc atatatggaa aatgcggtat ccgatgtatg     540
caattcactg tataaaaaga atgtatcaag aatatccaga tttgctaatt tgataaagat     600
agatgacgat gacaagactc ctactggtgt atataattat tttaaaccta aagatgccat     660
tcctgttatt atatccatag gaaaggatag agatgtttgt gaactattaa tctcatctga     720
taaagcgtgt gcgtgtatag agttaaattc atataaagta gccattcttc ccatggatgt     780
ttcctttttt accaaaggaa atgcatcatt gattattctc ctgtttgatt tctctatcga     840
tgcggcacct ctcttaagaa gtgtaaccga taataatgtt attatatcta gacaccagcg     900
tctacatgac gagcttccga gttccaattg gttcaagttt tacataagta taaagtccga     960
ctattgttct atattatata tggttgttga tggatctgtg atgcatgcaa tagctgataa    1020
tagaacttac gcaaatatta gcaaaaatat attagacaat actacaatta acgatgagtg    1080
tagatgctgt tattttgaac cacagattag gattcttgat agagatgaga tgctcaatgg    1140
atcatcgtgt gatatgaaca gacattgtat tatgatgaat ttacctgatg taggcgaatt    1200
tggatctagt atgttgggga aatatgaacc tgacatgatt aagattgctc tttcggtggc    1260
tggcacatcg gtggcggccg cttacttggc ctgactcggc agcatagaat agcgagcaac    1320
ggcattctca tagagcttga ccttgttgta atctttgtca tgcttcaaaa tctcaatgcg    1380
gtggtccaca aagtgatagt ctggcaaacg gacatccttc tttgctttgt aagtagtttt    1440
gaaatcacat cgataatggc cacctccttc aagcaacaga gccatgttaa catcacccct    1500
cagcactcca tcacgtacgt acattttctc agtggatggc tcccatttaa gagtcttctt    1560
ctgcataacc ggaccattgg gaggaaagtt cacaccatca aaacgaatgt catagaaaaa    1620
acagtcgccc ctcatgctta tgttgcttgt ggcggtgcaa atgccctggt cttcataagt    1680
catgcttctt tcccagtgat acccctcagg aaaagtctgc ttgaaatagt cctgaatatc    1740
tgctgggtac ttggtgaatg ccctgttgcc gtactggaac actgttgtca agatatcgta    1800
agcgaaaggc agaggtgcgc cttcagtgac gttcaggtct aaaatctgcg ttccctcgta    1860
aggatttcct tttccttctc cttcaatcac gaaattatgc ccgtttacag tgcctctcat    1920
acacagcttg atcttcatct ctggtttaat cacactcacc attatttata ttccaaaaaa    1980
aaaaaataaa atttcaattt ttgccggcaa aaattgaaat tttattttt tttttggaa     2040 tataaataat ggccaagcct ttgtctcaag aagaatccac cctcattgaa agagcaacgg    2100
ctacaatcaa cagcatcccc atctctgaag actacagcgt cgccagcgca gctctctcta    2160
gcgacggccg catcttcact ggtgtcaatg tatatcattt tactgggga ccttgtgcag     2220 aactcgtggt gctgggcact gctgctgctg cggcagctgg caacctgact tgtatcgtcg    2280
cgatcggaaa tgagaacagg ggcatcttga gcccctgcgg acggtgccga caggtgcttc    2340
tcgatctgca tcctgggatc aaagccctag tgaaggacag tgatggacag ccgacggcag    2400
ttgggattcg tgaattgctg ccctctggtt atgtgtggga gggctaaact agtaaaaatt    2460
gaaattttat ttttttttt tggaatataa atatccctat cagtgataga gatctcccta    2520
tcagtgatag agatatgagg ggcatgaagc tgctgggggc gctgctggca ctggcggccc    2580
tactgcaggg ggccgtgtcc ctgaagatcg cagccttcaa catccagaca tttggggaga    2640
ccaagatgtc caatgccacc ctcgtcagct acattgtgca gatcctgagc cgctatgaca    2700
tcgccctggt ccaggaggtc agagacagcc acctgactgc cgtggggaag ctgctggaca    2760
acctcaatca ggatgcacca gacacctatc actacgtggt cagtgagcca ctgggacgga    2820
```

```
acagctataa ggagcgctac ctgttcgtgt acaggcctga ccaggtgtct gcggtggaca      2880
gctactacta cgatgatggc tgcgagccct gcgggaacga caccttcaac cgagagccag      2940
ccattgtcag gttcttctcc cggttcacag aggtcaggga gtttgccatt gttccctgc       3000 atgcggcccc gggggacgca gtagccgaga tcgacgctct ctatgacgtc tacctggatg      3060
tccaagagaa atgggcttg gaggacgtca tgttgatggg cgacttcaat gcgggctgca       3120
gctatgtgag accctcccag tggtcatcca tccgcctgtg acaagcccc accttccagt       3180 ggctgatccc cgacagcgct gacaccacag ctacacccac gcactgtgcc tatgacagga      3240
tcgtggttgc agggatgctg ctccgaggcg ccgttgttcc cgactcggct cttcccttta      3300
acttccaggc tgcctatggc ctgagtgacc aactggccca agccatcagt gaccactatc      3360
cagtggaggt gatgctgaag taggagctcc aattcgccct atagtgagtc gtattacaat      3420
tcactggccg tcgttttaca cgtcgtgac tgggaaaacc ctggcgttac ccaacttaat       3480
cgccttgcag cacatccccc tttcgccagc tggcgtaata gcgaagaggc ccgcaccgat      3540
cgcccttccc aacagttgcg cagcctgaat ggcgaatgga acttaatta acacgtggct       3600 agcgaattcg atatcaagct tatcgatacc gtcgacctcg aggggggggcc cggaaagttt     3660 tataggtagt tgatagaaca aaatacataa ttttgtaaaa ataaatcact ttttatacta      3720
atatgacacg attaccaata cttttgttac taatatcatt agtatacgct cacccttttc      3780
ctcagacatc taaaaaaata ggtgatgatg caactttatc atgtaatcga ataatacaa       3840 atgactacgt tgttatgagt gcttggtata aggagcccaa ttccattatt cttttagctg      3900
ctaaaagcga cgtcttgtat tttgataatt ataccaagga taaatatct tacgactctc       3960 catacgatga tctagttaca actatcacaa ttaaatcatt gactgctaga gatgccggta      4020
cttatgtatg tgcattcttt atgacatcgc ctacaaatga cactgataaa gtagattatg      4080
aagaatactc cacagagttg attgtaaata cagatagtga atcgactata gacataatac      4140
tatctggatc tacacattca ccggaaacta gggcttcctc gctcactgac tcgctgcgct      4200
cggtcgttcg gctgcggcga gcggtatcag ctcactcaaa ggcggtaata cggttatcca      4260
cagaatcagg ggataacgca ggaaagaaca tgtgagcaaa aggccagcaa aaggccagga      4320
accgtaaaaa ggccgcgttg ctggcgtttt tccataggct ccgcccccct gacgagcatc      4380
acaaaaatcg acgctcaagt cagaggtggc gaaacccgac aggactataa agataccagg      4440
cgtttccccc tggaagctcc ctcgtgcgct ctcctgttcc gaccctgccg cttaccggat      4500
acctgtccgc ctttctccct tcgggaagcg tggcgctttc tcatagctca cgctgtaggt      4560
atctcagttc ggtgtaggtc gttcgctcca agctgggctg tgtgcacgaa ccccccgttc      4620
agcccgaccg ctgcgcctta tccggtaact atcgtcttga gtccaacccg gtaagacacg      4680
acttatcgcc actggcagca gccactggta acaggattag cagagcgagg tatgtaggcg      4740
gtgctacaga gttcttgaag tggtggccta actacggcta cactagaagg acagtatttg      4800
gtatctgcgc tctgctgaag ccagttacct tcggaaaaag agttggtagc tcttgatccg      4860
gcaaacaaac caccgctggt agcggtggtt ttttgtttg caagcagcag attacgcgca       4920 gaaaaaagg atctcaagaa gatcctttga tcttttctac ggggtctgac gctcagtgga      4980
acgaaaactc acgttaaggg attttggtca tgagattatc aaaaaggatc ttcacctaga      5040
tccttttaaa ttaaaaatga agttttaaat caatctaaag tatatatgag taaacttggt      5100
ctgacagtta ccaatgctta atcagtgagg cacctatctc agcgatctgt ctatttcgtt      5160
catccatagt tgcctgactc cccgtcgtgt agataactac gatacgggag ggcttaccat      5220
```

```
ctggccccag tgctgcaatg ataccgcgag acccacgctc accggctcca gatttatcag    5280
caataaacca gccagccgga agggccgagc gcagaagtgg tcctgcaact ttatccgcct    5340
ccatccagtc tattaattgt tgccgggaag ctagagtaag tagttcgcca gttaatagtt    5400
tgcgcaacgt tgttgccatt gctacaggca tcgtggtgtc acgctcgtcg tttggtatgg    5460
cttcattcag ctccggttcc caacgatcaa ggcgagttac atgatccccc atgttgtgca    5520
aaaaagcggt tagctccttc ggtcctccga tcgttgtcag aagtaagttg gccgcagtgt    5580
tatcactcat ggttatggca gcactgcata attctcttac tgtcatgcca tccgtaagat    5640
gcttttctgt gactggtgag tactcaacca agtcattctg agaatagtgt atgcggcgac    5700
cgagttgctc ttgcccggcg tcaatacggg ataataccgc gccacatagc agaactttaa    5760
aagtgctcat cattggaaaa cgttcttcgg ggcgaaaact ctcaaggatc ttaccgctgt    5820
tgagatccag ttcgatgtaa cccactcgtg cacccaactg atcttcagca tcttttactt    5880
tcaccagcgt ttctgggtga gcaaaaacag gaaggcaaaa tgccgcaaaa aagggaataa    5940
gggcgacacg gaaatgttga atactcatac tcttcctttt tcaatattat tgaagcattt    6000
atcagggtta ttgtctcatg agcggataca tatttgaatg tatttagaaa aataaacaaa    6060
taggggttcc gcgcacattt ccccgaaaag tgccac                              6096

<210> SEQ ID NO 17
<211> LENGTH: 6585
<212> TYPE: DNA
<213> ORGANISM: artificial
<220> FEATURE:
<223> OTHER INFORMATION: vector vEM31
<220> FEATURE:
<221> NAME/KEY: misc_feature
<222> LOCATION: (338)..(1263)
<223> OTHER INFORMATION: Flank1 Del3
<220> FEATURE:
<221> NAME/KEY: gene
<222> LOCATION: (1283)..(1962)
<223> OTHER INFORMATION: Azami green
<220> FEATURE:
<221> NAME/KEY: misc_feature
<222> LOCATION: (2002)..(1963)
<223> OTHER INFORMATION: Ps
<220> FEATURE:
<221> NAME/KEY: misc_feature
<222> LOCATION: (2009)..(2048)
<223> OTHER INFORMATION: Ps
<220> FEATURE:
<221> NAME/KEY: gene
<222> LOCATION: (2049)..(2447)
<223> OTHER INFORMATION: BdsR
<220> FEATURE:
<221> NAME/KEY: promoter
<222> LOCATION: (2454)..(2493)
<223> OTHER INFORMATION: Ps promoter
<220> FEATURE:
<221> NAME/KEY: misc_feature
<222> LOCATION: (2494)..(2524)
<223> OTHER INFORMATION: TetO2
<220> FEATURE:
<221> NAME/KEY: gene
<222> LOCATION: (2535)..(3383)
<223> OTHER INFORMATION: DNAse
<220> FEATURE:
<221> NAME/KEY: promoter
<222> LOCATION: (3390)..(3429)
<223> OTHER INFORMATION: Ps promoter
<220> FEATURE:
<221> NAME/KEY: gene
<222> LOCATION: (3430)..(4086)
<223> OTHER INFORMATION: TetR
<220> FEATURE:
<221> NAME/KEY: misc_feature
<222> LOCATION: (4141)..(4651)
```

<223> OTHER INFORMATION: Flank2 Del3
<220> FEATURE:
<221> NAME/KEY: gene
<222> LOCATION: (5600)..(6457)
<223> OTHER INFORMATION: AmpR

<400> SEQUENCE: 17

| | | | | | |
|---|---|---|---|---|---|
| ctaaattgta | agcgttaata | ttttgttaaa | attcgcgtta | aattttttgtt | aaatcagctc | 60 |
| attttttaac | cataggccg | aaatcggcaa | aatcccttat | aaatcaaaag | aatagaccga | 120 |
| gatagggttg | agtgttgttc | cagtttggaa | caagagtcca | ctattaaaga | acgtggactc | 180 |
| caacgtcaaa | gggcgaaaaa | ccgtctatca | gggcgatggc | ccactacgtg | aaccatcacc | 240 |
| ctaatcaagt | tttttggggt | cgaggtgccg | taaagcacta | aatcggaacc | ctaaagggag | 300 |
| cccccgattt | agagcttgac | ggggaaccac | tatttagttg | gtggtcgcca | tggatggtgt | 360 |
| tattgtatac | tgtctaaacg | cgttagtaaa | acatggcgag | gaaataaatc | atataaaaaa | 420 |
| tgatttcatg | attaaaccat | gttgtgaaaa | agtcaagaac | gttcacattg | gcggacaatc | 480 |
| taaaaacaat | acagtgattg | cagatttgcc | atatatggat | aatgcggtat | ccgatgtatg | 540 |
| caattcactg | tataaaaaga | atgtatcaag | aatatccaga | tttgctaatt | tgataaagat | 600 |
| agatgacgat | gacaagactc | ctactggtgt | atataattat | ttaaaccta | aagatgccat | 660 |
| tcctgttatt | atatccatag | gaaaggatag | agatgtttgt | gaactattaa | tctcatctga | 720 |
| taaagcgtgt | gcgtgtatag | agttaaattc | atataaagta | gccattcttc | ccatggatgt | 780 |
| ttccttttt | accaaggaa | atgcatcatt | gattattctc | ctgtttgatt | tctctatcga | 840 |
| tgcggcacct | ctcttaagaa | gtgtaaccga | taataatgtt | attatatcta | gacaccagcg | 900 |
| tctacatgac | gagcttccga | gttccaattg | gttcaagttt | tacataagta | taaagtccga | 960 |
| ctattgttct | atattatata | tggttgttga | tggatctgtg | atgcatgcaa | tagctgataa | 1020 |
| tagaacttac | gcaaatatta | gcaaaaatat | attagacaat | actacaatta | acgatgagtg | 1080 |
| tagatgctgt | tattttgaac | cacagattag | gattcttgat | agagatgaga | tgctcaatgg | 1140 |
| atcatcgtgt | gatatgaaca | gacattgtat | tatgatgaat | ttacctgatg | taggcgaatt | 1200 |
| tggatctagt | atgttgggga | aatatgaacc | tgacatgatt | aagattgctc | tttcggtggc | 1260 |
| tggcacatcg | gtggcggccg | cttacttggc | ctgactcggc | agcatagaat | agcgagcaac | 1320 |
| ggcattctca | tagagcttga | ccttgttgta | atctttgtca | tgcttcaaaa | tctcaatgcg | 1380 |
| gtggtccaca | aagtgatagt | ctggcaaacg | gacatccttc | tttgctttgt | aagtagtttt | 1440 |
| gaaatcacat | cgataatggc | cacctccttc | aagcaacaga | gccatgttaa | catcaccctt | 1500 |
| cagcactcca | tcacgtacgt | acattttctc | agtggatggc | tcccatttaa | gagtcttctt | 1560 |
| ctgcataacc | ggaccattgg | gaggaaagtt | cacaccatca | aaacgaatgt | catagaaaaa | 1620 |
| acagtcgccc | ctcatgctta | tgttgcttgt | ggcggtgcaa | atgccctggt | cttcataagt | 1680 |
| catgcttctt | tcccagtgat | acccctcagg | aaaagtctgc | ttgaaatagt | cctgaatatc | 1740 |
| tgctgggtac | ttggtgaatg | ccctgttgcc | gtactggaac | actgttgtca | agatatcgta | 1800 |
| agcgaaaggc | agaggtgcgc | cttcagtgac | gttcaggtct | aaaatctgcg | ttccctcgta | 1860 |
| aggatttcct | tttccttctc | cttcaatcac | gaaattatgc | ccgtttacag | tgcctctcat | 1920 |
| acacagcttg | atcttcatct | ctggtttaat | cacactcacc | attatttata | ttccaaaaaa | 1980 |
| aaaaaataaa | atttcaattt | tgccggcaa | aaattgaaat | tttattttt | tttttttggaa | 2040 |
| tataaataat | ggccaagcct | ttgtctcaag | aagaatccac | cctcattgaa | agagcaacgg | 2100 |
| ctacaatcaa | cagcatcccc | atctctgaag | actacagcgt | cgccagcgca | gctctctcta | 2160 |

```
gcgacggccg catcttcact ggtgtcaatg tatatcattt tactggggga ccttgtgcag   2220
aactcgtggt gctgggcact gctgctgctg cggcagctgg caacctgact tgtatcgtcg   2280
cgatcggaaa tgagaacagg ggcatcttga gccctgcgg acggtgccga caggtgcttc    2340
tcgatctgca tcctgggatc aaagccatag tgaaggacag tgatggacag ccgacggcag   2400
ttgggattcg tgaattgctg ccctctggtt atgtgtggga gggctaaact agtaaaaatt   2460
gaaattttat ttttttttt tggaatataa atatccctat cagtgataga gatctcccta    2520
tcagtgatag agatatgagg ggcatgaagc tgctgggggc gctgctggca ctggcggccc   2580
tactgcaggg ggccgtgtcc ctgaagatcg cagccttcaa catccagaca tttggggaga   2640
ccaagatgtc caatgccacc ctcgtcagct acattgtgca gatcctgagc cgctatgaca   2700
tcgccctggt ccaggaggtc agagacagcc acctgactgc cgtggggaag ctgctggaca   2760
acctcaatca ggatgcacca gacacctatc actacgtggt cagtgagcca ctgggacgga   2820
acagctataa ggagcgctac ctgttcgtgt acaggcctga ccaggtgtct gcggtggaca   2880
gctactacta cgatgatggc tgcgagccct gcgggaacga caccttcaac cgagagccag   2940
ccattgtcag gttcttctcc cggttcacag aggtcaggga gtttgccatt gttccctgc    3000 atgcggcccc gggggacgca gtagccgaga tcgacgctct ctatgacgtc tacctggatg   3060
tccaagagaa atggggcttg gaggacgtca tgttgatggg cgacttcaat gcggctgca    3120 gctatgtgag accctcccag tggtcatcca tccgcctgtg gacaagcccc accttccagt   3180
ggctgatccc cgacagcgct gacaccacag ctacacccac gcactgtgcc tatgacagga   3240
tcgtggttgc agggatgctg ctccgaggcg ccgttgttcc cgactcggct cttcccttta   3300
acttccaggc tgcctatggc ctgagtgacc aactggccca agccatcagt gaccactatc   3360
cagtggaggt gatgctgaag taggagctca aaaattgaaa ttttattttt tttttttgga   3420
atataaataa tgtctagatt agataaaagt aaagtgatta acagcgcatt agagctgctt   3480
aatgaggtcg gaatcgaagg tttaacaacc cgtaaactcg cccagaagct aggtgtagag   3540
cagcctacat tgtattggca tgtaaaaaat aagcgggctt tgctcgacgc cttagccatt   3600
gagatgttag ataggcacca tactcacttt tgccctttag aaggggaaag ctggcaagat   3660 ttttacgta ataacgctaa aagttttaga tgtgctttac taagtcatcg cgatggagca    3720
aaagtacatt taggtacacg gcctacagaa aaacagtatg aaactctcga aaatcaatta   3780 gccttttat gccaacaagg ttttttcacta gagaatgcat tatatgcact cagcgctgtg   3840
gggcatttta cttaggttg cgtattggaa gatcaagagc atcaagtcgc taaagaagaa    3900
agggaaacac ctactactga tagtatgccg ccattattac gacaagctat cgaattattt   3960
gatcaccaag gtgcagagcc agccttctta ttcggccttg aattgatcat atgcggatta   4020
gaaaaacaac ttaaatgtga aagtgggtcc gcgtacagcg gatcccggga attcagatct   4080
tattaagcta gcgaattcga tatcaagctt atcgataccg tcgacctcga ggggggccc    4140 ggaaagtttt ataggtagtt gatagaacaa atacataat tttgtaaaaa taaatcactt    4200
tttatactaa tatgacacga ttaccaatac ttttgttact aatatcatta gtatacgcta   4260
caccttttcc tcagacatct aaaaaaatag gtgatgatgc aactttatca tgtaatcgaa   4320
ataatacaaa tgactacgtt gttatgagtg cttggtataa ggagcccaat tccattattc   4380
ttttagctgc taaaagcgac gtcttgtatt ttgataatta taccaaggat aaaatatctt   4440
acgactctcc atacgatgat ctagttacaa ctatcacaat taaatcattg actgctagag   4500
atgccggtac ttatgtatgt gcattcttta tgacatcgcc tacaaatgac actgataaag   4560
```

```
tagattatga agaatactcc acagagttga ttgtaaatac agatagtgaa tcgactatag    4620
acataatact atctggatct acacattcac cggaaactag gcttcctcg ctcactgact    4680 cgctgcgctc ggtcgttcgg ctgcggcgag cggtatcagc tcactcaaag gcggtaatac    4740
ggttatccac agaatcaggg gataacgcag gaaagaacat gtgagcaaaa ggccagcaaa    4800
aggccaggaa ccgtaaaaag gccgcgttgc tggcgttttt ccataggctc cgcccccctg    4860
acgagcatca caaaaatcga cgctcaagtc agaggtggcg aaacccgaca ggactataaa    4920
gataccaggc gtttccccct ggaagctccc tcgtgcgctc tcctgttccg accctgccgc    4980
ttaccggata cctgtccgcc tttctccctt cgggaagcgt ggcgctttct catagctcac    5040
gctgtaggta tctcagttcg gtgtaggtcg ttcgctccaa gctgggctgt gtgcacgaac    5100
cccccgttca gcccgaccgc tgcgccttat ccggtaacta tcgtcttgag tccaacccgg    5160
taagacacga cttatcgcca ctggcagcag ccactggtaa caggattagc agagcgaggt    5220
atgtaggcgg tgctacagag ttcttgaagt ggtggcctaa ctacggctac actagaagga    5280
cagtatttgg tatctgcgct ctgctgaagc cagttacctt cggaaaaaga gttggtagct    5340
cttgatccgg caaacaaacc accgctggta gcggtggttt ttttgtttgc aagcagcaga    5400
ttacgcgcag aaaaaaagga tctcaagaag atcctttgat cttttctacg ggtctgacg    5460 ctcagtggaa cgaaaactca cgttaaggga ttttggtcat gagattatca aaaaggatct    5520
tcacctagat ccttttaaat taaaaatgaa gttttaaatc aatctaaagt atatatgagt    5580
aaacttggtc tgacagttac caatgcttaa tcagtgaggc acctatctca gcgatctgtc    5640
tatttcgttc atccatagtt gcctgactcc ccgtcgtgta gataactacg atacgggagg    5700
gcttaccatc tggccccagt gctgcaatga taccgcgaga cccacgctca ccggctccag    5760
atttatcagc aataaaccag ccagccggaa gggccgagcg cagaagtggt cctgcaactt    5820
tatccgcctc catccagtct attaattgtt gccgggaagc tagagtaagt agttcgccag    5880
ttaatagttt gcgcaacgtt gttgccattg ctacaggcat cgtggtgtca cgctcgtcgt    5940
ttggtatggc ttcattcagc tccggttccc aacgatcaag gcgagttaca tgatccccca    6000
tgttgtgcaa aaaagcggtt agctccttcg gtcctccgat cgttgtcaga agtaagttgg    6060
ccgcagtgtt atcactcatg gttatggcag cactgcataa ttctcttact gtcatgccat    6120
ccgtaagatg cttttctgtg actggtgagt actcaaccaa gtcattctga gaatagtgta    6180
tgcggcgacc gagttgctct tgcccggcgt caatacggga taataccgcg ccacatagca    6240
gaactttaaa agtgctcatc attggaaaac gttcttcggg gcgaaaactc tcaaggatct    6300
taccgctgtt gagatccagt tcgatgtaac ccactcgtgc acccaactga tcttcagcat    6360
cttttacttt caccagcgtt tctgggtgag caaaaacagg aaggcaaaat gccgcaaaaa    6420
agggaataag ggcgacacgg aaatgttgaa tactcatact cttcctttt caatattatt    6480 gaagcattta tcagggttat tgtctcatga gcggatacat atttgaatgt atttagaaaa    6540
ataaacaaat aggggttccg cgcacatttc cccgaaaagt gccac    6585
```

```
<210> SEQ ID NO 18
<211> LENGTH: 3014
<212> TYPE: DNA
<213> ORGANISM: artificial
<220> FEATURE:
<223> OTHER INFORMATION: plasmid
<220> FEATURE:
<221> NAME/KEY: promoter
<222> LOCATION: (622)..(642)
<223> OTHER INFORMATION: T7 promoter
<220> FEATURE:
```

-continued

```
<221> NAME/KEY: misc_feature
<222> LOCATION: (680)..(742)
<223> OTHER INFORMATION: p7.5
<220> FEATURE:
<221> NAME/KEY: promoter
<222> LOCATION: (824)..(844)
<223> OTHER INFORMATION: T3 promoter
<220> FEATURE:
<221> NAME/KEY: promoter
<222> LOCATION: (870)..(991)
<223> OTHER INFORMATION: lac promoter
<220> FEATURE:
<221> NAME/KEY: gene
<222> LOCATION: (2029)..(2886)
<223> OTHER INFORMATION: AmpR

<400> SEQUENCE: 18
```

| | | |
|---|---|---|
| ctaaattgta agcgttaata ttttgttaaa attcgcgtta aatttttgtt aaatcagctc | 60 |
| attttttaac caataggccg aaatcggcaa atcccttat aaatcaaaag aatagaccga | 120 |
| gatagggttg agtgttgttc cagtttggaa caagagtcca ctattaaaga acgtggactc | 180 |
| caacgtcaaa gggcgaaaaa ccgtctatca gggcgatggc ccactacgtg aaccatcacc | 240 |
| ctaatcaagt tttttggggt cgaggtgccg taaagcacta atcggaacc ctaaagggag | 300 |
| cccccgattt agagcttgac ggggaaagcc ggcgaacgtg gcgagaaagg aagggaagaa | 360 |
| agcgaaagga gcgggcgcta gggcgctggc aagtgtagcg gtcacgctgc gcgtaaccac | 420 |
| cacacccgcc gcgcttaatg cgccgctaca gggcgcgtcc cattcgccat tcaggctgcg | 480 |
| caactgttgg aagggcgat cggtgcgggc ctcttcgcta ttacgccagc tggcgaaagg | 540 |
| gggatgtgct gcaaggcgat taagttgggt aacgccaggg ttttcccagt cacgacgttg | 600 |
| taaaacgacg gccagtgaat tgtaatacga ctcactatag gcgaattgg agctccaccg | 660 |
| cggtggcggc cgctctagaa taataataa atacaataat taatttctcg taaaagtaga | 720 |
| aaatatattc taatttattg caggatcccc cgggctgcag gaattcgata tcaagcttat | 780 |
| cgataccgtc gacctcgagg gggggcccgg taccagcttt tgttccctt agtgagggtt | 840 |
| aatttcgagc ttggcgtaat catggtcata gctgtttcct gtgtgaaatt gttatccgct | 900 |
| cacaattcca cacaacatac gagccggaag cataaagtgt aaagcctggg gtgcctaatg | 960 |
| agtgagctaa ctcacattaa ttgcgttgcg ctcactgccc gctttccagt cgggaaacct | 1020 |
| gtcgtgccag ctgcattaat gaatcggcca acgcgcgggg agaggcggtt tgcgtattgg | 1080 |
| gcgctcttcc gcttcctcgc tcactgactc gctgcgctcg tcgttcggc tgcggcgagc | 1140 |
| ggtatcagct cactcaaagg cggtaatacg gttatccaca gaatcagggg ataacgcagg | 1200 |
| aaagaacatg tgagcaaaag gccagcaaaa ggccaggaac cgtaaaaagg ccgcgttgct | 1260 |
| ggcgtttttc cataggctcc gccccctga cgagcatcac aaaaatcgac gctcaagtca | 1320 |
| gaggtggcga aacccgacag gactataaag ataccaggcg tttccccctg gaagctccct | 1380 |
| cgtgcgctct cctgttccga ccctgccgct taccggatac ctgtccgcct ttctcccttc | 1440 |
| gggaagcgtg gcgctttctc atagctcacg ctgtaggtat ctcagttcgg tgtaggtcgt | 1500 |
| tcgctccaag ctgggctgtg tgcacgaacc ccccgttcag cccgaccgct gcgccttatc | 1560 |
| cggtaactat cgtcttgagt ccaacccggt aagacacgac ttatcgccac tggcagcagc | 1620 |
| cactggtaac aggattagca gagcgaggta tgtaggcggt gctacagagt tcttgaagtg | 1680 |
| gtggcctaac tacggctaca ctagaaggac agtatttggt atctgcgctc tgctgaagcc | 1740 |
| agttaccttc ggaaaaagag ttggtagctc ttgatccggc aaacaaacca ccgctggtag | 1800 |
| cggtggtttt tttgtttgca agcagcagat tacgcgcaga aaaaaaggat ctcaagaaga | 1860 |

```
tcctttgatc ttttctacgg ggtctgacgc tcagtggaac gaaaactcac gttaagggat    1920
tttggtcatg agattatcaa aaaggatctt cacctagatc cttttaaatt aaaaatgaag    1980
ttttaaatca atctaaagta tatatgagta aacttggtct gacagttacc aatgcttaat    2040
cagtgaggca cctatctcag cgatctgtct atttcgttca tccatagttg cctgactccc    2100
cgtcgtgtag ataactacga tacgggaggg cttaccatct ggccccagtg ctgcaatgat    2160
accgcgagac ccacgctcac cggctccaga tttatcagca ataaaccagc cagccggaag    2220
ggccgagcgc agaagtggtc ctgcaacttt atccgcctcc atccagtcta ttaattgttg    2280
ccgggaagct agagtaagta gttcgccagt taatagtttg cgcaacgttg ttgccattgc    2340
tacaggcatc gtggtgtcac gctcgtcgtt tggtatggct tcattcagct ccggttccca    2400
acgatcaagg cgagttacat gatcccccat gttgtgcaaa aaagcggtta gctccttcgg    2460
tcctccgatc gttgtcagaa gtaagttggc cgcagtgtta tcactcatgg ttatggcagc    2520
actgcataat tctcttactg tcatgccatc cgtaagatgc ttttctgtga ctggtgagta    2580
ctcaaccaag tcattctgag aatagtgtat gcggcgaccg agttgctctt gcccggcgtc    2640
aatacgggat aataccgcgc cacatagcag aactttaaaa gtgctcatca ttggaaaacg    2700
ttcttcgggg cgaaaactct caaggatctt accgctgttg agatccagtt cgatgtaacc    2760
cactcgtgca cccaactgat cttcagcatc ttttactttc accagcgttt ctgggtgagc    2820
aaaaacagga aggcaaaatg ccgcaaaaaa gggaataagg gcgacacgga aatgttgaat    2880
actcatactc ttcctttttc aatattattg aagcatttat cagggttatt gtctcatgag    2940
cggatacata tttgaatgta tttagaaaaa taaacaaata ggggttccgc gcacatttcc    3000
ccgaaaagtg ccac                                                      3014

<210> SEQ ID NO 19
<211> LENGTH: 3024
<212> TYPE: DNA
<213> ORGANISM: artificial
<220> FEATURE:
<223> OTHER INFORMATION: plasmid
<220> FEATURE:
<221> NAME/KEY: promoter
<222> LOCATION: (625)..(645)
<223> OTHER INFORMATION: T7 promoter
<220> FEATURE:
<221> NAME/KEY: promoter
<222> LOCATION: (683)..(752)
<223> OTHER INFORMATION: H5 promoter
<220> FEATURE:
<221> NAME/KEY: promoter
<222> LOCATION: (834)..(854)
<223> OTHER INFORMATION: T3 promoter
<220> FEATURE:
<221> NAME/KEY: promoter
<222> LOCATION: (880)..(1001)
<223> OTHER INFORMATION: lac promoter
<220> FEATURE:
<221> NAME/KEY: gene
<222> LOCATION: (2039)..(2896)
<223> OTHER INFORMATION: AmpR

<400> SEQUENCE: 19
ctaaattgta agcgttaata ttttgttaaa attcgcgtta aattttgtt aaatcagctc      60 attttttaac caataggccg aaatcggcaa aatcccttat aaatcaaaag aatagaccga    120
gatagggttg agtgttgttc cagtttggaa caagagtcca ctattaaaga acgtggactc    180
caacgtcaaa gggcgaaaaa ccgtctatca gggcgatggc ccactacgtg aaccatcacc    240
ctaatcaagt ttttttgggt cgaggtgccg taaagcacta aatcggaacc ctaaagggag    300
```

```
cccccgattt agagcttgac ggggaaagcc ggcgaacgtg gcgagaaagg aagggaagaa      360
agcgaaagga gcgggcgcta gggcgctggc aagtgtagcg gtcacgctgc gcgtaaccac      420
cacacccgcc gcgcttaatg cgccgctaca gggcgcgtcc cattcgccat tcaggctgcg      480
caactgttgg gaagggcgat cggtgcgggc ctcttcgcta ttacgccagc tggcgaaagg      540
gggatgtgct gcaaggcgat taagttgggt aacgccaggg ttttcccagt cacgacgttg      600
taaaacgacg gccagtgagc gcgcgtaata cgactcacta tagggcgaat ggagctcca       660 ccgcggtggc ggccgctcta gaaaaaatg aaaataaata caaggttct tgagggttgt       720 gttaaattga aagcgagaaa taatcataaa ttggatcccc cgggctgcag gaattcgata      780
tcaagcttat cgataccgtc gacctcgagg ggggcccgg taccagcttt tgttcccttt       840
agtgagggtt aatttcgagc ttggcgtaat catggtcata gctgtttcct gtgtgaaatt      900
gttatccgct cacaattcca cacacatac gagccggaag cataaagtgt aaagcctggg       960
gtgcctaatg agtgagctaa ctcacattaa ttgcgttgcg ctcactgccc gctttccagt     1020
cgggaaacct gtcgtgccag ctgcattaat gaatcggcca acgcgcgggg agaggcggtt     1080
tgcgtattgg gcgctcttcc gcttcctcgc tcactgactc gctgcgctcg tcgttcggc      1140 tgcggcgagc ggtatcagct cactcaaagg cggtaatacg ttatccaca gaatcagggg      1200 ataacgcagg aaagaacatg tgagcaaaag gccagcaaaa ggccaggaac cgtaaaaagg     1260
ccgcgttgct ggcgtttttc cataggctcc gcccccctga cgagcatcac aaaaatcgac     1320
gctcaagtca gaggtggcga aacccgacag gactataaag ataccaggcg tttccccctg     1380
gaagctccct cgtgcgctct cctgttccga ccctgccgct taccggatac ctgtccgcct     1440
ttctcccttc gggaagcgtg gcgctttctc atagctcacg ctgtaggtat ctcagttcgg     1500
tgtaggtcgt tcgctccaag ctgggctgtg tgcacgaacc ccccgttcag cccgaccgct     1560
gcgccttatc cggtaactat cgtcttgagt ccaacccgt aagacacgac ttatcgccac      1620
tggcagcagc cactggtaac aggattagca gagcgaggta tgtaggcggt gctacagagt     1680
tcttgaagtg gtggcctaac tacggctaca ctagaaggac agtatttggt atctgcgctc     1740
tgctgaagcc agttaccttc ggaaaaagag ttggtagctc ttgatccggc aaacaaacca     1800
ccgctggtag cggtggtttt tttgtttgca agcagcagat tacgcgcaga aaaaaggat      1860 ctcaagaaga tcctttgatc ttttctacgg ggtctgacgc tcagtggaac gaaaactcac     1920
gttaagggat tttggtcatg agattatcaa aaaggatctt cacctagatc cttttaaatt     1980
aaaaatgaag ttttaaatca atctaaagta tatatgagta aacttggtct gacagttacc     2040
aatgcttaat cagtgaggca cctatctcag cgatctgtct atttcgttca tccatagttg     2100
cctgactccc cgtcgtgtag ataactacga tacgggaggg cttaccatct ggccccagtg     2160
ctgcaatgat accgcgagac ccacgctcac cggctccaga tttatcagca ataaaccagc     2220
cagccggaag ggccgagcgc agaagtggtc ctgcaacttt atccgcctcc atccagtcta     2280
ttaattgttg ccgggaagct agagtaagta gttcgccagt taatagtttg cgcaacgttg     2340
ttgccattgc tacaggcatc gtggtgtcac gctcgtcgtt tggtatggct tcattcagct     2400
ccggttccca acgatcaagg cgagttacat gatcccccat gttgtgcaaa aaagcggtta     2460
gctccttcgg tcctccgatc gttgtcagaa gtaagttggc cgcagtgtta tcactcatgg     2520
ttatggcagc actgcataat tctcttactg tcatgccatc cgtaagatgc ttttctgtga     2580
ctggtgagta ctcaaccaag tcattctgag aatagtgtat gcggcgaccg agttgctctt     2640
gcccggcgtc aatacgggat aataccgcgc cacatagcag aactttaaaa gtgctcatca     2700
```

-continued

| | | |
|---|---|---|
| ttggaaaacg ttcttcgggg cgaaaactct caaggatctt accgctgttg agatccagtt | 2760 | |
| cgatgtaacc cactcgtgca cccaactgat cttcagcatc ttttactttc accagcgttt | 2820 | |
| ctgggtgagc aaaaacagga aggcaaaatg ccgcaaaaaa gggaataagg gcgacacgga | 2880 | |
| aatgttgaat actcatactc ttccttttc aatattattg aagcatttat cagggttatt | 2940 | |
| gtctcatgag cggatacata tttgaatgta tttagaaaaa taaacaaata ggggttccgc | 3000 | |
| gcacatttcc ccgaaaagtg ccac | 3024 | |

<210> SEQ ID NO 20
<211> LENGTH: 3667
<212> TYPE: DNA
<213> ORGANISM: artificial
<220> FEATURE:
<223> OTHER INFORMATION: vector pEM12 (7.5)
<220> FEATURE:
<221> NAME/KEY: promoter
<222> LOCATION: (622)..(642)
<223> OTHER INFORMATION: T7 promoter
<220> FEATURE:
<221> NAME/KEY: misc_feature
<222> LOCATION: (680)..(742)
<223> OTHER INFORMATION: p7.5
<220> FEATURE:
<221> NAME/KEY: gene
<222> LOCATION: (799)..(1455)
<223> OTHER INFORMATION: TetR
<220> FEATURE:
<221> NAME/KEY: promoter
<222> LOCATION: (1477)..(1497)
<223> OTHER INFORMATION: T3 promoter
<220> FEATURE:
<221> NAME/KEY: promoter
<222> LOCATION: (1523)..(1644)
<223> OTHER INFORMATION: lac promoter
<220> FEATURE:
<221> NAME/KEY: gene
<222> LOCATION: (2682)..(3539)
<223> OTHER INFORMATION: AmpR

<400> SEQUENCE: 20

| | | |
|---|---|---|
| ctaaattgta agcgttaata ttttgttaaa attcgcgtta aatttttgtt aaatcagctc | 60 | |
| attttttaac caataggccg aaatcggcaa aatcccttat aaatcaaaag aatagaccga | 120 | |
| gatagggttg agtgttgttc cagtttggaa caagagtcca ctattaaaga acgtggactc | 180 | |
| caacgtcaaa gggcgaaaaa ccgtctatca gggcgatggc ccactacgtg aaccatcacc | 240 | |
| ctaatcaagt tttttggggt cgaggtgccg taaagcacta atcggaacc ctaaagggag | 300 | |
| cccccgattt agagcttgac ggggaaagcc ggcgaacgtg gcgagaaagg aagggaagaa | 360 | |
| agcgaaagga gcgggcgcta gggcgctggc aagtgtagcg gtcacgctgc gcgtaaccac | 420 | |
| cacacccgcc gcgcttaatg cgccgctaca gggcgcgtcc cattcgccat tcaggctgcg | 480 | |
| caactgttgg gaagggcgat cggtgcgggc ctcttcgcta ttacgccagc tggcgaaagg | 540 | |
| gggatgtgct gcaaggcgat taagttgggt aacgccaggg ttttcccagt cacgacgttg | 600 | |
| taaaacgacg gccagtgaat tgtaatacga ctcactatag ggcgaattgg agctccaccg | 660 | |
| cggtggcggc cgctctagaa taataataa atacaataat taattctcg taaaagtaga | 720 | |
| aaatatattc taatttattg caggatcccc cgggctgcag gaattcgata tcaagcttat | 780 | |
| cgataccgtc gacccgagat gtctagatta gataaaagta aagtgattaa cagcgcatta | 840 | |
| gagctgctta atgaggtcgg aatcgaaggt ttaacaaccc gtaaactcgc ccagaagcta | 900 | |
| ggtgtagagc agcctacatt gtattggcat gtaaaaaata gcgggcttt gctcgacgcc | 960 | |
| ttagccattg agatgttaga taggcaccat actcactttt gccctttaga aggggaaagc | 1020 | |

```
tggcaagatt ttttacgtaa taacgctaaa agttttagat gtgctttact aagtcatcgc    1080
gatggagcaa aagtacattt aggtacacgg cctacagaaa aacagtatga aactctcgaa    1140
aatcaattag ccttttttatg ccaacaaggt ttttcactag agaatgcatt atatgcactc    1200
agcgctgtgg ggcattttac tttaggttgc gtattggaag atcaagagca tcaagtcgct    1260
aaagaagaaa gggaaacacc tactactgat agtatgccgc cattattacg acaagctatc    1320
gaattatttg atcaccaagg tgcagagcca gccttcttat tcggccttga attgatcata    1380
tgcggattag aaaaacaact aaatgtgaa agtgggtccg cgtacagcgg atcccgggaa    1440
ttcagatctt attaagggcc cggtaccagc ttttgttccc tttagtgagg gttaatttcg    1500
agcttggcgt aatcatggtc atagctgttt cctgtgtgaa attgttatcc gctcacaatt    1560
ccacacaaca tacgagccgg aagcataaag tgtaaagcct ggggtgccta atgagtgagc    1620
taactcacat taattgcgtt gcgctcactg cccgctttcc agtcgggaaa cctgtcgtgc    1680
cagctgcatt aatgaatcgg ccaacgcgcg ggagaggcg gtttgcgtat tgggcgctct    1740
tccgcttcct cgctcactga ctcgctgcgc tcggtcgttc ggctgcggcg agcggtatca    1800
gctcactcaa aggcggtaat acggttatcc acagaatcag gggataacgc aggaaagaac    1860
atgtgagcaa aaggccagca aaaggccagg aaccgtaaaa aggccgcgtt gctggcgttt    1920
ttccataggc tccgcccccc tgacgagcat cacaaaaatc gacgctcaag tcagaggtgg    1980
cgaaacccga caggactata aagataccag gcgtttcccc ctggaagctc cctcgtgcgc    2040
tctcctgttc cgaccctgcc gcttaccgga tacctgtccg cctttctccc ttcgggaagc    2100
gtggcgcttt ctcatagctc acgctgtagg tatctcagtt cggtgtaggt cgttcgctcc    2160
aagctgggct gtgtgcacga accccccgtt cagcccgacc gctgcgcctt atccggtaac    2220
tatcgtcttg agtccaaccc ggtaagacac gacttatcgc cactggcagc agccactggt    2280
aacaggatta gcagagcgag gtatgtaggc ggtgctacag agttcttgaa gtggtggcct    2340
aactacggct acactagaag gacagtattt ggtatctgcg ctctgctgaa gccagttacc    2400
ttcggaaaaa gagttggtag ctcttgatcc ggcaaacaaa ccaccgctgg tagcggtggt    2460
ttttttgttt gcaagcagca gattacgcgc agaaaaaaag gatctcaaga agatcctttg    2520
atcttttcta cggggtctga cgctcagtgg aacgaaaact cacgttaagg gattttggtc    2580
atgagattat caaaaaggat cttcacctag atccttttaa attaaaaatg aagttttaaa    2640
tcaatctaaa gtatatatga gtaaacttgg tctgacagtt accaatgctt aatcagtgag    2700
gcacctatct cagcgatctg tctatttcgt tcatccatag ttgcctgact ccccgtcgtg    2760
tagataacta cgatacggga gggcttacca tctggcccca gtgctgcaat gataccgcga    2820
gacccacgct caccggctcc agatttatca gcaataaacc agccagccgg aagggccgag    2880
cgcagaagtg gtcctgcaac tttatccgcc tccatccagt ctattaattg ttgccgggaa    2940
gctagagtaa gtagttcgcc agttaatagt ttgcgcaacg ttgttgccat tgctacaggc    3000
atcgtggtgt cacgctcgtc gtttggtatg gcttcattca gctccggttc ccaacgatca    3060
aggcgagtta catgatcccc catgttgtgc aaaaaagcgg ttagctcctt cggtcctccg    3120
atcgttgtca gaagtaagtt ggccgcagtg ttatcactca tggttatggc agcactgcat    3180
aattctctta ctgtcatgcc atccgtaaga tgcttttctg tgactggtga gtactcaacc    3240
aagtcattct gagaatagtg tatgcggcga ccgagttgct cttgcccggc gtcaatacgg    3300
gataataccg cgccacatag cagaacttta aaagtgctca tcattggaaa acgttcttcg    3360
gggcgaaaac tctcaaggat cttaccgctg ttgagatcca gttcgatgta acccactcgt    3420
```

-continued

```
gcacccaact gatcttcagc atctttcact ttcaccagcg tttctgggtg agcaaaaaca     3480
ggaaggcaaa atgccgcaaa aaagggaata agggcgacac ggaaatgttg aatactcata     3540
ctcttccttt ttcaatatta ttgaagcatt tatcagggtt attgtctcat gagcggatac     3600
atatttgaat gtatttagaa aaataaacaa atagggggttc cgcgcacatt tccccgaaaa     3660
gtgccac                                                               3667

<210> SEQ ID NO 21
<211> LENGTH: 3695
<212> TYPE: DNA
<213> ORGANISM: artificial
<220> FEATURE:
<223> OTHER INFORMATION: vector pEM13 (H5)
<220> FEATURE:
<221> NAME/KEY: promoter
<222> LOCATION: (625)..(645)
<223> OTHER INFORMATION: T7 promoter
<220> FEATURE:
<221> NAME/KEY: promoter
<222> LOCATION: (683)..(752)
<223> OTHER INFORMATION: H5 promoter
<220> FEATURE:
<221> NAME/KEY: gene
<222> LOCATION: (786)..(1442)
<223> OTHER INFORMATION: TetR
<220> FEATURE:
<221> NAME/KEY: promoter
<222> LOCATION: (1505)..(1525)
<223> OTHER INFORMATION: T3 promoter
<220> FEATURE:
<221> NAME/KEY: promoter
<222> LOCATION: (1551)..(1672)
<223> OTHER INFORMATION: lac promoter
<220> FEATURE:
<221> NAME/KEY: gene
<222> LOCATION: (2710)..(3567)
<223> OTHER INFORMATION: AmpR

<400> SEQUENCE: 21
ctaaattgta agcgttaata ttttgttaaa attcgcgtta aatttttgtt aaatcagctc       60
attttttaac caataggccg aaatcggcaa aatcccttat aaatcaaaag aatagaccga      120
gatagggttg agtgttgttc cagtttggaa caagagtcca ctattaaaga acgtggactc      180
caacgtcaaa gggcgaaaaa ccgtctatca gggcgatggc ccactacgtg aaccatcacc      240
ctaatcaagt ttttgggggt cgaggtgccg taaagcacta atcggaacc  ctaaagggag      300 cccccgattt agagcttgac ggggaaagcc ggcgaacgtg gcgagaaagg aagggaagaa      360
agcgaaagga gcgggcgcta gggcgctggc aagtgtagcg gtcacgctgc gcgtaaccac      420
cacacccgcc gcgcttaatg cgccgctaca gggcgcgtcc cattcgccat tcaggctgcg      480
caactgttgg gaagggcgat cggtgcgggc ctcttcgcta ttacgccagc tggcgaaagg      540
gggatgtgct gcaaggcgat taagttgggt aacgccaggg ttttcccagt cacgacgttg      600
taaaacgacg gccagtgagc gcgcgtaata cgactcacta gggcgaat  tggagctcca      660 ccgcggtggc ggccgctcta gaaaaaaatg aaaataaata caaaggttct tgagggttgt      720
gttaaattga agcgagaaa  taatcataaa ttggatcccc cgggctgcag gaattcgatc      780
tcgagatgtc tagattagat aaaagtaaag tgattaacag cgcattagag ctgcttaatg      840
aggtcggaat cgaaggttta acaacccgta aactcgccca aagctaggt gtagagcagc      900 ctacattgta ttggcatgta aaaataagc gggctttgct cgacgcctta gccattgaga     960
tgttagatag gcaccatact cacttttgcc ctttagaagg ggaaagctgg caagattttt     1020
tacgtaataa cgctaaaagt tttagatgtg ctttactaag tcatcgcgat ggagcaaaag     1080
```

```
tacatttagg tacacggcct acagaaaaac agtatgaaac tctcgaaaat caattagcct    1140
ttttatgcca acaaggtttt tcactagaga atgcattata tgcactcagc gctgtggggc    1200
attttacttt aggttgcgta ttggaagatc aagagcatca agtcgctaaa gaagaaaggg    1260
aaacacctac tactgatagt atgccgccat tattacgaca agctatcgaa ttatttgatc    1320
accaaggtgc agagccagcc ttcttattcg gccttgaatt gatcatatgc ggattagaaa    1380
aacaacttaa atgtgaaagt gggtccgcgt acagcggatc ccgggaattc agatcttatt    1440
aagggcccgg atcaagctta tcgataccgt cgacctcgag ggggggcccg gtaccagctt    1500
ttgttccctt tagtgagggt taatttcgag cttggcgtaa tcatggtcat agctgtttcc    1560
tgtgtgaaat tgttatccgc tcacaattcc acacaacata cgagccggaa gcataaagtg    1620
taaagcctgg ggtgcctaat gagtgagcta actcacatta attgcgttgc gctcactgcc    1680
cgctttccag tcgggaaacc tgtcgtgcca gctgcattaa tgaatcggcc aacgcgcggg    1740
gagaggcggt ttgcgtattg ggcgctcttc cgcttcctcg ctcactgact cgctgcgctc    1800
ggtcgttcgg ctgcggcgag cggtatcagc tcactcaaag gcggtaatac ggttatccac    1860
agaatcaggg gataacgcag gaaagaacat gtgagcaaaa ggccagcaaa aggccaggaa    1920
ccgtaaaaag gccgcgttgc tggcgttttt ccataggctc cgcccccctg acgagcatca    1980
caaaaatcga cgctcaagtc agaggtggcg aaacccgaca ggactataaa gataccaggc    2040
gtttccccct ggaagctccc tcgtgcgctc tcctgttccg accctgccgc ttaccggata    2100
cctgtccgcc tttctccctt cgggaagcgt ggcgctttct catagctcac gctgtaggta    2160
tctcagttcg gtgtaggtcg ttcgctccaa gctgggctgt gtgcacgaac cccccgttca    2220
gcccgaccgc tgcgccttat ccggtaacta tcgtcttgag tccaacccgg taagacacga    2280
cttatcgcca ctggcagcag ccactggtaa caggattagc agagcgaggt atgtaggcgg    2340
tgctacagag ttcttgaagt ggtggcctaa ctacggctac actagaagga cagtatttgg    2400
tatctgcgct ctgctgaagc cagttacctt cggaaaaaga gttggtagct cttgatccgg    2460
caaacaaacc accgctggta gcggtggttt ttttgtttgc aagcagcaga ttacgcgcag    2520
aaaaaaagga tctcaagaag atcctttgat cttttctacg gggtctgacg ctcagtggaa    2580
cgaaaactca cgttaaggga ttttggtcat gagattatca aaaaggatct tcacctagat    2640
ccttttaaat taaaaatgaa gttttaaatc aatctaaagt atatatgagt aaacttggtc    2700
tgacagttac caatgcttaa tcagtgaggc acctatctca gcgatctgtc tatttcgttc    2760
atccatagtt gcctgactcc ccgtcgtgta gataactacg atacgggagg gcttaccatc    2820
tggccccagt gctgcaatga taccgcgaga cccacgctca ccggctccag atttatcagc    2880
aataaaccag ccagccggaa gggccgagcg cagaagtggt cctgcaactt tatccgcctc    2940
catccagtct attaattgtt gccgggaagc tagagtaagt agttcgccag ttaatagttt    3000
gcgcaacgtt gttgccattg ctacaggcat cgtggtgtca cgctcgtcgt ttggtatggc    3060
ttcattcagc tccggttccc aacgatcaag gcgagttaca tgatcccccca tgttgtgcaa    3120 aaaagcggtt agctccttcg gtcctccgat cgttgtcaga agtaagttgg ccgcagtgtt    3180
atcactcatg gttatggcag cactgcataa ttctcttact gtcatgccat ccgtaagatg    3240
cttttctgtg actggtgagt actcaaccaa gtcattctga aatagtgta tgcggcgacc    3300 gagttgctct tgcccggcgt caatacggga taataccgcg ccacatagca gaactttaaa    3360
agtgctcatc attggaaaac gttcttcggg gcgaaaactc tcaaggatct taccgctgtt    3420
gagatccagt tcgatgtaac ccactcgtgc acccaactga tcttcagcat cttttacttt    3480
```

-continued

```
caccagcgtt tctgggtgag caaaaacagg aaggcaaaat gccgcaaaaa agggaataag    3540
ggcgacacgg aaatgttgaa tactcatact cttccttttt caatattatt gaagcattta    3600
tcagggttat tgtctcatga gcggatacat atttgaatgt atttagaaaa ataaacaaat    3660
aggggttccg cgcacatttc cccgaaaagt gccac                               3695
```

<210> SEQ ID NO 22
<211> LENGTH: 6640
<212> TYPE: DNA
<213> ORGANISM: artificial
<220> FEATURE:
<223> OTHER INFORMATION: vector vEM32 (7.5)
<220> FEATURE:
<221> NAME/KEY: misc_feature
<222> LOCATION: (338)..(1263)
<223> OTHER INFORMATION: Flank1 Del3
<220> FEATURE:
<221> NAME/KEY: gene
<222> LOCATION: (1283)..(1962)
<223> OTHER INFORMATION: Azami green
<220> FEATURE:
<221> NAME/KEY: misc_feature
<222> LOCATION: (2002)..(1963)
<223> OTHER INFORMATION: Ps
<220> FEATURE:
<221> NAME/KEY: misc_feature
<222> LOCATION: (2009)..(2048)
<223> OTHER INFORMATION: Ps
<220> FEATURE:
<221> NAME/KEY: gene
<222> LOCATION: (2049)..(2447)
<223> OTHER INFORMATION: BsdR
<220> FEATURE:
<221> NAME/KEY: promoter
<222> LOCATION: (2454)..(2493)
<223> OTHER INFORMATION: Ps promoter
<220> FEATURE:
<221> NAME/KEY: misc_feature
<222> LOCATION: (2494)..(2534)
<223> OTHER INFORMATION: TetO2
<220> FEATURE:
<221> NAME/KEY: gene
<222> LOCATION: (2535)..(3383)
<223> OTHER INFORMATION: DNAse
<220> FEATURE:
<221> NAME/KEY: misc_feature
<222> LOCATION: (3414)..(3476)
<223> OTHER INFORMATION: p7.5
<220> FEATURE:
<221> NAME/KEY: gene
<222> LOCATION: (3533)..(4189)
<223> OTHER INFORMATION: TetR
<220> FEATURE:
<221> NAME/KEY: misc_feature
<222> LOCATION: (4196)..(4706)
<223> OTHER INFORMATION: Flank2 Del3
<220> FEATURE:
<221> NAME/KEY: gene
<222> LOCATION: (5655)..(6512)
<223> OTHER INFORMATION: AmpR

<400> SEQUENCE: 22

```
ctaaattgta agcgttaata ttttgttaaa attcgcgtta aatttttgtt aaatcagctc      60 atttttaac caataggccg aaatcggcaa atcccttat aaatcaaaag aatagaccga      120
gatagggttg agtgttgttc cagtttggaa caagagtcca ctattaaaga acgtggactc     180
caacgtcaaa gggcgaaaaa ccgtctatca gggcgatggc ccactacgtg aaccatcacc     240
ctaatcaagt ttttttgggt cgaggtgccg taaagcacta atcggaacc ctaaagggag      300 cccccgattt agagcttgac ggggaaccac tatttagttg gtggtcgcca tggatggtgt     360
tattgtatac tgtctaaacg cgttagtaaa acatggcgag gaaataaatc atataaaaaa     420
```

```
tgatttcatg attaaaccat gttgtgaaaa agtcaagaac gttcacattg gcggacaatc    480
taaaaacaat acagtgattg cagatttgcc atatatggat aatgcggtat ccgatgtatg    540
caattcactg tataaaaaga atgtatcaag aatatccaga tttgctaatt tgataaagat    600
agatgacgat gacaagactc ctactggtgt atataattat tttaaaccta aagatgccat    660
tcctgttatt atatccatag gaaaggatag agatgtttgt gaactattaa tctcatctga    720
taaagcgtgt gcgtgtatag agttaaattc atataaagta gccattcttc ccatggatgt    780 ttccttttt accaaaggaa atgcatcatt gattattctc ctgtttgatt tctctatcga    840
tgcggcacct ctcttaagaa gtgtaaccga taataatgtt attatatcta gacaccagcg    900
tctacatgac gagcttccga gttccaattg gttcaagttt tacataagta taaagtccga    960
ctattgttct atattatata tggttgttga tggatctgtg atgcatgcaa tagctgataa   1020
tagaacttac gcaaatatta gcaaaaatat attagacaat actacaatta acgatgagtg   1080
tagatgctgt tattttgaac cacagattag gattcttgat agagatgaga tgctcaatgg   1140
atcatcgtgt gatatgaaca gacattgtat tatgatgaat ttacctgatg taggcgaatt   1200
tggatctagt atgttgggga aatatgaacc tgacatgatt aagattgctc tttcggtggc   1260
tggcacatcg gtggcggccg cttacttggc ctgactcggc agcatagaat agcgagcaac   1320
ggcattctca tagagcttga ccttgttgta atctttgtca tgcttcaaaa tctcaatgcg   1380
gtggtccaca aagtgatagt ctggcaaacg gacatccttc tttgctttgt aagtagtttt   1440
gaaatcacat cgataatggc cacctccttc aagcaacaga gccatgttaa catcacccett  1500 cagcactcca tcacgtacgt acattttctc agtggatggc tcccatttaa gagtcttctt   1560
ctgcataacc ggaccattgg gaggaaagtt cacaccatca aaacgaatgt catagaaaaa   1620
acagtcgccc ctcatgctta tgttgcttgt ggcggtgcaa atgccctggt cttcataagt   1680
catgcttctt tcccagtgat acccctcagg aaaagtctgc ttgaaatagt cctgaatatc   1740
tgctgggtac ttggtgaatg ccctgttgcc gtactggaac actgttgtca agatatcgta   1800
agcgaaaggc agaggtgcgc cttcagtgac gttcaggtct aaaatctgcg ttccctcgta   1860
aggatttcct tttccttctc cttcaatcac gaaattatgc ccgtttacag tgcctctcat   1920
acacagcttg atcttcatct ctggtttaat cacactcacc attatttata ttccaaaaaa   1980
aaaaaataaa atttcaattt tgccggcaa aaattgaaat tttattttt ttttttggaa    2040 tataaataat ggccaagcct ttgtctcaag aagaatccac cctcattgaa agagcaacgg   2100
ctacaatcaa cagcatcccc atctctgaag actacagcgt cgccagcgca gctctctcta   2160
gcgacggccg catcttcact ggtgtcaatg tatatcattt tactggggga ccttgtgcag   2220
aactcgtggt gctgggcact gctgctgctg cggcagctgg caacctgact tgtatcgtcg   2280
cgatcggaaa tgagaacagg ggcatcttga gcccctgcgg acggtgccga caggtgcttc   2340
tcgatctgca tcctgggatc aaagccatag tgaaggacag tgatgacag ccgacggcag   2400 ttgggattcg tgaattgctg ccctctggtt atgtgtggga gggctaaact agtaaaaatt   2460 gaaatttat ttttttttt tggaatataa atatccctat cagtgataga gatctcccta    2520
tcagtgatag agatatgagg ggcatgaagc tgctggggc gctgctggca ctggcggccc   2580
tactgcaggg ggccgtgtcc ctgaagatcg cagccttcaa catccagaca tttggggaga   2640
ccaagatgtc caatgccacc ctcgtcagct acattgtgca gatcctgagc cgctatgaca   2700
tcgccctggt ccaggaggtc agagacagcc cctgactgc cgtggggaag ctgctggaca   2760
acctcaatca ggatgcacca gacacctatc actacgtggt cagtgagcca ctgggacgga   2820
```

```
acagctataa ggagcgctac ctgttcgtgt acaggcctga ccaggtgtct gcggtggaca    2880
gctactacta cgatgatggc tgcgagccct gcgggaacga caccttcaac cgagagccag    2940
ccattgtcag gttcttctcc cggttcacag aggtcaggga gtttgccatt gttcccctgc    3000
atgcggcccc gggggacgca gtagccgaga tcgacgctct ctatgacgtc tacctggatg    3060
tccaagagaa atgggcttg gaggacgtca tgttgatggg cgacttcaat gcgggctgca    3120
gctatgtgag accctcccag tggtcatcca tccgcctgtg acaagcccc accttccagt    3180 ggctgatccc cgacagcgct gacaccacag ctacacccac gcactgtgcc tatgacagga    3240
tcgtggttgc agggatgctg ctccgaggcg ccgttgttcc cgactcggct cttccctta    3300 acttccaggc tgcctatggc ctgagtgacc aactggccca agccatcagt gaccactatc    3360
cagtggaggt gatgctgaag taggagctcc accgcgtgg cggccgctct agaataaata    3420
ataaatacaa taattaattt ctcgtaaaag tagaaaatat attctaattt attgcaggat    3480
cccccgggct gcaggaattc gatatcaagc ttatcgatac cgtcgacccg agatgtctag    3540
attagataaa agtaaagtga ttaacagcgc attagagctg cttaatgagg tcggaatcga    3600
aggtttaaca acccgtaaac tcgcccagaa gctaggtgta gagcagccta cattgtattg    3660
gcatgtaaaa aataagcggg ctttgctcga cgccttagcc attgagatgt tagataggca    3720
ccatactcac ttttgccctt tagaagggga aagctggcaa gattttttac gtaataacgc    3780
taaaagtttt agatgtgctt tactaagtca tcgcgatgga gcaaaagtac atttaggtac    3840
acggcctaca gaaaaacagt atgaaactct cgaaaatcaa ttagcctttt tatgccaaca    3900 aggttttca ctagagaatg cattatatgc actcagcgct gtggggcatt ttactttagg    3960
ttgcgtattg gaagatcaag agcatcaagt cgctaaagaa gaagggaaa cacctactac    4020 tgatagtatg ccgccattat tacgacaagc tatcgaatta tttgatcacc aaggtgcaga    4080
gccagccttc ttattcggcc ttgaattgat catatgcgga ttagaaaaac aacttaaatg    4140
tgaaagtggg tccgcgtaca gcggatcccg ggaattcaga tcttattaag ggcccggaaa    4200 gtttatagg tagttgatag aacaaaatac ataattttgt aaaaataaat cacttttat    4260 actaatatga cacgattacc aatacttttg ttactaatat cattagtata cgctacacct    4320
tttcctcaga catctaaaaa aataggtgat gatgcaactt tatcatgtaa tcgaaataat    4380
acaaatgact acgttgttat gagtgcttgg tataaggagc ccaattccat tattcttta    4440 gctgctaaaa gcgacgtctt gtattttgat aattatacca aggataaaat atcttacgac    4500
tctccatacg atgatctagt tacaactatc acaattaaat cattgactgc tagagatgcc    4560
ggtacttatg tatgtgcatt ctttatgaca tcgcctacaa atgacactga taaagtagat    4620
tatgaagaat actccacaga gttgattgta aatacagata gtgaatcgac tatagacata    4680
atactatctg gatctacaca ttcaccggaa actagggctt cctcgctcac tgactcgctg    4740
cgctcggtcg ttcggctgcg gcgagcggta tcagctcact caaaggcggt aatacggtta    4800
tccacagaat caggggataa cgcaggaaag aacatgtgag caaaaggcca gcaaaaggcc    4860
aggaaccgta aaaaggccgc gttgctggcg tttttccata ggctccgccc ccctgacgag    4920
catcacaaaa atcgacgctc aagtcagagg tggcgaaacc cgacaggact ataaagatac    4980
caggcgtttc ccctggaag ctccctcgtg cgctctcctg ttccgaccct gccgcttacc    5040
ggatacctgt ccgcctttct cccttcggga agcgtggcgc tttctcatag ctcacgctgt    5100
aggtatctca gttcggtgta ggtcgttcgc tccaagctgg gctgtgtgca cgaaccccc    5160 gttcagcccg accgctgcgc cttatccggt aactatcgtc ttgagtccaa cccggtaaga    5220
```

```
cacgacttat cgccactggc agcagccact ggtaacagga ttagcagagc gaggtatgta    5280
ggcggtgcta cagagttctt gaagtggtgg cctaactacg gctacactag aaggacagta    5340
tttggtatct gcgctctgct gaagccagtt accttcggaa aaagagttgg tagctcttga    5400
tccggcaaac aaaccaccgc tggtagcggt ggttttttg  tttgcaagca gcagattacg    5460
cgcagaaaaa aaggatctca agaagatcct ttgatctttt ctacggggtc tgacgctcag    5520
tggaacgaaa actcacgtta agggattttg gtcatgagat tatcaaaaag gatcttcacc    5580
tagatccttt taaattaaaa atgaagtttt aaatcaatct aaagtatata tgagtaaact    5640
tggtctgaca gttaccaatg cttaatcagt gaggcaccta tctcagcgat ctgtctattt    5700
cgttcatcca tagttgcctg actccccgtc gtgtagataa ctacgatacg ggagggctta    5760
ccatctggcc ccagtgctgc aatgataccg cgagacccac gctcaccggc tccagattta    5820
tcagcaataa accagccagc cggaagggcc gagcgcagaa gtggtcctgc aactttatcc    5880
gcctccatcc agtctattaa ttgttgccgg gaagctagag taagtagttc gccagttaat    5940
agtttgcgca acgttgttgc cattgctaca ggcatcgtgg tgtcacgctc gtcgtttggt    6000
atggcttcat tcagctccgg ttcccaacga tcaaggcgag ttacatgatc ccccatgttg    6060
tgcaaaaaag cggttagctc cttcggtcct ccgatcgttg tcagaagtaa gttggccgca    6120
gtgttatcac tcatggttat ggcagcactg cataattctc ttactgtcat gccatccgta    6180
agatgctttt ctgtgactgg tgagtactca accaagtcat tctgagaata gtgtatgcgg    6240
cgaccgagtt gctcttgccc ggcgtcaata cgggataata ccgcgccaca tagcagaact    6300
ttaaaagtgc tcatcattgg aaaacgttct tcggggcgaa aactctcaag gatcttaccg    6360
ctgttgagat ccagttcgat gtaacccact cgtgcaccca actgatcttc agcatctttt    6420
actttcacca gcgtttctgg gtgagcaaaa acaggaaggc aaaatgccgc aaaaaaggga    6480
ataagggcga cacggaaatg ttgaatactc atactcttcc ttttcaata ttattgaagc     6540
atttatcagg gttattgtct catgagcgga tacatatttg aatgtattta gaaaaataaa    6600
caaatagggg ttccgcgcac atttccccga aagtgccac                          6640
```

<210> SEQ ID NO 23
<211> LENGTH: 6624
<212> TYPE: DNA
<213> ORGANISM: artificial
<220> FEATURE:
<223> OTHER INFORMATION: vector vEM33 (H5)
<220> FEATURE:
<221> NAME/KEY: misc_feature
<222> LOCATION: (338)..(1263)
<223> OTHER INFORMATION: Fliank1 Del3
<220> FEATURE:
<221> NAME/KEY: gene
<222> LOCATION: (1283)..(1962)
<223> OTHER INFORMATION: Azami green
<220> FEATURE:
<221> NAME/KEY: misc_feature
<222> LOCATION: (2002)..(1963)
<223> OTHER INFORMATION: Ps
<220> FEATURE:
<221> NAME/KEY: misc_feature
<222> LOCATION: (2009)..(2048)
<223> OTHER INFORMATION: Ps
<220> FEATURE:
<221> NAME/KEY: gene
<222> LOCATION: (2049)..(2447)
<223> OTHER INFORMATION: BsdR
<220> FEATURE:
<221> NAME/KEY: promoter
<222> LOCATION: (2454)..(2493)
<223> OTHER INFORMATION: Ps promoter

```
<220> FEATURE:
<221> NAME/KEY: misc_feature
<222> LOCATION: (2494)..(2534)
<223> OTHER INFORMATION: TetO2
<220> FEATURE:
<221> NAME/KEY: gene
<222> LOCATION: (2535)..(3383)
<223> OTHER INFORMATION: DNAse
<220> FEATURE:
<221> NAME/KEY: promoter
<222> LOCATION: (3414)..(3483)
<223> OTHER INFORMATION: H5 promoter
<220> FEATURE:
<221> NAME/KEY: gene
<222> LOCATION: (3517)..(4173)
<223> OTHER INFORMATION: TetR
<220> FEATURE:
<221> NAME/KEY: misc_feature
<222> LOCATION: (4180)..(4690)
<223> OTHER INFORMATION: Flank2 Del3
<220> FEATURE:
<221> NAME/KEY: gene
<222> LOCATION: (5639)..(6496)
<223> OTHER INFORMATION: AmpR

<400> SEQUENCE: 23
ctaaattgta agcgttaata ttttgttaaa attcgcgtta aatttttgtt aaatcagctc      60 atttttaac caataggccg aaatcggcaa atcccttat aaatcaaaag aatagaccga      120
gatagggttg agtgttgttc cagtttggaa caagagtcca ctattaaaga acgtggactc     180
caacgtcaaa gggcgaaaaa ccgtctatca gggcgatggc ccactacgtg aaccatcacc    240
ctaatcaagt tttttggggt cgaggtgccg taaagcacta atcggaacc ctaaagggag     300 cccccgattt agagcttgac ggggaaccac tatttagttg gtggtcgcca tggatggtgt    360
tattgtatac tgtctaaacg cgttagtaaa acatggcgag gaaataaatc atataaaaaa    420
tgatttcatg attaaaccat gttgtgaaaa agtcaagaac gttcacattg gcggacaatc    480
taaaaacaat acagtgattg cagatttgcc atatatggat aatgcggtat ccgatgtatg    540
caattcactg tataaaaga atgtatcaag aatatccaga tttgctaatt tgataaagat    600
agatgacgat gacaagactc ctactggtgt atataattat tttaaaccta agatgccat    660 tcctgttatt atatccatag gaaaggatag agatgtttgt gaactattaa tctcatctga   720
taaagcgtgt gcgtgtatag agttaaattc atataaagta gccattcttc ccatggatgt   780 ttccttttt accaaaggaa atgcatcatt gattattctc ctgtttgatt tctctatcga    840
tgcggcacct ctcttaagaa gtgtaaccga taataatgtt attatatcta gacaccagcg    900
tctacatgac gagcttccga gttccaattg gttcaagttt tacataagta taaagtccga   960
ctattgttct atattatata tggttgttga tggatctgtg atgcatgcaa tagctgataa    1020
tagaacttac gcaaatatta gcaaaaatat attagacaat actacaatta acgatgagtg   1080
tagatgctgt tattttgaac cacagattag gattcttgat agagatgaga tgctcaatgg   1140
atcatcgtgt gatatgaaca gacattgtat tatgatgaat ttacctgatg taggcgaatt   1200
tggatctagt atgttgggga aatatgaacc tgacatgatt aagattgctc tttcggtggc   1260
tggcacatcg gtggcggccg cttacttggc ctgactcggc agcatagaat agcgagcaac   1320
ggcattctca tagagcttga ccttgttgta atctttgtca tgcttcaaaa tctcaatgcg   1380
gtggtccaca aagtgatagt ctggcaaacg gacatccttc tttgctttgt aagtagtttt   1440
gaaatcacat cgataatggc cacctccttc aagcaacaga gccatgttaa catcacccctt  1500 cagcactcca tcacgtacgt acattttctc agtggatggc tcccatttaa gagtcttctt   1560
ctgcataacc ggaccattgg gaggaaagtt cacaccatca aaacgaatgt catagaaaaa   1620
```

```
acagtcgccc ctcatgctta tgttgcttgt ggcggtgcaa atgccctggt cttcataagt    1680
catgcttctt tcccagtgat acccctcagg aaaagtctgc ttgaaatagt cctgaatatc    1740
tgctgggtac ttggtgaatg ccctgttgcc gtactggaac actgttgtca agatatcgta    1800
agcgaaaggc agaggtgcgc cttcagtgac gttcaggtct aaaatctgcg ttccctcgta    1860
aggatttcct tttccttctc cttcaatcac gaaattatgc ccgtttacag tgcctctcat    1920
acacagcttg atcttcatct ctggtttaat cacactcacc attatttata ttccaaaaaa    1980
aaaaaataaa atttcaattt ttgccggcaa aaattgaaat tttattttt  tttttggaa     2040 tataaataat ggccaagcct ttgtctcaag aagaatccac cctcattgaa agagcaacgg    2100
ctacaatcaa cagcatcccc atctctgaag actacagcgt cgccagcgca gctctctcta    2160
gcgacggccg catcttcact ggtgtcaatg tatatcattt tactgggga  ccttgtgcag    2220 aactcgtggt gctgggcact gctgctgctg cggcagctgg caacctgact tgtatcgtcg    2280
cgatcggaaa tgagaacagg ggcatcttga gcccctgcgg acggtgccga caggtgcttc    2340
tcgatctgca tcctgggatc aaagccatag tgaaggacag tgatggacag ccgacggcag    2400
ttgggattcg tgaattgctg ccctctggtt atgtgtggga gggctaaact agtaaaaatt    2460
gaaattttat tttttttttt tggaatataa atatccctat cagtgataga gatctcccta    2520
tcagtgatag agatatgagg ggcatgaagc tgctgggggc gctgctggca ctggcggccc    2580
tactgcaggg ggccgtgtcc ctgaagatcg cagccttcaa catccagaca tttggggaga    2640
ccaagatgtc caatgccacc ctcgtcagct acattgtgca gatcctgagc cgctatgaca    2700
tcgccctggt ccaggaggtc agagacagcc acctgactgc cgtggggaag ctgctggaca    2760
acctcaatca ggatgcacca gacacctatc actacgtggt cagtgagcca ctgggacgga    2820
acagctataa ggagcgctac ctgttcgtgt acaggcctga ccaggtgtct gcggtggaca    2880
gctactacta cgatgatggc tgcgagccct gcgggaacga caccttcaac cgagagccag    2940
ccattgtcag gttcttctcc cggttcacag aggtcaggga gtttgccatt gttccctgc    3000 atgcggcccc gggggacgca gtagccgaga tcgacgctct ctatgacgtc tacctggatg    3060
tccaagagaa atggggcttg gaggacgtca tgttgatggg cgacttcaat gcgggctgca    3120
gctatgtgag accctcccag tggtcatcca tccgcctgtg gacaagcccc accttccagt    3180
ggctgatccc cgacagcgct gacaccacag ctacacccac gcactgtgcc tatgacagga    3240
tcgtggttgc agggatgctg ctccgaggcg ccgttgttcc cgactcggct cttcccttta    3300
acttccaggc tgcctatggc ctgagtgacc aactggccca agccatcagt gaccactatc    3360
cagtggaggt gatgctgaag taggagctcc accgcggtgg cggccgctct agaaaaaaat    3420
gaaaataaat acaaaggttc ttgagggttg tgttaaattg aaagcgagaa ataatcataa    3480
attggatccc ccgggctgca ggaattcgat ctcgagatgt ctagattaga taaaagtaaa    3540
gtgattaaca gcgcattaga gctgcttaat gaggtcggaa tcgaaggttt aacaacccgt    3600
aaactcgccc agaagctagg tgtagagcag cctacattgt attggcatgt aaaaaataag    3660
cgggctttgc tcgacgcctt agccattgag atgttagata ggcaccatac tcacttttgc    3720
cctttagaag gggaaagctg gcaagatttt ttacgtaata acgctaaaag ttttagatgt    3780
gctttactaa gtcatcgcga tggagcaaaa gtacatttag gtacacggcc tacagaaaaa    3840
cagtatgaaa ctctcgaaaa tcaattagcc ttttttatgcc aacaaggttt ttcactagag    3900
aatgcattat atgcactcag cgctgtgggg catttttactt taggttgcgt attggaagat    3960
caagagcatc aagtcgctaa agaagaaagg gaaacaccta ctactgatag tatgccgcca    4020
```

```
ttattacgac aagctatcga attatttgat caccaaggtg cagagccagc cttcttattc    4080
ggccttgaat tgatcatatg cggattagaa aaacaactta aatgtgaaag tgggtccgcg    4140
tacagcggat cccgggaatt cagatcttat taagggcccg gaaagtttta taggtagttg    4200
atagaacaaa atacataatt ttgtaaaaat aaatcacttt ttatactaat atgacacgat    4260
taccaatact tttgttacta atatcattag tatacgctac acctttcct cagacatcta     4320 aaaaaatagg tgatgatgca actttatcat gtaatcgaaa taatacaaat gactacgttg    4380
ttatgagtgc ttggtataag gagcccaatt ccattattct tttagctgct aaaagcgacg    4440
tcttgtattt tgataattat accaaggata aaatatctta cgactctcca tacgatgatc    4500
tagttacaac tatcacaatt aaatcattga ctgctagaga tgccggtact tatgtatgtg    4560
cattctttat gacatcgcct acaaatgaca ctgataaagt agattatgaa gaatactcca    4620
cagagttgat tgtaaataca gatagtgaat cgactataga cataatacta tctggatcta    4680
cacattcacc ggaaactagg gcttcctcgc tcactgactc gctgcgctcg gtcgttcggc    4740
tgcggcgagc ggtatcagct cactcaaagg cggtaatacg gttatccaca gaatcagggg    4800
ataacgcagg aaagaacatg tgagcaaaag gccagcaaaa ggccaggaac cgtaaaaagg    4860
ccgcgttgct ggcgtttttc cataggctcc gccccctga cgagcatcac aaaaatcgac      4920
gctcaagtca gaggtggcga aacccgacag gactataaag ataccaggcg tttcccctg     4980 gaagctccct cgtgcgctct cctgttccga ccctgccgct taccggatac ctgtccgcct    5040
ttctcccttc gggaagcgtg cgctttctc atagctcacg ctgtaggtat ctcagttcgg     5100
tgtaggtcgt tcgctccaag ctgggctgtg tgcacgaacc ccccgttcag cccgaccgct    5160
gcgccttatc cggtaactat cgtcttgagt ccaacccggt aagacacgac ttatcgccac    5220
tggcagcagc cactggtaac aggattagca gagcgaggta tgtaggcggt gctacagagt    5280
tcttgaagtg gtggcctaac tacggctaca ctagaaggac agtatttggt atctgcgctc    5340
tgctgaagcc agttaccttc ggaaaaagag ttggtagctc ttgatccggc aaacaaacca    5400
ccgctggtag cggtggtttt tttgtttgca agcagcagat tacgcgcaga aaaaaggat     5460 ctcaagaaga tcctttgatc ttttctacgg ggtctgacgc tcagtggaac gaaaactcac    5520
gttaagggat tttggtcatg agattatcaa aaaggatctt cacctagatc cttttaaatt    5580
aaaaatgaag ttttaaatca atctaaagta tatatgagta aacttggtct gacagttacc    5640
aatgcttaat cagtgaggca cctatctcag cgatctgtct atttcgttca tccatagttg    5700
cctgactccc cgtcgtgtag ataactacga tacgggaggg cttaccatct ggccccagtg    5760
ctgcaatgat accgcgagac ccacgctcac cggctccaga tttatcagca ataaaccagc    5820
cagccggaag ggccgagcgc agaagtggtc ctgcaacttt atccgcctcc atccagtcta    5880
ttaattgttg ccgggaagct agagtaagta gttcgccagt taatagtttg cgcaacgttg    5940
ttgccattgc tacaggcatc gtggtgtcac gctcgtcgtt tggtatggct tcattcagct    6000
ccggttccca acgatcaagg cgagttacat gatccccat gttgtgcaaa aaagcggtta     6060
gctccttcgg tcctccgatc gttgtcagaa gtaagttggc cgcagtgtta tcactcatgg    6120
ttatggcagc actgcataat tctcttactg tcatgccatc cgtaagatgc ttttctgtga    6180
ctggtgagta ctcaaccaag tcattctgag aatagtgtat gcggcgaccg agttgctctt    6240
gcccggcgtc aatacgggat aataccgcgc cacatagcag aactttaaaa gtgctcatca    6300
ttggaaaacg ttcttcgggg cgaaaactct caaggatctt accgctgttg agatccagtt    6360
cgatgtaacc cactcgtgca cccaactgat cttcagcatc ttttactttc accagcgttt    6420
```

-continued

```
ctgggtgagc aaaaacagga aggcaaaatg ccgcaaaaaa gggaataagg gcgacacgga    6480
aatgttgaat actcatactc ttccttttc aatattattg aagcatttat cagggttatt    6540
gtctcatgag cggatacata tttgaatgta tttagaaaaa taaacaaata ggggttccgc    6600
gcacatttcc ccgaaaagtg ccac                                          6624
```

SINGLE RECOMBINATION SYSTEM AND METHODS OF USE

CROSS-REFERENCE TO RELATED APPLICATIONS

This application is the National Stage of International Application Number PCT/EP2009/009028, filed Dec. 16, 2009, which claims the benefit of U.S. Provisional Application No. 61/139,991, filed Dec. 22, 2008, and European Application No. 08022296.1, filed Dec. 22, 2008, each of which is incorporated by reference herein.

REFERENCE TO A SEQUENCE LISTING SUBMITTED ELECTRONICALLY VIA EFS-WEB

The content of the electronically submitted sequence listing (Name: sequencelisting_ascii.txt; Size: 89,309 bytes; and Date of Creation: Jun. 8, 2011) is herein incorporated by reference in its entirety.

The present invention relates to a single recombination system for the cloning of recombinant poxviruses by a single recombination event in a modified poxvirus vector. It further relates to the modified poxvirus vectors, uses thereof and a method for the production of recombinant poxviruses.

BACKGROUND OF THE INVENTION

Recently, significant effort has been invested in developing and improving recombinant poxvirus-based technologies. Poxvirus-based vectors have been identified as beneficial for a number of uses such as generating immune responses through vaccines, in the development of new vaccine therapies, and use in gene therapy applications. The advantages associated with recombinant poxvirus vectors are well-known and include efficient delivery of genetic material to multiple cell types; generous levels of protein expression; and the ability to elicit cell-mediated immune responses in addition to antibody-based responses.

Poxviruses are well-known cytoplasmic viruses, thus any genetic material carried by such viral vectors normally remains in the cytoplasm without the disadvantage of inadvertent integration into the host cell genome. Poxviruses can be readily genetically engineered to contain and express foreign genes that have been inserted into their genome using, for example, cloning techniques such as homologous recombination. These foreign genes can encode a wide range of proteins, such as antigens that induce protection against one or more infectious agents, immune modulating proteins such as co-stimulatory molecules, or enzymatic proteins. For example, recombinant poxviruses have been engineered to express immunizing antigens of herpes virus, influenza, and human immunodeficiency virus (HIV).

One of the main advantages of poxviruses as vectors is their large genome size, which permits the insertion of a large amount of heterologous genetic material including, for example, multiple genes (i.e., as a multivalent vector). However, the heterologous genetic material must be inserted at an appropriate site within the pox genome for the recombinant virus to remain viable. Thus, the genetic material must be inserted at a site in the viral DNA which is non-essential.

A well-established approach for the cloning of recombinant poxviruses is based on two separate recombination events. During the first recombination step, a gene of interest and a reporter and/or marker cassette are integrated into a viral genome. For the selection process, an antibiotic resistance gene is commonly used. Following the subsequent isolation of recombinant poxviruses from the pool of recombinant and non-recombinant poxviruses using the selection/marker cassette, the selection and marker cassette should be deleted if the recombinant poxvirus is intended for use as, for example, a vaccine in humans. For this purpose, a second recombination event must be performed involving further passaging and plaque purification of the recombinant poxvirus. Consequently, presently known techniques for cloning recombinant poxviruses are usually time-consuming and laborious endeavors, especially when compared to those procedures commonly used for the cloning of other types of recombinant expression vectors.

Accordingly, there is a need in the art for improved cloning systems and methods for the efficient generation of recombinant poxviruses.

SUMMARY OF THE INVENTION

The present invention is based on a modified poxvirus vector that allows for the generation of recombinant poxviruses by a single recombination event. The modified viral vector of the invention comprises a reporter gene that is deleted if a recombination with the insert of interest successfully occurs.

In a first aspect, the present invention is directed to a modified poxvirus vector comprising at least one reporter gene located between two flanking sequences for homologous recombination. In one embodiment, the modified poxvirus vector further comprises at least one selection component located between the two flanking regions for homologous recombination in a permissive host cell. In another embodiment, the selection component comprises a selection gene that inhibits or slows down poxvirus replication in the host cell or is cytotoxic to the host cell. In another embodiment, the reporter gene and the selection component are located between a single pair of flanking sequences allowing for homologous recombination. In yet another embodiment, the reporter gene and the selection component are located between more than one pair of flanking sequences allowing for homologous recombination. In a further embodiment, the selection component comprises a selection gene whose expression is inducible. In a specific embodiment, the reporter gene codes for a fluorescent protein, for example, green fluorescent protein. In a further specific embodiment, the selection component comprises a selection gene selected from a gene coding for a DNAse, a RNase, or a protease. In a further specific embodiment, expression of the selection gene is under the control of a regulatory sequence, preferably a promoter. In another specific embodiment the selection gene is regulated by an inducible expression system, for example, the tetracycline operator/repressor (TetO2/TetR) system.

In another aspect, the present invention is directed to a recombinant poxvirus generated using a modified poxvirus vector of the present invention.

In another aspect, the present invention is directed to a host cell comprising a modified poxvirus vector of the present invention. In a further aspect, the present invention is directed to a host cell comprising a recombinant poxvirus generated using a modified poxvirus vector of the invention.

In a further aspect, the invention provides a method of using the modified poxvirus vector to generate a recombinant poxvirus. In another aspect, the present invention is directed to a method for the generation of a recombinant poxvirus that comprises infecting a permissive host cell with a modified poxvirus vector according to the present invention, and subsequent transfection of the host cell with a plasmid comprising heterologous genetic material of interest, under conditions that permit homologous recombination between the vector and plasmid. In one embodiment, the method comprises inducing expression of the selection gene. In a further embodiment, the method comprises separating host cells comprising the recombinant poxvirus from host cells comprising non-recombinant poxvirus. In a further embodiment, the method comprises using permissive host cells comprising the recombinant poxvirus for at least one further passage in previously uninfected permissive host cells.

In a further aspect, the present invention is directed to the use of the modified poxvirus vector according to the invention for the generation of a recombinant poxvirus.

In particular embodiments, the modified poxvirus vector according to the invention is a vaccinia virus. In a further particular embodiment, the modified poxvirus vector according to the invention is a Modified Vaccinia Ankara virus (MVA). In a further aspect, the present invention is directed to the modified poxvirus according to the invention, the recombinant poxvirus according to the invention, and a cell according to the invention comprising the modified or recombinant poxvirus as a medicament. In specific embodiments the present invention is directed to the modified poxvirus according to the invention, the recombinant poxvirus according to the invention, and a cell according to the invention comprising the modified or recombinant poxvirus as a therapeutic or prophylactic vaccine for the treatment or prevention of cancer, influenza, hepatitis, AIDS, mumps, rabies, encephalitis, stomach or duodenal ulcers, malaria, sleeping sickness, lyme disease, reactive arthritis, pneumonia, leprosy, diphtheria, candidiasis and/or toxoplasmosis. In a specific embodiment, the medicament is a therapeutic or prophylactic vaccine. In another specific embodiment, the medicament is a therapeutic or prophylactic vaccine for the treatment of cancer.

Other embodiments of the invention are provided by the detailed description, the Examples, and the appended claims.

BRIEF DESCRIPTION OF THE DRAWINGS

FIG. 11 depicts the resulting PCR analysis of the Deletion III site. The insertion site for foreign genes in the MVA genome (deletion 3) was investigated using PCR.

DETAILED DESCRIPTION

Figure 1:
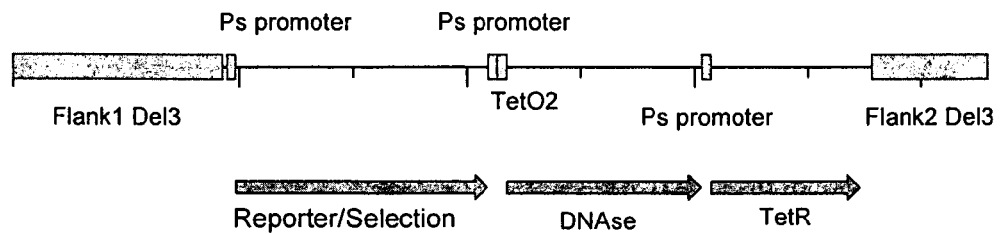
FIG. 1 illustrates the reporter/selection cassette of an exemplary modified poxvirus vector according to the invention. The vector is based on the MVA genome (Gene Bank Accession #U94848; Antoine, G., Scheiflinger, F., Dorner, F. and Falkner, F. G. "The complete genomic sequence of the modified vaccinia Ankara strain: comparison with other orthopoxviruses", Virology 244 (2), 365-396 (1998)) into which the reporter/selection cassette was introduced into the insertion site (Deletion III). Flank1 Del3=flanking sequences upstream of the Deletion III site of the MVA genome; Ps promoter=strong synthetic promoter; TetO2=Tetracycline Operator (the binding site for TetR); TetR=Tetracycline Repressor; Flank2 Del3=flanking sequences downstream of the deletion III site of the MVA genome.

The present invention is based on a modified vector derived from a poxvirus that permits the generation of recombinant poxviruses by means of a single recombination event. The modified viral vector of the invention comprises a reporter gene that is deleted if a recombination with the insert of interest successfully takes place. Thus, the modified viral vector of the present invention provides for the detection of a single recombination event which simultaneously deletes the reporter/selection cassette and inserts the heterologous genetic material of interest in the recombinant viral vector.

DEFINITIONS

The term "vector" as used herein means any genome or part or fragment thereof of a poxvirus that contains sufficient genetic information to allow reproduction of the poxvirus in a permissive host cell. The vector according to the present invention can be a genetically engineered vector, such that it may only contain part or all of the elements of the poxvirus it is derived from, and/or additional genetic elements. In a specific embodiment, the vector according to the present invention is the genome or part or fragment thereof of the Modified Vaccinia Ankara (MVA) virus. In further specific embodiments, the vector according to the present invention is the genome or part thereof of an MVA virus selected from the group consisting of MVA-F6 (e.g. Lotz et al. "Partial tyrosinase-specific self tolerance by HLA-A*0201-restricted cytotoxic T lymphocytes in mice and man", Intern. J. of Cancer 2003; 108 (4): 571-79), MVA575 (ECACC deposit number V00120707), MVA-M4 (Ober et al. "Immunogenicity and safety of defective Vaccinia virus lister: Comparison with modified Vaccinia virus Ankara", J. Virol 2002; 76 (15): 7713-23), Acam3000 (Accession number AY603355), MVA-ATCC (ATCC VR-1508), MVATGN33.1 (Accession number EF675191), MVA-1721 (Accession number DQ983236).

In another embodiment of the invention, the vector according to the present invention is the genome or part thereof of a poxvirus selected from the group consisting of Vaccinia virus Western Reserve (Accession number NC006998), Vaccinia virus Wyeth (e.g. Fogg et al, "Virus induced by Vaccination with multiple recombinant outer membrane proteins of intracellular and extracellular virions", J. Virol. 2004; 78 (19): 10230-37), Vaccinia virus Lister (Accession number DQ191324), NYCBH (New York City Board of Health); CDC (Centers for Disease Control and Prevention), Vaccinia (smallpox) vaccine recommendations of the Immunization Practices Advisory Committee (ACIP), *Morbidity and Mortality Weekly Report* 40(R14): 1-10, 1991.), Canary pox (Accession number 005309 and AY318871), Fowlpox (Accession number 581527), Vaccinia virus Copenhagen (Accession number M35027) NYVAC, ALVAC, TROVAC (Paoletti et al. "Highly attenuated poxvirus vectors: NYVAC, ALVAC, TROVAC", Dev. Biol. Stand. 1995, 84: 159-63).

The term "reporter gene" as used herein means a gene conferring certain characteristics on cells or organisms expressing them which can be readily detected, identified or measured. Reporter genes are commonly used to determine whether a gene of interest has been incorporated or is expressed by a cell or organism population. In the context of the present invention, detection of the expression product from the reporter gene indicates that no homologous recombination has occurred, and that the gene insert of interest has not been successfully inserted into the viral vector. Generally, any reporter gene can be used that permits a separation of cells comprising the original vector of the invention and those cells comprising a vector where homologous recombination has occurred. Non-limiting examples of reporter genes that are suitable for use in the present invention include reporter genes that can induce visually identifiable characteristics (e.g. involving fluorescence), which enables separation by, for example, FACS and luminescent proteins such as the gene coding for jellyfish green fluorescent protein (GFP), the gene coding for the enhanced GFP (eGFP), mPlum, mCherry, tdTomato, mStrawberry, mRaspberry, mRFP1, mTangerine, mYFP (Tsien), J-Red, AceGFP, CopGFP, HcRed-tandem, PhiYFP (Evrogen), DsRed, DsRed2, DsRed-Express, DsRed-monomer, EGFPAcGFP1, AmCyan1, AsRed2, EBFP, HcRed1, ZsYellow1 (Clontech), mKO, Azami-Green, mAG, Kaede, MiCy (MBL Intl.), Venus (Miyawaki), Ypet, CyPer (Dougherty), EYFP, Emerald (Invitrogen), Cerulean (Priston), T-Sapphire (Griesbeck), AQ143 (Lukyanov), cOFP (Stratagene), eqFP611 (Weidenmann), *Renilla* GFPs (various providers, e.g. Stratagene), the luciferase gene or the lacZ gene. In one embodiment of the invention, the reporter gene is a fluorescence coding gene.

Further non-limiting examples of reporter genes include genes coding for proteins for which specific antibodies exist and that are displayed on the surface on the host cell. Such reporter genes permit the separation of cells comprising the original vector of the invention and cells comprising a vector in which homologous recombination has taken place by affinity purification, for example, by columns comprising antibody covered resin or magnetic beads covered with said antibodies, wherein the antibodies are specific for the protein encoded by the reporter gene. In a specific embodiment, the reporter gene codes for a fusion gene of a cell surface receptor and an affinity tag so that the affinity tag is displayed on the cell surface. The skilled person is aware of a variety of affinity tags and corresponding ligands that are commonly used. In further specific embodiments, the gene codes for a fusion gene of a cell surface receptor and the fused affinity tag is selected from the group consisting of a FLAG-tag (N-DYKD-DDDK-C), an epitope tag, the V5-tag, the c-myc-tag, the His-tag and/or the HA-tag. In a further embodiment, the reporter gene codes for a small viral surface protein selected from the group consisting of Alphavirus E1 and E2, Flavivirus E1 and E2, Coronavirus S, HE, M and E, Arterivirus GP, Rhabdovirus G, Filovirus GP, Paramyxovirus F, HN, H and G, Orthomyxovirus M2, NA, HA and HEF, Bunyavirus Gn and Gc, Arenavirus GP, Bornavirus G, Retrovirus Env, Hepadnavirus S, M and L.

The term "selection component" as used herein refers to any nucleic acid that may be utilized to exert a selection pressure on a host cell comprising such a selection component. In one embodiment, selection pressure is exerted by expression of a selection gene that inhibits or retards virus replication in the host cell. In another embodiment, selection pressure is exerted by expression of a selection gene that leads to a dying off of the host cell. In one embodiment, the selection component comprises at least one selection gene whose expression is inducible. In a specific embodiment, the induction of the expression is controlled by means of regulatory sequences, for example, a promoter. In a further embodiment, the selection component further comprises a bacterial inducible system that regulates expression of the selection gene. In one specific embodiment, the bacterial inducible system features the selection gene under the control of a promoter that is fused to a repressor binding site, wherein the selection component further comprises a gene coding for a repressor that binds to the repressor binding site. In a further specific embodiment, the repressor binding site is the tetracycline repressor binding site/operator (TetO2) and the gene coding for a repressor is the tetracycline repressor gene (TetR), which can be isolated from the pcDNA6TR plasmid (available from Invitrogen). In further embodiments, the selection component further comprises a mammalian inducible system that regulates the expression of the selection gene. In a specific embodiment, the mammalian inducible system is the RheoSwitch (New England Biolabs) system. In further specific embodiments, the inducible system is selected from the group consisting of the LentiX system (Clontech), the Q-mate system (Krackeler Scientific, Inc.), the Cumate-inducible expression system (NRC Canada), and/or the Genostat system (Upstate).

In a further embodiment of the invention, the selection gene is a cytotoxic gene. The term "cytotoxic gene" as used herein refers to any gene that, upon expression, will lead to the loss or complete apoptosis of the host cell, wherein said loss or apoptosis of the host cell is caused by the expressed gene product itself and only involves the direct interactions between the expressed gene product and naturally occurring components of the host cell (e.g. the host cell's DNA, RNA, proteosome, membranes or metabolites). In specific embodiments, the cytotoxic gene codes for a DNase (e.g. available from Invitrogen; ORF clone pENTR221, clone ID IOH23149), an RNase, a protease, an ion channel, or an apoptosis inducer, such as caspase and/or ROS.

The term "insert" or "insert of interest" as used herein refers to any nucleic acid that is to be introduced into the vector of the invention by homologous recombination. In one embodiment, the insert comprises at least one heterologous gene flanked by flanking sequences that allow homologous recombination to take place with the vector of the invention.

In a specific embodiment of the invention, at least one heterologous gene is under the control of a regulatory sequence, preferably a promoter.

Figure 2:
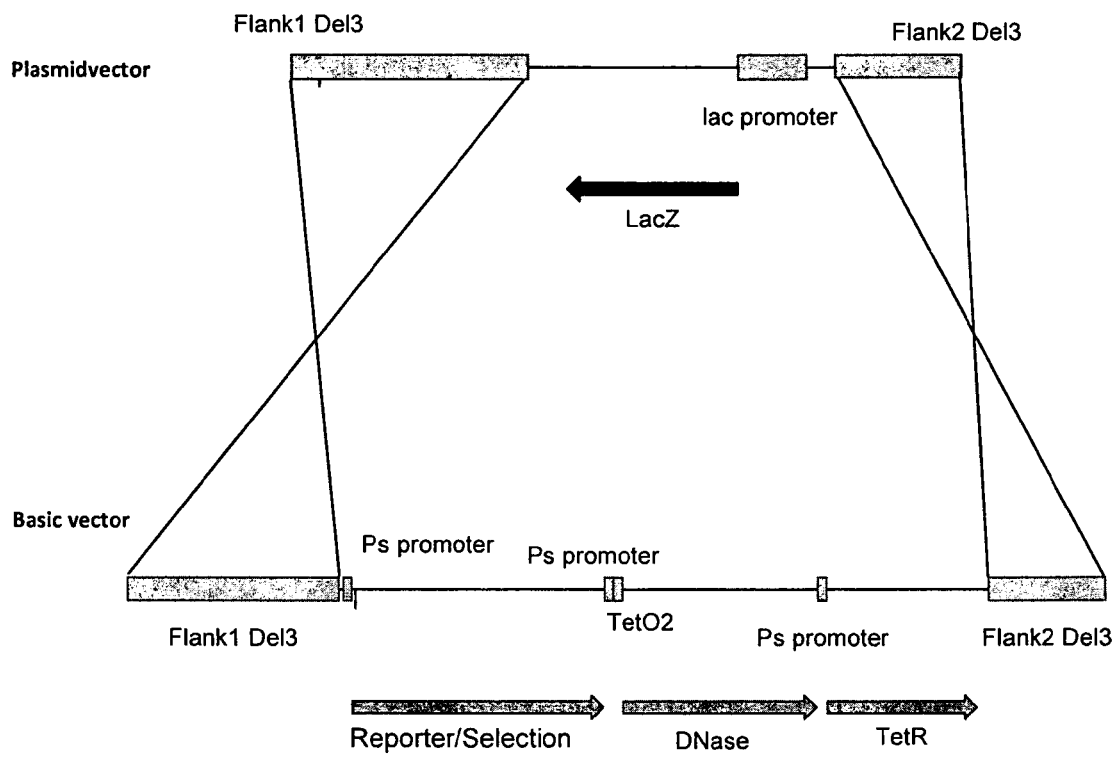
FIG. 2 is a schematic representation of the process of homologous recombination in host cells permissive for the poxvirus. For a MVA poxvirus such host cells include, for example, chicken embryo fibroblasts (CEF). Following infection of cells with the modified poxvirus vector of the present invention, the cells are transfected with a plasmid that contains the genetic material of interest (e.g. LacZ) located between two flanking sequences for homologous recombination (Flank 1/2 Del3). A recombinant poxvirus is produced where the homologous flanks recombine resulting in incorporation of the genetic material of interest, and deletion of the reporter/selection cassette.

An example of an insert of interest is depicted in FIG. 2. Here, the insert is comprised of the plasmid vector that is used to transfect the host cell and comprises the two flanking regions and the LacZ gene under control of the lac promoter. In a specific embodiment, the heterologous gene codes for at least one antigen, preferably an antigen that is capable of inducing an immune response in a patient. In specific embodiments, the heterologous gene codes for an antigen selected from the group consisting of an antigen of a heterologous virus, an antigen of a bacterium, an antigen of a prokaryote, an antigen of a fungus, and/or an antigen of a helminth. In particular embodiments, the heterologous gene codes for an antigen of a species selected from the group consisting of Influenza virus A, B, C, Hepatitis virus A, B, C, E, Human Immunodeficiency virus, Rubella virus, Mumps virus, Rabies virus, Human papilloma virus, Epstein Barr virus, Tickborne virus, Crimean Kongo Fever virus, Ebola virus, Nipah virus, Dengue virus, Chikungunya virus, Enterovirus, West Nile virus, Rift Valley Fever virus, Japanese encephalitis virus, Hantavirus, Rotavirus, SARS Coronavirus, New emerging viruses, *Chlamydia trachomatis, Clostridium botulinum, Clostridium tetani, Bacillus anthracis, Legionella pneumophila, Neisseria meningitidis (Menigococcus), Yersinia pestis, Mycobacterium tuberculosis, Mycobacterium leprae, Salmonella typhi, Listeria monocytogenes, Vibrio cholerae, Haemophilus influenzae, Bordetella pertussis, Helicobacter pylori, Borrelia* spp. (*recurrentis, hispanica, parkeri, burgdorferi*), *Leptospira interrogans, Rickettsia* spp., *Coxiella burnettii, Mycoplasma pneumonia, Corynebacterium diphtheriae, Treponema pallidum, Plasmodium falciparum, Plasmodium vivax, Plasmodium ovale, Plasmodium malariae, Entamoeba hystolytica, Giardia intestinalis, Trypanosoma brucei, Leishmania* spp., *Histoplasma capsulatum, Aspergillus* spp., *Candida albicans, Cryptococcus neoformans, Pneumocystis carinii, Wuchereria bancrofti, Schistosoma mansoni* and/or *Toxoplasma gondii*.

In a further specific embodiment, the heterologous gene codes for at least one antigen that induces a protective or therapeutic immune response against infectious diseases (e.g. viral and bacterial surface proteins) or against cancer cells, for example, cells of cervical carcinoma, melanoma, multiple myeloma, breast cancer, prostate cancer, follicular B-cell non-Hodgkins lymphoma and/or kidney cancer.

Vectors of the Present Invention

In a first aspect, the present invention relates to a modified poxvirus vector comprising at least one reporter gene located between two flanking sequences for homologous recombination. The reporter gene may be replaced by an insert of interest through homologous recombination in a host cell infected with the modified poxvirus vector. Therefore, host cells comprising a modified poxvirus vector of the present invention, in which homologous recombination has taken place, can be distinguished from those host cells comprising a modified poxvirus vector where such a homologous recombination has not taken place. This can be accomplished by means of detecting the protein coded for by the reporter gene. For example, if the reporter gene encodes the GFP or the azami green protein, then host cells comprising a modified poxvirus vector of the present invention in which homologous recombination has taken place will not produce the GFP or azami green protein, because the genetic information for the GFP or azami green protein has been removed from the vector by the homologous recombination event and has been replaced with the insert of interest. Accordingly, such host cells will not display fluorescence upon excitation and can, for example, be separated from those cells that do fluoresce by fluorescence activated cell sorting (FACS).

In one embodiment, the reporter gene is under the control of a promoter, preferably a virus promoter, more preferably a vaccinia virus promoter or a synthetic promoter. In another embodiment, the promoter is a strong promoter, preferably a strong synthetic promoter. In a specific embodiment, the promoter is the Ps promoter having the sequence AAAAAT-TGAAATTTTATTTTTTTTTTTGGAATATAAATA (Sekhar Chakrabarti, Jerry R. Sisler and Bernard Moss: Compact, synthetic, Vaccinia Virus Early/Late Promoter for Protein Expression. Biotechniques 23:1094-1097, 1997). In another specific embodiment the promoter is the modified H5 promoter having the sequence AAAAAAT-GAAAATAAATACAAAGGTT CTTGAGGGTTGTGT-TAAATTGAAAGCGAGAAATAATCATAAATT; Rosel J L, Earl P L, Weir J P, Moss B, "Conserved TAAATG sequence at the transcriptional and translational initiation sites of vaccinia virus late genes deduced by structural and functional analysis of the HindIII H genome fragment", J. Virol. 60 (2): 236-249, 1986).

In a further embodiment, the reporter gene encodes a fluorescent protein. "Empty" vectors (i.e., vectors in which no recombination events have taken place) express the reporter gene, and therefore cells comprising such vectors can fluoresce. Homologous recombination in a permissive cell leads to deletion of the reporter gene, and the procedure results in recombinant vectors containing the insert of interest that do not cause fluorescence in the host cell. In specific embodiments, the fluorescent protein is GFP, enhanced GFP (eGFP), or the azami green protein (available from MBL International Inc., Woburn, Mass., USA and distributed by MoBiTec GmbH, Goettingen, Germany).

In a further aspect, the vector of the present invention further comprises at least one selection component that is similarly located between the two flanking sequences for homologous recombination. In one embodiment, the reporter gene and the selection component are located between more than one pairs of flanking sequences allowing for homologous recombination. In another embodiment, the selection component comprises a selection gene whose expression is inducible. In a further embodiment, the selection component further comprises a bacterial inducible system that regulates expression of the selection gene. In one specific embodiment, the bacterial inducible system features the selection gene under the control of a promoter that is fused to a repressor binding site, wherein the selection component further comprises a gene coding for a repressor that binds to the repressor binding site. In a further specific embodiment, the repressor binding site is the tetracycline repressor binding site/operator (TetO2) and the gene coding for a repressor is the tetracycline repressor gene (TetR), which can be isolated from the pcDNA6TR plasmid (available from Invitrogen). Upon transfection of the host cell, the repressor is expressed in the cell and binds to the repressor binding site of the selection component upstream to the selection gene to thereby suppress expression of the selection gene. Once tetracycline is added to the system, it binds to the tetracycline repressor and immediately detaches from the binding site on the DNA which, in turn, leads to the expression of the selection gene. Consequently, expression of the selection gene is dependent on the addition of tetracycline and, therefore, expression of the selection gene is rendered inducible. In a further embodiment, the promoter that controls expression of the selection gene and the gene coding for the repressor, is a virus promoter, a vaccinia virus promoter or, most preferably, a strong synthetic promoter, such as the Ps promoter or the modified H5 promoter.

In a further embodiment of the invention, the selection component comprises a selection gene that, upon expression, inhibits or retards virus replication in the host cell. If the selection gene is induced, this allows for an improved selection of viruses comprising the vector of the invention where homologous recombination has taken place, and the selection component and the reporter gene have been replaced with the insert of interest. Consequently, host cells comprising a vector in which homologous recombination has taken place, harbor more replicated recombinant viruses than those where no homologous recombination has taken place. Furthermore, the inhibitor of viral replication is expressed, leading to a decreased or even complete prohibition of viral replication. Thus, the ratio of produced viruses comprising a genome including the insert of interest to those viruses comprising the genome without said insert of interest is significantly shifted in favor of the former. Accordingly, as a percentage, the system can be manipulated to generate an improved yield of viruses comprising the insert of interest. In particular embodiments, the selection gene is an RNase, an ion channel or, a DNase (available from Invitrogen; ORF clone pENTR221, clone ID IOH23149).

In a further embodiment of the invention, the selection component is a cytotoxic gene, i.e. any gene that, upon expression, will lead to the loss or complete apoptosis of the host cell. In specific embodiments, the cytotoxic gene codes for a DNase, an RNase, a protease, an ion channel, or an apoptosis inducer.

According to the invention, the selection component is an optional embodiment of the invention, since host cells harboring a recombinant vector of the invention comprising the insert of interest can be selected and isolated by means of the reporter gene alone. While the reporter gene is essential for the detection and/or selection of such a recombinant vector, the optional inducible expression of the selection component can be used for, for example, single or multiple passages of vector production.

In particular embodiments, the selection component may, for example, significantly accelerate the generation of recombinant poxviruses comprising the insert of interest, as host cells not harboring a recombinant vector of the invention comprising said insert are directed to produce less or no viruses (or are killed entirely) upon induction of the selection component. In this case, the recombinant vectors of the invention, containing a reporter gene and a selection component result in fluorescence expressing "empty" vectors sensitive against tetracycline and the tetracycline-insensitive recombinant vectors devoid of any fluorescence. In other words, only cells containing empty vector exhibit fluorescence and thus the non-recombinants can be separated by techniques including plaque picking or FACS sorting. If the expression of the selection component is induced beforehand, the separation can be carried out in a significantly improved manner, since the number of cells harboring "empty" vectors is dramatically and beneficially reduced prior to separation.

In further embodiments of the present invention, flanking regions permit homologous recombination. Homologous recombination generally involves the alignment of similar sequences, formation of a Holliday junction, and breaking and repair (known as resolution) of the nucleic acid resulting in an exchange of material between the strands of the nucleic acids. Therefore, any flanking regions that are similar enough to allow for homologous recombination are encompassed by the present invention. In a specific embodiment, the flanking regions are identical. In a further specific embodiment, the flanking regions have a size of 50 to 1000 bp, preferably they have a size of 100 to 1000 bp.

In particular embodiments, the flanking regions of the recombinant poxvirus vector are flanking regions upstream and downstream of a deletion site of the MVA genome. In a specific embodiment, the flanking regions are flanking regions 50 to 1000 bp, preferably 100 to 1000 bp, upstream and downstream of Deletion sites I, II, III, IV, V, or VI of the MVA genome (MVA genome position: Del I: 7608/7609, Del II: 20718/20719; Del III: 149341/149342; Del IV: 170480; Del V: 19754/19755; Del VI 9831/9832). SEQ ID NOs: 2-7 show the flanking regions of Deletion sites I-VI, respectively, centered around the Deletion site that may be used according to the present invention. As an example, SEQ ID NO: 2 is a sequence of 2002 bp, centered around Deletion site I of the MVA genome (position 7608/7609). Thus, positions 1001/1002 of SEQ ID NO: 2 correspond to positions 7608/7609 of the MVA genome. Accordingly, the flanking regions in one specific embodiment of the invention are 50 to 1000 bp upstream of position 1001 of SEQ ID NO: 2 and 50 to 1000 bp downstream of position 1002 of SEQ ID NO: 2.

In another specific embodiment, the flanking regions of the recombinant poxvirus vector are selected in a way that the insertion site will be positioned within a non-coding region of the poxvirus. Non-coding regions of poxviruses vary in length and may comprise from around 100 to more than 1000 bp. Each of the nucleotides of such a non-coding region may be selected as insertion site. The flanking regions according to the inventions are 50 to 1000 bp, preferably 100 to 1000 bp, upstream and downstream of this selected insertion site located within a non-coding region. If for example, the non-coding region has a length of 1000 bp and the insertion site would be selected to be between positions 500 and 501 than the flanking regions according to the invention would be 50 to 1000 bp upstream from position 500 and 50 to 1000 bp downstream to position 501. In specific embodiments, the non-coding region is a non-coding region of MVA. In further specific embodiments, the non-coding region is the nucleotide sequence between any of the following genes of MVA (Gen Bank Accession # U94848): 001L-002L, 002L-003L, 005R-006L, 006L-007R, 007R-008L, 017L-018L, 018L-019L, 020L-021L, 023L-024L, 024L-025L, 025L-026L, 028R-029L, 030L-031L, 031L-032L, 032L-033L, 035L-036L, 036L-037L, 037L-038L, 039L-042L, 043L-044L, 044L-045L, 046L-047L, 049L-050L, 050L-051L, 051L-052L, 052R-053R, 053R-054R, 054R-055R, 055R-056L, 056L-057R, 061L-062L, 064L-065L, 065L-066L, 066L-067L, 077L-078R, 078R-079L, 080R-081L, 085R-086R, 086R-087R, 088R-089L, 089L-090R, 094L-095R, 096R-097R, 097R-098R, 101R-102R, 103R-104R, 105L-106R, 108L-109L, 109L-110L, 110L-111L, 113L-114L, 114L-115L, 115L-116R, 117L-118L, 118L-119R, 123L-124L, 124L-125L, 125L-126L, 133R-134R, 134R-135R, 137L-138L, 141L-142L, 143L-144R, 144R-145R, 145R-146R, 146R-147R, 147R-148R, 148R-149L, 152R-153L, 153L-154R, 154R-155R, 156R-157L, 157L-158R, 159R-160L, 160L-161R, 161R-162R, 165R-166R, 166R-167R, 170R-173R, 173R-174R, 174R-175R, 175R-176R, 176R-177R, 178R-179R, 179R-180R, 180R-181R, 183R-184R, 184R-185L, 185L-186R, 186R-187R, 187R-188R and/or 188R-189R.

In another specific embodiment, the flanking regions of the recombinant poxvirus vector are selected in a way that the insertion site will be positioned within a non-essential gene of the poxvirus. A gene is considered to be a non-essential gene if it is not required for the productive replication of a given poxvirus. In specific embodiments, the non-essential gene is selected from the group consisting of the Thymidine kinase gene (=Tk; Scheiflinger F. et al. "Evaluation of the thymidine kinase (tk) locus as an insertion site in the highly attenuated vaccinia MVA strain", Arch. Virol. 1996, 141(3-4): 663-9.), the hemagglutinin gene (=HA; Antoine G. et al. "Characterization of the vaccinia MVA hemagglutinin gene locus and its evaluation as an insertion site for foreign genes", Gene, 1996 Oct. 24; 177(1-2): 43-6), the 14L coded ribonucleotide reductase (Howley P M et al. "A Vaccinia Virus transfer vector using a GUS reporter gene inserted into the 14L locus", Gene, 1996 Jun. 26; 172(2): 233-7), the E3L (Langland J O & Jacobs B L, "The role of the PKR-inhibitory genes, E3L and K3L, in determining vaccinia virus host range", Virology, 2002 Jul. 20; 299(1): 133-41), the K1L (Staib C. et al. "Recombinant MVA and method for generation thereof" EP1594970, 2005 Nov. 16) and the ATI gene (Wintersperger S. et al. "Vector for integration of heterologous sequences into poxyiral genomes", 2002 Feb. 20). In further specific embodiments, the non-essential gene is a gene from MVA and selected from 032L (Ribonucleotide reductase), 137L (function not known), 166R (Guanylate kinase fragment), 170 (function not known), 188R (function not known) and 189R (function not known).

In another embodiment of the invention, the poxvirus is a vaccinia virus. In a further embodiment, the poxvirus is MVA.

In a further aspect, the invention relates to a cell harboring the modified poxvirus vector of the present invention. Generally, every cell that is permissive for receiving the modified poxvirus vectors of the present invention is encompassed. Preferably, the cell is a eukaryotic cell. In a particular embodiment, the cell is a mammalian or an avian cell. In a specific embodiment, the cell is a chick embryo fibroblast (CEF) cell. In a further embodiment, the cell is an isolated human cell.

In a further aspect the invention is directed to the novel plasmids and vectors used for the generation of the modified poxvirus vector according to the invention. The present invention thus also encompasses a nucleic acid or its complement selected from the group consisting of SEQ ID NOs: 15-23 or a fragment or homologous nucleic acid thereto that shares at least 40%, 50%, 55%, 60%, 65%, 70%, 75%, 80%, 95%, 90%, 91%, 92%, 93%, 94%, 95%, 96%, 97%, 98%, 98.5%, 99%, 99.5%, 99.7%, 99.8%, 99.9% sequence identity, wherein the fragment has a length of at least 40%, 50%, 55%, 60%, 65%, 70%, 75%, 80%, 95%, 90%, 91%, 92%, 93%, 94%, 95%, 96%, 97%, 98%, 98.5%, 99%, 99.5%, 99.7%, 99.8%, 99.9% of the respective nucleic acid selected from the group consisting of SEQ ID NOs: 15-23.

Methods of the Present Invention

In a further aspect, the invention is directed to a method for generating a recombinant poxvirus, wherein a host cell permissible for the modified poxvirus vector of the present invention is transfected with said vector, and furthermore with a plasmid comprising heterologous genetic material of interest under conditions permitting homologous recombination between the vector and the plasmid within the host cell. Necessarily, both the modified poxvirus vector and the plasmid comprise flanking sequences that are similar enough to allow for such homologous recombination to occur. Furthermore, the modified poxvirus vector carries the reporter gene and in certain embodiments the selection component as described above between said flanking regions, while the plasmid carries the heterologous genetic material of interest between said flanking regions. Accordingly, homologous recombination between the modified poxvirus vector and the plasmid produces a recombinant vector of the invention through replacement of the reporter gene (and the selection component, if present) by the heterologous genetic material of interest.

In certain embodiments, the method utilizes a modified poxvirus vector of the invention comprising a selection component, and further comprises the additional step of inducing expression of the selection gene in the host cell. The induction of selection gene expression depends on the inducible selection component that is employed. As an example and in a specific embodiment, the selection component comprises a selection gene that encodes the DNase protein which is expressed under the regulatory control of the bacterial inducible tetracycline repressor binding site/operator (TetO2) as described above. Induction is carried out by the addition of tetracycline, which binds to the tetracycline repressor that immediately detaches from the binding site on the DNA and, this in turn allows expression of the DNase that inhibits virus replication. This induction results in a desirable selection of host cells comprising recombinant vector relative to host cells comprising modified poxvirus vector that does not comprise the gene insert of interest.

In a further embodiment, the method of the invention further comprises an additional step of separating host cells comprising the recombinant vector from those host cells comprising non-recombinant modified poxvirus vector. In a particular embodiment, this separation is carried out by means of the gene product of the expressed reporter gene. In one embodiment, the reporter gene codes for a fluorescent protein and the separation is carried out by means of FACS and an attached cell sorter. In another embodiment, the reporter gene is an arbitrary protein that is expressed on the cell surface and to which an antibody exists. Separation is then achieved by coating magnetic beads with said antibodies and contacting the cells with said magnetic beads in order to separate the two cell populations. In another embodiment, the antibodies are attached to a resin and used in a column to separate the two cell populations.

In yet another embodiment, the separated host cells comprising the recombinant vector are used for at least one additional passage on fresh host cells. Accordingly, the number of cells harboring recombinant vector, and thus the number of generated recombinant poxvirus particles, is significantly increased. In particular embodiments, at least 2, 3, 4, 5, 6, 7, 8, 9 or 10 further passages of the recombinant poxvirus are carried out. In a specific embodiment, 6 further passages of the recombinant poxvirus are carried out. In a further embodiment, the method includes the step of inducing expression of the selection gene.

In a further embodiment of the method of the present invention, the poxvirus is vaccinia virus or MVA.

The generated recombinant poxviruses can be isolated using any suitable technique known to the average skilled person, for example, by means of centrifugation.

Medical Uses of the Present Invention

In a further aspect, the present invention is directed to the modified poxvirus according to the invention, the recombinant poxvirus according to the invention, or a cell comprising the modified or recombinant poxvirus according to the invention for use as a medicament. In a specific embodiment, the medicaments of the instant invention are advantageous for use as a therapeutic or prophylactic vaccine.

In another embodiment, the present invention is directed to the modified poxvirus according to the invention, the recombinant poxvirus according to the invention, or a cell comprising the modified or recombinant poxvirus according to the invention for use as a medicament for the treatment and/or prevention of an infection in a species selected from the group consisting of Influenza virus A, B, C, Hepatitis virus A, B, C, E, Human Immunodeficiency virus, Rubella virus, Mumps virus, Rabies virus, Human papilloma virus, Epstein Barr virus, Tickborne virus, Crimean Kongo Fever virus, Ebola virus, Nipah virus, Dengue virus, Chikungunya virus, Enterovirus, West Nile virus, Rift Valley Fever virus, Japanese encephalitis virus, Hantavirus, Rotavirus, SARS Coronavirus, Emerging viruses, *Chlamydia trachomatis, Clostridium botulinum, Clostridium tetani, Bacillus anthracis, Legionella pneumophila, Neisseria meningitidis* (Menigococcus), *Yersinia pestis, Mycobacterium tuberculosis, Mycobacterium leprae, Salmonella typhi, Listeria monocytogenes, Vibrio cholerae, Haemophilus influenzae, Bordetella pertussis, Helicobacter pylori, Borrelia* spp. (*recurrentis, hispanica, parkeri, burgdorferi*), *Leptospira interrogans, Rickettsia* spp., *Coxiella burnettii, Mycoplasma pneumonia, Corynebacterium diphtheriae, Treponema pallidum, Plasmodium falciparum, Plasmodium vivax, Plasmodium ovale, Plasmodium malariae, Entamoeba hystolytica, Giardia intestinalis, Trypanosoma brucei, Leishmania* spp., *Histoplasma capsulatum, Aspergillus* spp., *Candida albicans, Cryptococcus neoformans, Pneumocystis carinii, Wuchereria bancrofti, Schistosoma mansoni* and/or *Toxoplasma gondii*. In further specific embodiments, the medicament is used for the treatment of a disease or the symptoms caused by any of these species. In particular embodiments, this disease is influenza, hepatitis, AIDS, mumps, rabies, encephalitis, stomach or duodenal ulcers, malaria, sleeping sickness, Lyme disease, reactive arthritis, pneumonia, leprosy, diphtheria, candidasis and/or toxoplasmosis.

In a further embodiment, the present invention is directed to the modified poxvirus according to the invention, the recombinant poxvirus according to the invention, or a cell comprising the modified or recombinant poxvirus according to the invention for use as a medicament for the treatment and/or prevention of cancer. In specific embodiments, the cancer is selected from the group consisting of cervical carcinoma, melanoma, multiple myeloma, breast cancer, prostate cancer, follicular B-cell non-Hodgkins lymphoma and/or kidney cancer.

In one embodiment of the invention, the medicament is used to treat a patient in need of a vaccination. In another embodiment of the invention, the recombinant poxvirus of the invention or the cell comprising said recombinant poxvirus comprises at least one gene coding for an antigen that is capable of inducing an immune response in a patient requiring a vaccination. In specific embodiments, the antigen is selected from the group consisting of an antigen of a heterologous virus, an antigen of a bacterium, an antigen of a prokaryote, an antigen of a fungus, and/or an antigen of a helminth. In particular embodiments, the antigen is an antigen of a species selected from the group consisting of Influenza virus A, B, C, Hepatitis virus A, B, C, E, Human Immunodeficiency virus, Rubella virus, Mumps virus, Rabies virus, Human papilloma virus, Epstein Barr virus, Tickborne virus, Crimean Kongo Fever virus, Ebola virus, Nipah virus, Dengue virus, Chikungunya virus, Enterovirus, West Nile virus, Rift Valley Fever virus, Japanese encephalitis virus, Hantavirus, Rotavirus, SARS Coronavirus, Emerging viruses, *Chlamydia trachomatis, Clostridium botulinum, Clostridium tetani, Bacillus anthracis, Legionella pneumophila, Neisseria meningitidis* (Menigococcus), *Yersinia pestis, Mycobacterium tuberculosis, Mycobacterium leprae, Salmonella typhi, Listeria monocytogenes, Vibrio cholerae, Haemophilus influenzae, Bordetella pertussis, Helicobacter pylori, Borrelia* spp. (*recurrentis, hispanica, parkeri, burgdorferi*), *Leptospira interrogans, Rickettsia* spp., *Coxiella burnettii, Mycoplasma pneumonia, Corynebacterium diphtheriae, Treponema pallidum, Plasmodium falciparum, Plasmodium vivax, Plasmodium ovale, Plasmodium malariae, Entamoeba hystolytica, Giardia intestinalis, Trypanosoma brucei, Leishmania* spp., *Histoplasma capsulatum, Aspergillus* spp., *Candida albicans, Cryptococcus neoformans, Pneumocystis carinii, Wuchereria bancrofti, Schistosoma mansoni* and/or *Toxoplasma gondii*. In a further specific embodiment, the antigen is a protein expressed by a cancer cell. In another specific embodiment, the antigen is a protein that is expressed by and displayed on the surface of a cancer cell.

In further specific embodiments, the recombinant poxvirus of the invention, or the cell comprising said recombinant poxvirus comprises an antigen expressed by a cancerous cell. Examples of such an antigen expressed by a cancerous cell include, but are not limited to, alpha-fetoprotein (AFP); prostate specific antigen (PSA); carcinoembryonic antigen (CEA); disialosyl LEA antigen; Melan-A/MART-1; SART3; multidrug resistance-associated protein 3 (MRP3); polycomb group protein enhancer of zeste homolog 2 (EZH2); ALDH1; Her-2; Nectin-4; gp96 heat shock protein; gp100; tyrosinase; GM2; MAGE-A3; and NY-ESO-1. In a further embodiment the recombinant poxvirus of the invention or the cell comprising said recombinant poxvirus comprises a gene encoding an antibody. In specific embodiments, such antibodies are specific for cell markers expressed on tumor cells.

The medicaments of the present invention can be administered to a patient by means known to the skilled person. In some embodiments of the invention, the medicaments are administered by injection.

EXAMPLES

For assessing the efficacy of the modified poxvirus vectors of the present invention, several foundational MVA vectors were created. These MVA vectors contain a fluorescence coding reporter gene under the control of a strong vaccinia virus promoter, and a selection component comprising a DNase selection gene under the control of a strong vaccinia virus promoter and the Tetracycline operator (TetO2) element, and the Tetracycline repressor (TetR) coding gene under the control of different promoters.

As shown in FIG. 1, the basic MVA genome was modified by the introduction of a reporter gene/selection component cassette into the insertion site (Deletion III or Del3) of the MVA genome: adjacent to the upstream flanking region of Deletion III (Flank1 Del3) a reporter gene, for example, a green fluorescence protein (GFP) gene was inserted under the control of a strong synthetic vaccinia virus promoter (Ps) as a reporter system. This reporter, for example, GFP, optimally allows the detection of the MVA that contains the cassette insert. Downstream of the reporter gene (adjacent to Flank2 Del3), a selection component was inserted into the genome. This consists of, for example, a DNase gene under the control of a strong synthetic vaccinia virus promoter (Ps), which is controlled by a bacterial operator element (TetO2) that interacts with a repressor (TetR). The repressor interaction is in turn controlled by tetracycline. In the absence of tetracycline, TetR binds to the TetO2 control sequence to thereby inhibit the expression of the DNase gene. However, in the presence of tetracycline, TetR is released from the TetO2 site to thereby allow expression of the DNase gene. The expressed DNase protein then inhibits the amplification of the viral DNA in the cytoplasm of the infected cell.

For the isolation of recombinant MVA comprising the heterologous genetic material of interest, the reporter gene/selection component cassette is deleted by means of homologous recombination. Subsequently, the resulting virus is passaged in the presence of tetracycline. Cells comprising non-recombinant modified MVA are detectable by fluorescence, and DNase expression inhibits the growth of MVA. Cells comprising recombinant MVA lack the reporter gene/ selection component cassette, and therefore they do not exhibit fluorescence, and their MVA growth is not inhibited since DNase expression does not occur. The isolation of the recombinant and the non-recombinant MVA can be performed by separation of the fluorescing and the non-fluorescing cells.

A bacterial plasmid containing the flanking sequences of the MVA Deletion III is used (FIGS. 2 and 3) as a shuttle for the insertion of the heterologous genetic material of interest into the modified MVA vector. The plasmid further comprises a LacZ expression cassette flanked by a plurality of single cutter restriction sites. The heterologous genetic material of interest that is to be inserted in the modified MVA vector is cloned into the bacterial vector vEM07 (SEQ ID NO: 1) by means of one or more single cutter restriction sites. The LacZ gene is deleted and the plasmid containing the heterologous genetic material of interest can be detected by blue white selection using X-Gal. The resulting plasmid is then used for the insertion of the heterologous genetic material of interest in the modified MVA vector by means of homologous recombination.

Example 1

Cloning of the Modified MVA Vector Selection Component

The reporter gene/selection component cassette was inserted into the MVA genome by homologous recombination. For this purpose, the single components of (i) reporter gene, (ii) Ps-TetO2-DNAse, and (iii) TetR were cloned in a stepwise fashion into a bacterial plasmid.

Cloning of the DNAse Gene

The DNase fragment (SpeI-Ps-TetO2-DNAse-SacI) was synthesized via a two-step PCR process and cloned in the vector vEM11 (SpeI/SacI) (SEQ ID NO: 15), resulting in the production of vEM12 (SEQ ID NO: 16).

For the first PCR step, the following oligonucleotides were used:

```
1) oEM167:
                                          (SEQ ID NO: 8)
TetO2-DNAse start; TCCCTATCAGTGATAGAGATCTCCCTATCA

GTGATAGAGATATGAGGGGCATGAAGCTGCTG 2) oEM168:
                                          (SEQ ID NO: 9)
DNase end-SacI; GAGCTCCTACTTCAGCATCACC
```

Figure 4:
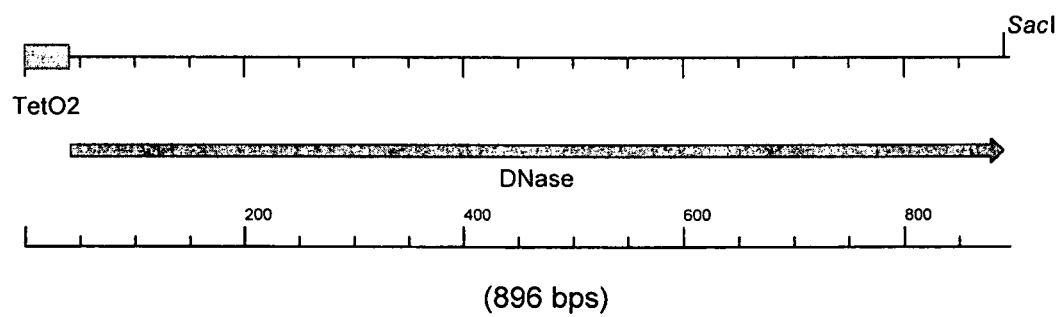
FIG. 4 schematically depicts the resulting fusion of the tetracycline operator (TetO2) to the DNAse gene achieved by PCR.

The template for this PCR process was the plasmid pENTR-DNAse (Invitrogen ORF Clone collection, clone ID IOH23149) that contained a human DNase open reading frame. This first PCR step resulted in the fragment depicted in FIG. 4.

For the second stage of the PCR, the purified PCR product of the first PCR step, and following oligonucleotides were used:

```
1) oEM169:
                                          (SEQ ID NO: 10)
SpeI-Ps-TetO2; GACTAGTAAAAATTGAAATTTTATTTTTTTTT

TGGAATATAAATATCCCTATCAGTGATAGAG 2) oEM168:
                                          (SEQ ID NO: 9)
DNase end-SacI; GAGCTCCTACTTCAGCATCACC
```

Figure 5:
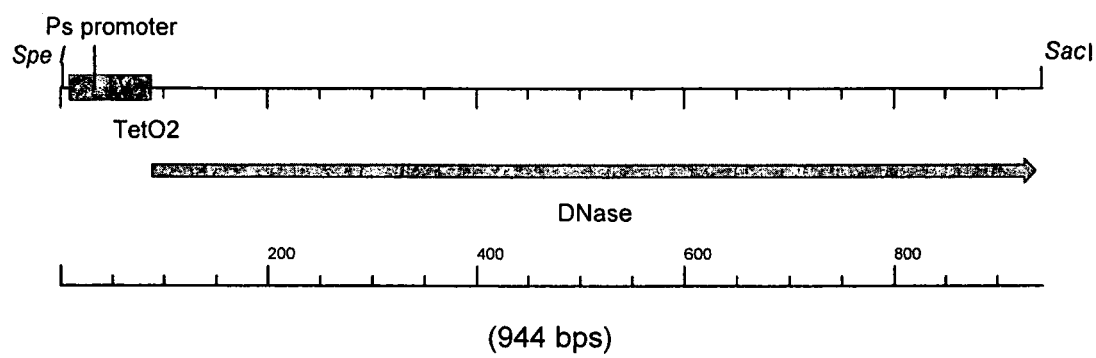
FIG. 5 schematically depicts the resulting fusion of the Ps promoter to the TetO2-DNAse fragment.

This second PCR step resulted in the fragment shown in FIG. 5.

Figure 6:
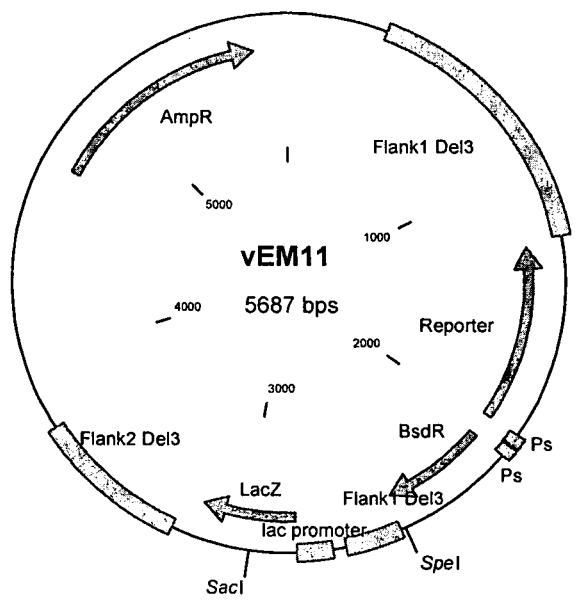
FIG. 6 shows a map of the standard recombination plasmid vEM11 used for cloning recombinant MVA.
Figure 7:
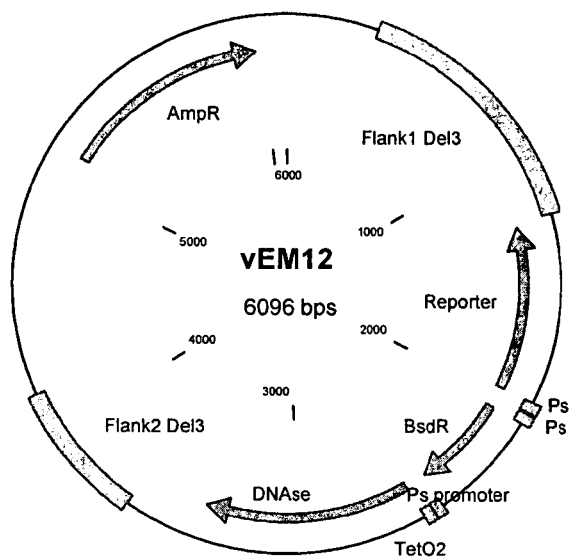
FIG. 7 shows a map of the recombination plasmid vEM12. The Ps-TetO2-DNAse cassette was cloned in the vEM11 plasmid via the SacI and SpeI restriction sites. BsdR=Blasticidine resistance gene.

The resulting fragment was then cloned into the recombination vector vEM11 (FIG. 6) through use of the SpeI and SacI restriction sites. This cloning step resulted in vector vEM12 (FIG. 7).

Cloning of TetR

During the next cloning step, the TetR coding region was inserted into vector vEM12. The amount of expressed TetR is an important experimental parameter, as it has to be sufficiently expressed in order to cover all TetO2 sequences present in the cell (about 200 copies per cell), but should not be expressed in excess as this would require an excess of tetracycline in order to induce the expression of the DNase. Therefore, the TetR expression was assessed under the control of three different promoters: the Ps (strong expression), the H5 (medium expression) and the p7.5 (low expression).

Cloning of Cloning of TetR with the Ps Promoter

The Ps-Tetracycline repressor (TetR) cassette was synthesized by PCR. The template was the pcDNA6/TR plasmid (Invitrogen), and the following oligonucleotides were used for the fusion of the Ps promoter and the amplification:

```
1) oEM163:
                                          (SEQ ID NO: 11)
SacI-Ps-TetRstart; GGGAGCTCAAAAATTGAAATTTTATTTTTT

TTTTTTGGAATATAAATAATGTCTAGATTAGATAAAAG 2) oEM164:
                                          (SEQ ID NO: 12)
TetRend-NheI; GCTAGCTTAATAAGATCTGAATTCC
```

Figure 8:
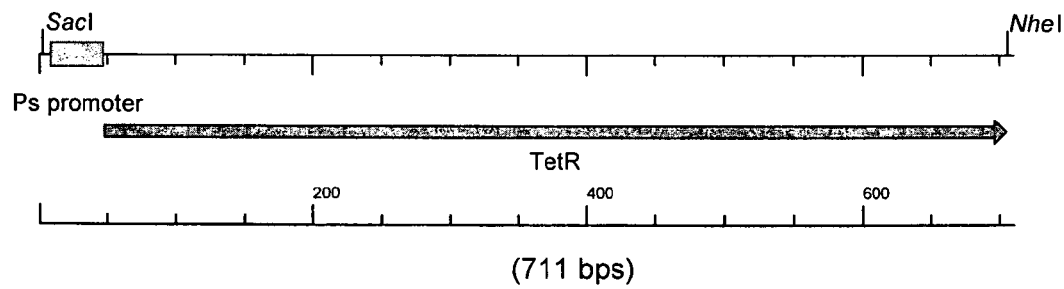
FIG. 8 schematically depicts the fusion of the Ps promoter to the tetracycline repressor coding region (TetR).
Figure 9:
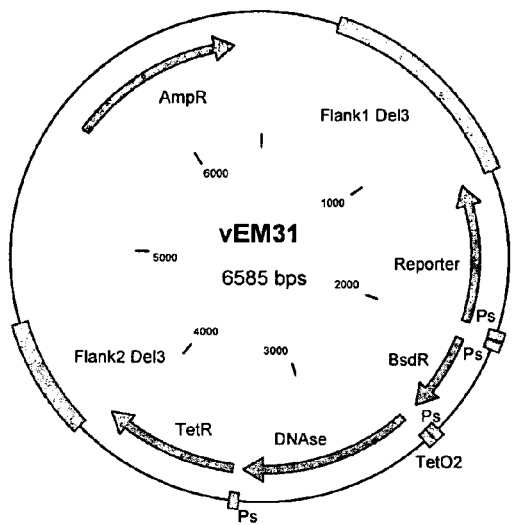
FIG. 9 shows a map of the recombination plasmid vEM31. The Ps-TetR cassette was cloned in the vEM12 plasmid via the SacI and NheI enzymatic restriction sites.

The resulting PCR fragment (FIG. 8) was cloned using SacI and NheI in vector vEM12. This cloning step resulted in vector vEM31, SEQ ID NO: 17 (FIG. 9).

Cloning of TetR with the p7.5/H5 Promoter

The p7.5 and H5 promoter are present in the plasmids pVIV06 (SEQ ID NO:18) and pVIV07 (SEQ ID NO: 19), and TetR was amplified for insertion into these vectors by PCR using the following oligonucleotides:

```
1) oEM165:
                                          (SEQID NO: 13)
XhoI-TetRstart; CTCGAGATGTCTAGATTAGATAAAAG 2) oEM166:
                                          (SEQ ID NO: 14)
TetRend-ApaI; CCGGGCCCTTAATAAGATCTGAATTCC
```

For appropriate fusion of the TetR coding region to the promoters, PCR fragments were cloned via ApaI and XhoI in vector pVIV06 (p7.5) and vector pVIV07 (H5).

The cloning of the TetR in pVIV06 resulted in vector pEM12 (7.5) (SEQ ID NO:20), and the cloning in pVIV07 resulted in vector pEM13 (H5) (SEQ ID NO: 21). The TetR expression cassettes were then extracted using SacI and ApaI and then cloned in vEM12. This resulted in vector vEM32 (7.5) (SEQ ID NO: 22) and vector vEM33 (H5) (SEQ ID NO: 23), which were identical to vector vEM31 (FIG. 9), except for the promoter that is used to express the TetR gene.

Example 2

Cloning of the Modified MVA Vector vEM31, 32 and 33 were each employed to create modified MVA vectors. For this purpose, CEF cells were infected with MVA (moi 0.05) and then transfected with vEM31, 32 or 33, individually. The MVA particles released by the infected CEF cells were then passaged three times using fresh CEF cells and under selective conditions (e.g. blasticidine containing medium; 5 µg/ml), since cells containing recombinant MVA (i.e., the modified MVA vectors) are resistant to this antibiotic. The recombinant MVA particles were subsequently purified by plaque purification and using a FACS unit (fluorescence activated cell sorter).

Following amplification and characterization of the resulting modified MVA vectors resulting from recombination of MVA with vEM31 (mEM06, Ps-TetR), with vEM32 (mEM07, 7.5-TetR) and with vEM33 (mEM08, H5-TetR), the tetracycline/DNase system was used for testing.

Example 3

Assessment of the Tetracycline/DNAse System

For testing the inducible reverse selection system, cells were infected with modified MVA viruses mEM06, 07 and 08 individually and incubated in tetracycline-containing medium. Different concentrations of tetracycline were used for analysis (0-500 μg/ml).

In order to assess the influence of the inducible DNAse expression on the replication of unmodified MVA, MVA-infected cells were transfected with (vEM12) to facilitate the transient expression of DNAse. Furthermore, the influence of tetracycline on the replication of unmodified MVA was analyzed by incubating MVA-infected cells with tetracycline only. Additionally, for monitoring the influence of tetracycline on the growth and status of cells, MVA infected and uninfected CEF cells were incubated with the identical tetracycline concentrations used for testing of the modified virus vectors.

Figure 10:
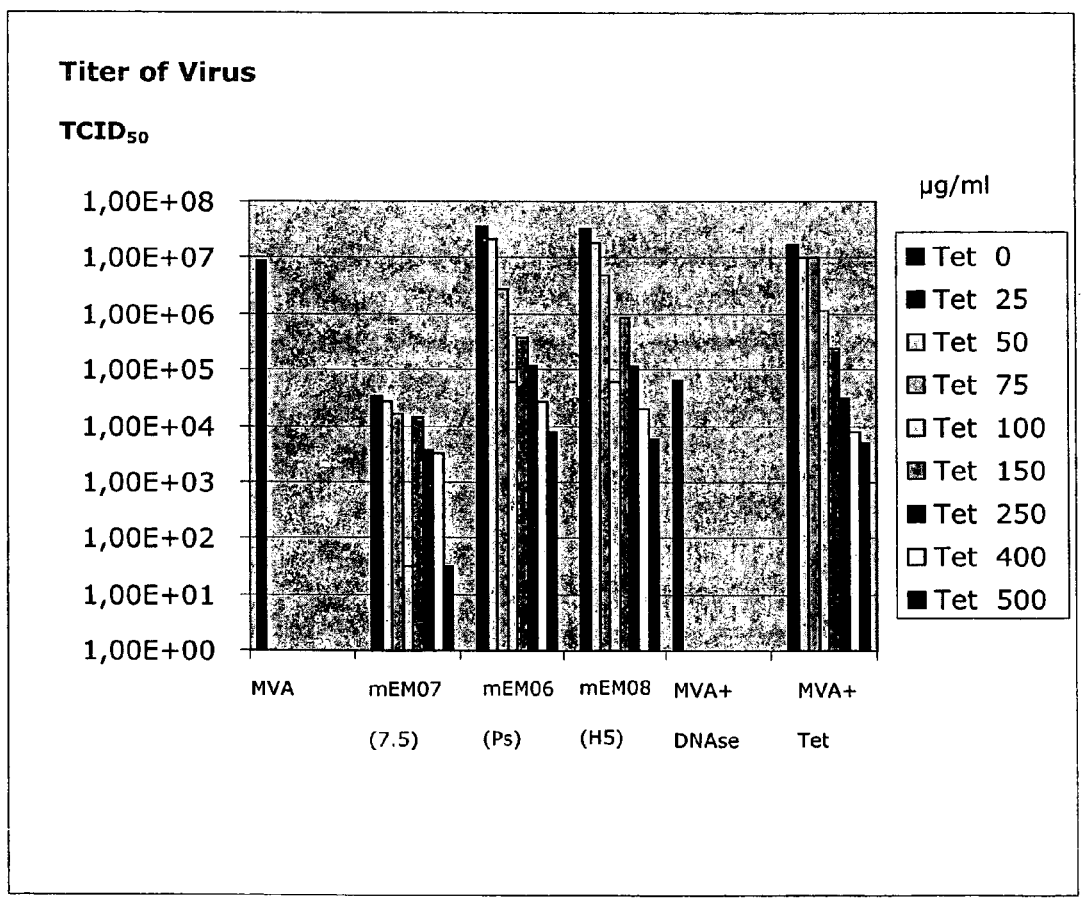
FIG. 10 illustrates the effects of inducible DNAse expression on MVA replication. CEF cells were infected with the recombinant MVA mEM07 (7.5=7.5 promoter), mEM06 (Ps=Ps promoter), mEM08 (H5=H5 promoter) and incubated with media containing different concentrations of tetracycline (Tet 0=no tetracycline; Tet 25=25µ tetracycline per ml). As a control, CEF cells were infected with MVA empty vector (MVA). One set of samples were subsequently transfected with vEM12 (MVA+DNase). After 48 hours of incubation at 37° C., 5% $CO_2$ cells were harvested and the virus titer was determined. CEF cells infected with MVA empty vector were also incubated with tetracycline (MVA+Tet). $TCID_{50}$=Tissue Culture Infectious Dose 50.

Briefly, CEF cells were infected with the modified MVA viruses mEM07 (7.5=7.5 promoter), mEM06 (Ps=Ps promoter), mEM08 (H5=H5 promoter) and incubated with media containing different concentrations of tetracycline (Tet 0=no tetracycline; Tet 25=25 μg tetracycline per ml). For controls, CEF cells were infected with unmodified MVA empty vector (MVA), and some MVA infected cells were also subsequently transfected with vEM12 (MVA+DNase). CEF cells infected with unmodified MVA empty vector were also incubated with tetracycline (MVA+Tet). After 48 hours of incubation at 37° C. (5% $CO_2$), cells were harvested and the virus titer was determined. FIG. 10 provides a summary of the results obtained.

The unmodified MVA control (FIG. 10, MVA) resulted in a titer of $8.75E^{+06}$ $TCID_{50}$. Consequently, this is the titer that can be achieved by infection with unmodified MVA without any the presence of any inhibiting substances under these conditions. The expression of DNase resulted in a titer reduced by 2 log scales (FIG. 10, MVA+DNase, $6.56E^{+04}$ $TCID_{50}$/ml). However, since MVA infection was established by inoculation with $1.00^{E+05}$ $TCID_{50}$/ml of unmodified MVA, this treatment did not result in an increase in amount of virus (i.e. no productive replication), and therefore DNase expression does inhibit viral replication effectively.

Cells infected with unmodified MVA and incubated with tetracycline demonstrated that tetracycline itself has an influence on MVA replication, likely due to a cytotoxic effect. If 25-50 μg tetracycline/ml were used, there was no detectable influence on MVA replication, while using a concentration of 100 μg/ml reduced the MVA replication by 1 log; furthermore, a concentration of 250 μg/ml inhibited the viral replication comparable to the observed effect of transiently expressed DNase (FIG. 10, MVA+Tet). Treatment of cells infected by modified MVA vectors mEM06 and mEM08 with 75 μg/ml tetracycline resulted in a reduced viral replication through induced DNase expression (FIG. 10, mEM06 and mEM08), and this was not due to direct tetracycline exclusively, as the viral titer was reduced even more significantly. This same effect can be observed using 100 μg tetracycline per ml. Concentrations of 150 μg/ml result in a pronounced cytotoxic effect of tetracycline such that the modified MVA viruses do not replicate at all. Accordingly, for further testing purposes, a narrow concentration window of 75 to 100 μg tetracycline per ml was used. Modified MVA vector mEM07 expresses TetR with a weak p7.5 promoter clearly produces an insufficient amount of TetR for inhibiting the DNase expression in any quantitative amount. Therefore, the viral replication is markedly reduced in all experimental arrangements, and the virus itself is not applicable as a basic virus for the cloning of recombinant viruses with a single recombination vector.

Example 4

Cloning of a Recombinant Poxvirus Vector Using the Single Recombination System

Since modified MVA viruses mEM06 and mEM08 demonstrated similar replication patterns, additional experiments were performed using mEM06.

Figure 3:
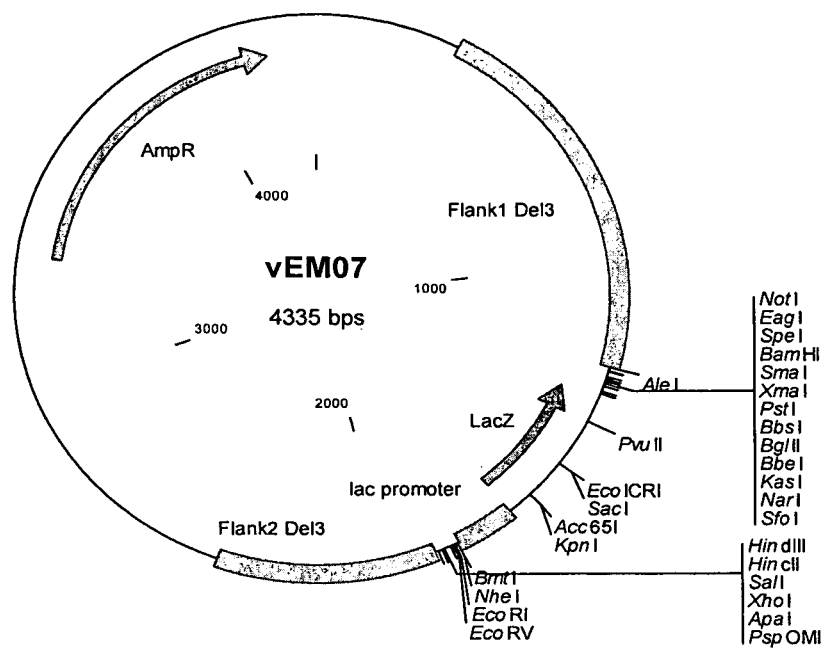
FIG. 3 provides a map of the exemplary plasmid (vEM07; SEQ ID NO: 1) used for inserting genetic material of interest into the MVA genome, as schematically shown in FIG. 2. LacZ=Bacterial gene coding for β-Galactosidase.
Figure 11:
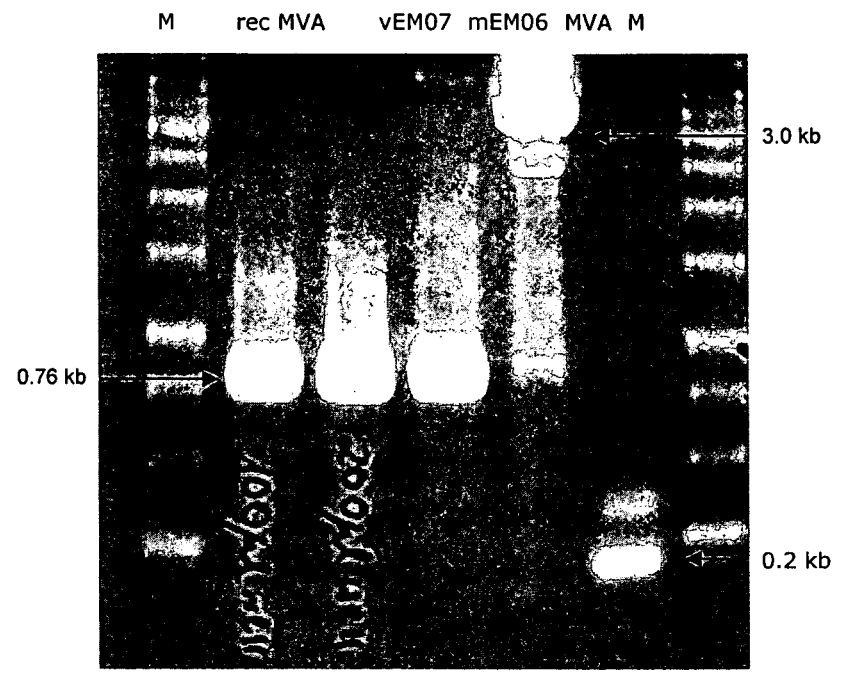

Cells were infected with modified MVA virus mEM06 and transfected with vEM07 (FIG. 3). Due to homologous recombination, the LacZ gene was inserted in select modified MVA virus genomes and the reporter/selection cassette was deleted. The released virus particles were passaged on fresh CEF cells in medium containing tetracycline (100 μg/ml), and then passaged by serial dilution on cells without selective conditions. Infected cells were sorted using a FACS to select non-fluorescing cells. Once the settings for the sorting process were optimized, the sorted cells were homogenized and passaged again on CEF cells. The infected cells were sorted and the virus was amplified once more on fresh CEF cells. The cells were clearly infected and exhibited no fluorescence, meaning that they contained purified recombinant MVA virus. Recombinant virus purity was confirmed by a PCR procedure that amplified the insertion site of the modified MVA vector (FIG. 11). The PCR produced a 3.0 kb signal for the modified MVA vector, and a smaller 0.76 kb fragment for the recombinant MVA containing LacZ which had replaced the reporter/selection cassette by homologous recombination.

The recombinant MVA virus samples provided a clear signal at 0.76 kb (FIG. 11, rec MVA), but no signal for modified MVA (mEM06) or unmodified MVA (MVA). The recombination vector vEM07 also produced the expected signal of 0.76 kb (FIG. 11, vEM07). The modified MVA containing the selection/reporter cassette within the deletion site was used as a control, and this showed the expected signal of 3.0 kb (mEM06). The unmodified MVA vector also resulted in the expected signal of about 200 base pairs (MVA).

In order to confirm the robust results achieved by the present system, the cloning process was repeated using the procedures described above. A recombinant MVA was again readily isolated using the described single recombination system.

Example 5

Cloning of a Further Recombinant Poxvirus Vector Using the Single Recombination System A recombinant poxvirus is cloned using the single recombination system according to the invention using a modified poxvirus vector comprising a reporter gene located between a pair of flanking sequences allowing for homologous recombination is used.

Cells are infected with the modified MVA virus and then transfected with vEM07 (FIG. 3). Due to homologous recombination, the LacZ gene is inserted in select modified MVA virus genomes and consequently the reporter cassette is deleted. The released virus particles are then passaged at least once on fresh CEF cells in medium containing tetracycline (100 μg/ml).

Infected cells are then sorted using FACS to select non-fluorescing cells as described above. After the infected cells have been sorted the virus is amplified once more on fresh CEF cells.

The recombinant virus purity is confirmed by a PCR procedure that amplifies the insertion site of the modified MVA vector (FIG. 11). The PCR produces a fragment for the recombinant MVA containing LacZ which has replaced the reporter cassette by homologous recombination.

The invention claimed is:

1. A system for recombination in a recombinant poxvirus, comprising:
   (1) a recombinant poxvirus comprising a cassette which comprises a reporter gene and a selection gene whose expression is regulated by an inducible expression system, and
   (2) a plasmid comprising a gene of interest flanked by DNA homologous to the DNA which flanks the cassette in the recombinant poxvirus.

2. The system of claim 1, wherein the reporter gene encodes a fluorescent protein.

3. The system of claim 1, wherein expression of the selection gene inhibits or slows down poxvirus replication in a host cell.

4. The system of claim 1, wherein expression of the selection gene is cytotoxic to a host cell.

5. The system of claim 1, wherein the selection gene codes for a DNAse.

6. The system of claim 1, wherein the inducible expression system comprises a tetracycline operator/repressor.

7. The system of claim 1, wherein the poxvirus is vaccinia or MVA (Modified Vaccinia Ankara).

8. A method for generating a recombinant poxvirus comprising a gene of interest, comprising the steps of:
   (1) infecting permissive host cells with a modified poxvirus comprising a cassette comprising a reporter gene and a selection gene whose expression is regulated by an inducible expression system; and
   (2) transfecting said permissive host cells with a plasmid comprising said gene of interest flanked by DNA homologous to the DNA which flanks the cassette in the modified poxvirus, under conditions that permit homologous recombination between said modified poxvirus and said plasmid, whereby the recombinant poxvirus is produced in which the gene of interest has replaced the reporter gene and the selection gene.

9. The method of claim 8, further comprising a step of selecting against the selection gene under conditions in which expression of the selection gene is induced.

10. The method of claim 9, wherein expression of the selection gene inhibits or slows down poxvirus replication in the host cell.

11. The method of claim 10, wherein the selection gene codes for a DNAse.

12. The method of claim 9, wherein expression of the selection gene is cytotoxic to the host cell.

13. The method of claim 8, wherein the reporter gene encodes a fluorescent protein.

14. The method of claim 8, wherein the inducible expression system comprises a tetracycline operator/repressor.

15. The method of claim 8, wherein the poxvirus is vaccinia or MVA (Modified Vaccinia Ankara).

16. The method of claim 8, further comprising passaging the resulting recombinant poxvirus on fresh permissive host cells.

17. The method of claim 8, further comprising the step of: separating the permissive host cells comprising the recombinant poxvirus from permissive host cells comprising the modified poxvirus that has not undergone homologous recombination with the plasmid comprising the gene of interest.

18. The method of claim 9, further comprising the step of: separating the permissive host cells comprising the recombinant poxvirus from permissive host cells comprising the modified poxvirus that has not undergone homologous recombination with the plasmid comprising the gene of interest.

19. An isolated cell comprising:
   (i) a recombinant poxvirus comprising a cassette which comprises a reporter gene and a selection gene whose expression is regulated by an inducible expression system; and
   (ii) a plasmid comprising a gene of interest flanked by DNA homologous to the DNA which flanks the cassette in the recombinant poxvirus.

20. The isolated cell of claim 19, wherein the cell is a chicken embryo fibroblast.

21. The isolated cell of claim 19, wherein the cell is a human cell.

* * * * *